United States Patent [19]

Heymes et al.

[11] 4,439,433

[45] Mar. 27, 1984

[54] OXIMES

[75] Inventors: René Heymes, Romainville; Michel Vignau, Neuilly-sur-Seine, both of France

[73] Assignee: Roussel Uclaf, Paris, France

[21] Appl. No.: 267,638

[22] Filed: May 27, 1981

Related U.S. Application Data

[62] Division of Ser. No. 25,666, Mar. 30, 1979, abandoned.

[30] Foreign Application Priority Data

Mar. 31, 1978 [FR] France ............................. 78 09617
Aug. 24, 1978 [FR] France ............................. 78 24563

[51] Int. Cl.³ .................. A61K 31/545; C07D 501/34
[52] U.S. Cl. ..................................... 424/246; 544/22; 544/27; 544/28; 548/194
[58] Field of Search ............................ 544/28, 22, 27; 424/246

[56] References Cited

U.S. PATENT DOCUMENTS 4,278,793 7/1981 Durckheimer et al. ............. 544/28
4,284,631 8/1981 Takaya et al. ....................... 544/22

Primary Examiner—Paul M. Coughlan, Jr.
Attorney, Agent, or Firm—Bierman, Bierman, Peroff & Muserlian

[57] ABSTRACT

Novel oximes of the syn isomers of 7-[2-(2-amino-4-thiazolyl)-acetamido]ceph-3-eme-4-carboxylic acid compounds of the fomrula

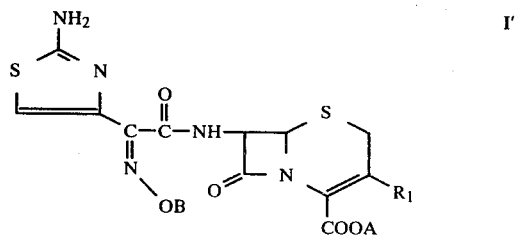

wherein B is $-(CH_2)_{n'}-R_5$, $n'$ is an integer from 1 to 4, $R_5$ is

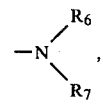

$R_6$ and $R_7$ are individually selected from the group consisting of hydrogen and alkyl of 1 to 4 carbon atoms and when taken together with the nitrogen to which they are attached are selected from the group consisting of phthalimido and 1-pyridinyl, $R_1$ is selected from the group consisting of chloro, $CH_3O-$, alkyl and alkylthio of 1 to 5 carbon atoms, cycloalkyl of 3 to 5 carbon atoms, $-CH_2-S-R_{12}$, acetoxymethyl, carbamoyloxymethyl and

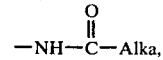

$R_{12}$ is selected from the group consisting of 2-oxo-(3H)-thiazolin-4-yl-carbonyl, 3-methyl-1,2-oxazol-5-yl-carbonyl, acyl of an alkanoic acid of 2 to 4 carbon atoms and a nitrogen heterocycle, Alka is alkyl of 1 to 4 carbon atoms and A is selected from the group consisting of hydrogen, $-NH_4$, alkali metal, alkaline earth metal, magnesium, a non-toxic, pharmaceutically acceptable organic amine and easily cleaved ester and their non-toxic, pharmaceutically acceptable acid addition salts; having antibacterial activity and novel intermediates therefore.

20 Claims, No Drawings

OXIMES

This is a division of Ser. No. 25,666 filed Mar. 30, 1979, now abandoned.

STATE OF THE ART

Related prior art in this fields includes French Patent Nos. 2,137,899, and 2,294,690, 2,348,218 and 2,348,219 and commonly assigned U.S. patent application Ser. Nos. 761,270 filed Jan. 21, 1977, now abandoned in favor of cip application Ser. No. 817,114 filed July 19, 1977, now U.S. Pat. No. 4,152,432 and Ser. No. 796,315 filed May 12, 1977.

OBJECTS OF THE INVENTION

It is an object of the invention to provide the novel syn isomers of the oximes of formula I′ and novel intermediates therefore.

It is another object of the invention to provide novel antibacterial compositions and to provide a method of treating bacterial infections in warm-blooded animals.

These and other objects and advantages of the invention will become obvious from the following detailed description.

THE INVENTION

The novel products of the invention are selected from the group consisting of oximes of the syn isomers of 7-[2-(2-amino-4-thiazolyl)-2-acetamido]-ceph-3-eme-4-carboxylic acid compounds of the formula

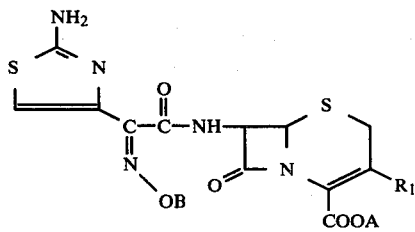

wherein B is selected from the group consisting of R, $R_a$ and $R_b$, R is selected from the group consisting of

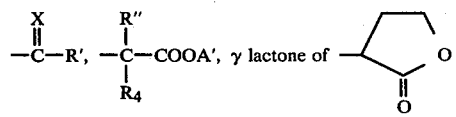

and $-(CH_2)_{n'}-R_5$, X is selected from the group consisting of oxygen and sulfur, R′ is selected from the group consisting of alkyl and alkoxy of 1 to 4 carbon atoms, phenyl and

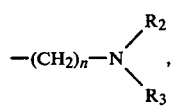

n is an integer from 0 to 4 and $R_2$ and $R_3$ are individually selected from the group consisting of hydrogen and alkyl of 1 to 4 carbon atoms or taken together with the nitrogen atom to which they are attached are selected from the group consisting of piperidino, morpholino and phthalimido, A′ is selected from the group consisting of hydrogen, alkali metal, alkaline earth metal, magnesium, $-NH_4$ and non-toxic, pharmaceutically acceptable organic amine and easily removable esters, $R_4$ is selected from the group consisting of phenyl, hydroxyethyl and $-CN$, R″ is selected from the group consisting of hydrogen and alkyl of 1 to 4 carbon atoms, n′ is an integer from 1 to 4, $R_5$ is selected from the group consisting of alkoxy,

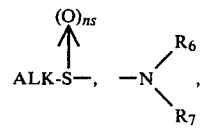

$-CN$ when n′ is other than 1,

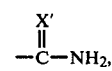

4-methyl-1,3-thiazol-2-yl, 4-amino-1,3-thiazol-2-yl, 1,2,3,4-tetrazol-5-yl, azido and acyl of an alkanoic acid of 2 to 4 carbon atoms, Alk is alkyl of 1 to 4 carbon atoms, ns is an integer from 0 to 2, $R_6$ and $R_7$ are individually selected from the group consisting of hydrogen and alkyl of 1 to 4 carbon atoms and when taken together with the nitrogen to which they are attached are selected from the group consisting of phthalimido and 1-pyridinyl, X′ is sulfur or when n′ is other than 1, oxygen, $R_a$ is selected from the group consisting of halogen and $-S-R_{ar}$, $R_{ar}$ is selected from the group consisting of phenyl and aromatic heterocycle of 5 to 6 carbon atoms and having 1 to 4 heteroatoms selected from the group consisting of oxygen, sulfur and nitrogen, both being optionally substituted with at least one member of the group consisting of $-NH_2$, $-NO_2$, $-CN$ and alkyl of 1 to 4 carbon atoms, $R_b$ is $-(CH_2)_{n'}-R_{5b}$, n′ is an integer from 1 to 4, $R_{5b}$ is

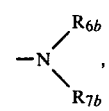

$R_{6b}$ and $R_{7b}$ taken together with the nitrogen atom to which they are attached are selected from the group consisting of imidazolyl, morpholinyl and N-alkyl piperazinyl with 1 to 4 alkyl carbon atoms, $R_1$ is selected from the group consisting of chloro, $CH_3O-$, alkyl and alkylthio of 1 to 5 carbon atoms, cycloalkyl of 3 to 5 carbon atoms, $-CH_2-S-R_{12}$, acetoxymethyl, carbamoyloxymethyl and

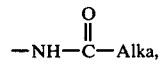

$R_{12}$ is selected from the group consisting of 2-oxo-(3H)-thiazolin-4-yl-carbonyl, 3-methyl-1,2-oxazol-5-yl-carbonyl, acyl of an alkanoic acid of 2 to 4 carbon atoms and a nitrogen heterocycle, Alka is alkyl of 1 to 4 carbon atoms and A is selected from the group consisting of hydrogen, $-NH_4$, alkali metal, alkaline earth metal, magnesium, a non-toxic, pharmaceutically acceptable organic amine and easily cleaved ester and their non-toxic, pharmaceutically acceptable acid addition salts.

Among the preferred compounds of formula I are the syn isomers selected from the group consisting of compounds of the formulae

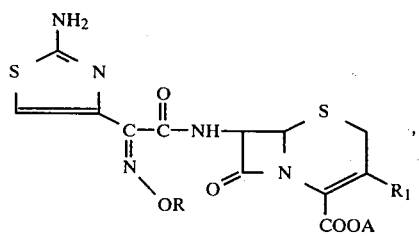

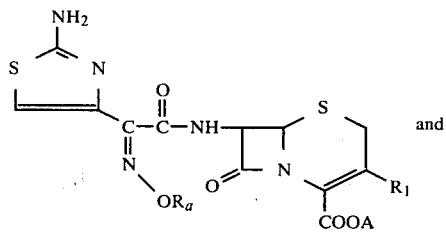

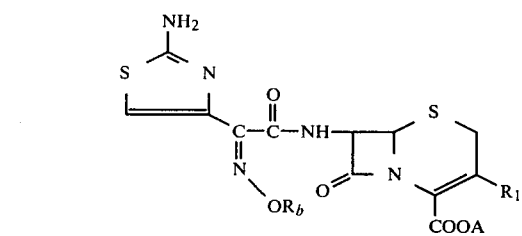

wherein R, $R_1$, A, $R_a$ and $R_b$ have the above definitions and their non-toxic, pharmaceutically acceptable acid addition salts.

Examples of suitable values for R are acyl groups such as acetyl, propionyl, butyryl, isobutyryl, valeryl, isovaleryl and tert.valeryl and the corresponding thioacyl groups such as thioacetyl; alkoxycarbonyl such as methoxycarbonyl, ethoxycarbonyl, propyloxycarbonyl, isopropyloxycarbonyl, butoxycarbonyl, isobutoxycarbonyl and tert.-butoxycarbonyl as well as the corresponding alkoxythiocarbonyls, such as methoxythiocarbonyl.

Examples of other values for R are carbamoyl, N-methyl-carbamoyl, N,N-dimethyl-carbamoyl, aminoacetyl, dimethylaminoacetyl, methylaminopropionyl, dimethylaminopropionyl, aminovaleryl, dimethylaminovaleryl, N-piperidinocarbonyl, N-piperidinoacetyl, N-piperidino-propionyl, N-phthalimidocarbonyl, N-phthalimidoacetyl, N-phthalimidopropionyl and benzoyl.

Other suitable values for R are acetylmethyl, acetylethyl, propionylmethyl, propionylethyl, methoxymethyl, methoxyethyl, ethoxyethyl, methoxypropyl, methylthiomethyl, methylthioethyl, ethylthiomethyl and ethylthioethyl as well as the corresponding sulfur compounds which have been oxidized such as methylsulfinylmethyl and methylsulfonylmethyl.

Other suitable substitutes for R are aminomethyl, methylaminomethyl, dimethylaminomethyl, dimethylaminoethyl, dimethylaminopropyl, phthalimidomethyl, phthalimidoethyl, phthalimidopropyl, N-pyridinylmethyl, N-pyridinylethyl, N-pyridinylpropyl, thiocarbamoylmethyl, carbamoylethyl, carbamoylpropyl, thiocarbamoylethyl, 4-aminothiazol-2-ylmethyl, 4-methylthiazol-2-ylmethyl, 1,2,3,4-tetrazol-5-ylmethyl and 1,2,3,4-tetrazol-5-ylethyl.

Examples of suitable $R_{5a}$ values are fluorine, chlorine, bromine, iodine, phenyl, 1,2,3-thiadiazolyl, 1,2,5-thiadiazolyl, 1,2,4-thiadiazolyl, 1,3,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl, 1,3,4-oxadiazolyl, 2-pyridinyl, 3-pyridinyl, 4-pyridinyl, 2-furyl, 3-furyl, 2-thienyl, 3-thienyl, 2-pyrolyl and 3-pyrolyl, all of which are optionally substituted with at least one member of the group consisting of $-NH_2$, $-NO_2$, methyl, ethyl, propyl, isopropyl, butyl, sec-butyl, tert.-butyl and $-CN$.

Examples of suitable $R_{5b}$ groups are N-alkyl-piperazin-1-yls such as 4-methyl-piperazin-1-yl, 4-ethyl-piperazin-1-yl, 4-propyl-piperazin-1-yl, 4-isopropyl-piperazin-1-yl, 4-butyl-piperazin-1-yl, 4-sec.-butyl-piperazin-1-yl and 4-tert.-butyl-piperazin-1-yl.

Examples of suitable $R_1$ substituents are methyl, ethyl, propyl, isopropyl, butyl isobutyl, tert.-butyl, pentyl, sec-pentyl, tert.-pentyl, cyclopropyl, cyclobutyl, and cyclopentyl; alkylthio such as methylthio, ethylthio, isopropylthio, propylthio, butylthio, isobutylthio and tert.-butylthio; amides such as acetamido, propionylamido, butyrylamido, isobutyrylamido and valerylamido; $-CH_2-S-R_{12}$ and $R_{12}$ is acyl selected from the group consisting of acetyl, butyryl and propionyl or a heterocyclic selected from the group consisting of 1,2,3-thiadiazolyl, 1,2,5-thiadiazolyl, 1,3,4-thiadiazolyl, 1,2,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl, the said heterocycles being optionally substituted with at least one substituted selected from the group consisting of methyl, ethyl, propyl, isopropyl, methoxy, ethoxy, propoxy, isopropoxy, amino, hydroxycarbonylmethyl, dimethylaminoethyl and diethylaminoethyl.

Specific preferred $R_{12}$ groups are 3-methyl-1,2,4-thiadiazol-5-yl, 3-ethyl-1,2,4-thiadiazol-5-yl, 3-propyl-1,2,4-thiadiazol-5-yl, 3-methoxy-1,2,4-thiadiazol-5-yl, 3-ethoxy-1,2,4-thiadiazol-5-yl and 3-propoxy-1,2,4-thiadiazol-5-yl.

Examples of suitable groups of A are hydrogen, alkali metals such as sodium, potassium and lithium, alkaline earth metals such as calcium, magnesium, $-NH_4$ and non-toxic, pharmaceutically acceptable organic amines such as trimethylamine, diethylamine, triethylamine, methylamine, propylamine, N,N-dimethylethanolamine, tris(hydroxymethyl)aminomethane, ethanolamine, pyridine, picoline, dicyclohexylamine, N,N'-dibenzylethylenediamine, morpholine, benzylamine, procaine, lysine, arginine, histidine and N-methylglucamine.

Examples of easily cleaved esters for A are methoxymethyl, ethoxymethyl, isopropoxymethyl, α-methoxyethyl, α-ethoxyethyl, methylthiomethyl, ethylthiomethyl, isopropylthiomethyl, pivaloyloxymethyl, acetoxymethyl, propionyloxymethyl, isobutyryloxymethyl, isovaleryloxymethyl, propionyloxyethyl, isovaleryloxyethyl, 1-acetoxyethyl, 1-acetoxypropyl, 1-acetoxybutyl, 1-acetoxyhexyl and 1-acetoxyheptyl.

Examples of suitable acids for the non-toxic, pharmaceutically acceptable acid addition salts are inorganic acids such as hydrochloric acid, hydrobromic acid, hydroiodic acid, sulfuric acid and phosphoric acid and organic acids such as acetic acid, trifluoroacetic acid, maleic acid, tartaric acid, methanesulfonic acid, benzenesulfonic acid and p-toluene sulfonic acid. The compounds of formula I' when B is $R_b$ may form internal salts.

Among the preferred compounds of formula I' are those wherein $R_{12}$ is acyl selected from the group consisting of acetyl, butyryl, and propionyl or a heterocyclic selected from the group consisting of 1,2,3-thiadiazolyl, 1,2,5-thiadiazolyl, 1,3,4-thiadiazolyl, 1,2,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl, the said heterocycles being optionally substituted with at least one substitute selected from the group consisting of methyl, ethyl, propyl, isopropyl, methoxy, ethoxy, propoxy, isopropoxy, amino, hydroxycarbonyl methyl, dimethylaminoethyl and diethylaminoethyl.

Especially preferred in this group is $R_{12}$ as acetyl, 1-methyl-1-tetrazolyl, 2-methyl-1,3,4-thiadiazolyl, 3-methyl-1,2,4-thiadiazol-5-yl, 3-methoxy-1,2,4-thiadiazolyl, 1,3,4-thiadiazol-5-yl, 2-amino-1,3,4-thiadiazol-5-yl, 3-hydroxycarbonylmethyl-1,2,4-thiadiazol-5-yl, 5-methoxy-1,2,4-thiadiazol-3-yl, 4-methyl-5-hydroxycarbonylmethyl-1,3,-thiazol-2-yl and 1-dimethylaminoethyl-1,2,3,4-tetrazol-5-yl.

Another preferred group of compounds of formula I are those wherein R is

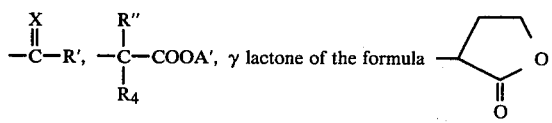, γ lactone of the formula 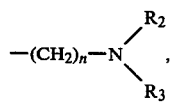

or $(CH_2)_{n'}$—$R_5$, X is oxygen, R' is alkyl of 1 to 4 carbon atoms, phenyl or

, n is 0 or 1, $R_2$ and $R_3$ have the above definitions, A' and R" are hydrogen, $R_4$ is phenyl or hydroxyethyl, n' is 1 or 2, $R_5$ is

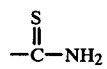

where $R_6$ and $R_7$ have the above definitions of $$-\overset{S}{\underset{\|}{C}}-NH_2$$

or acetyl or 1,2,3,4-tetrazol-5-yl, $R_1$ is acetoxymethyl, alkyl of 1 to 5 carbon atoms or —$CH_2$—S—$R_{12}$ and $R_{12}$ is 2-methyl-1,3,4-thiadiazolyl or 1-methyl-tetrazolyl and A is hydrogen, alkali metal, alkaline earth metal, magnesium, —$NH_4$ or a non-toxic, pharmaceutically acceptable organic amine.

A more preferred group of compounds of formula I are those where R is selected from the group consisting of acetyl, benzoyl, phthalimidoacetyl, N,N-dimethylcarbamoyl, α-carboxyphenylmethyl, 2-oxo-3-tetrahydropyranyl, tetrazol-5-yl-methyl, 2-amino-2-thioxoethyl and 2-oxo-propyl, $R_1$ is selected from the group consisting of methyl, acetoxymethyl, 2-methyl-1,3,4-thiadiazolyl-5-yl-thiomethyl and 1-methyltetrazolyl-thiomethyl and A is hydrogen or sodium.

A more selected group of compounds of formula I are those wherein R is selected from the group consisting of acetyl, benzoyl, phthalimidomethyl tetrazol-5-ylmethylaminoethyl and α-carboxyphenylmethyl and $R_1$ is selected from the group consisting of acetoxymethyl, 2-methyl-1,3,4-thiadiazol-5-yl-thiomethyl and 1-methyl-tetrazol-5-yl-thiomethyl.

Among the preferred compounds of formula $I_a$ are those wherein $R_{5a}$ is selected from the group consisting of bromine, iodine, phenylthio, 2-pyridinylthio, 2-amino-1,3,4-thiadiazol-5-ylthio, 1-methyl-1H-tetrazol-5-ylthio, 2-aminophenylthio, 5-nitro-2-pyridinylthio and 3-cyano-6-methyl-2-pyridinylthio.

Especially preferred specific compounds are the syn isomer of 3-acetoxymethyl-7-[2-(2-amino-4-thiazolyl)-2-(2-aminoethoxyimino)-acetamido]-ceph-3-eme-4-carboxylic acid, the syn isomer of 3-acetoxymethyl-7-[2-(2-amino-4-thiazolyl)-2-(2-bromoethoxyimino)-acetamido]-ceph-3-eme-4-carboxylic acid, and the syn isomer of 3-acetoxymethyl-7-/2-(2-amino-4-thiazolyl)-2-(2-iodoethoxyimino)-acetamido/ceph-3-eme-4-carboxylic acid and their alkali metal, alkaline earth metal, magnesium, ammonium and organic amine salts and their easily cleaved esters.

The compounds of formula I' may exist in the form of the previously indicated structure or in the form of formula

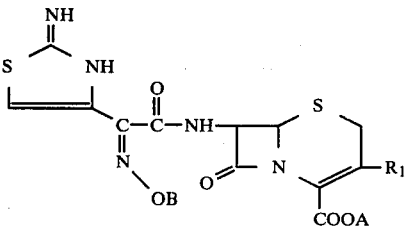 $I_z$

The process of the invention for the preparation of the compounds of formula I' comprises reacting a syn isomer of a compound of the formula

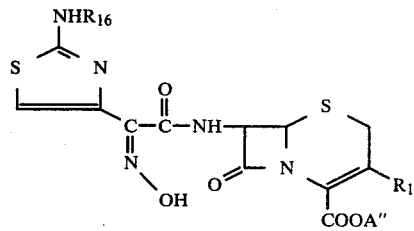 II wherein $R_1$ has the above definition, $R_{16}$ is a amino protective group either (a) with a functional derivative of

wherein X is selected from the group consisting of oxygen and sulfur, $R_3'$ is selected from the group consisting of alkyl and alkoxy of 1 to 4 carbon atoms, phenyl and

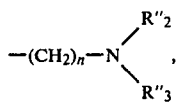

n is an integer from 0 to 4, $R_2''$ and $R_3''$ are individually selected from the group consisting of hydrogen and alkyl of 1 to 4 carbon atoms with at least one being alkyl when n is 0 and $R_2''$ and $R_3''$ together with the nitrogen atom to which they are attached are selected from the group consisting of phthalimido, piperidino and morpholino to obtain a compound of the formula

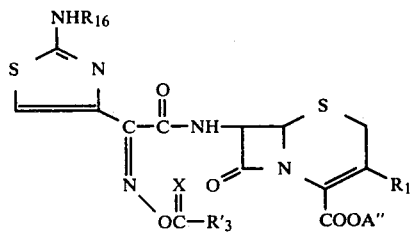

III$_A$ or (b) with the compound of the formula X=C=NH wherein X is oxygen or sulfur to obtain a compound of the formula

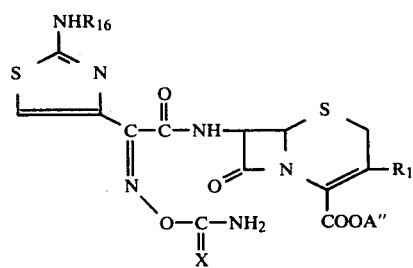

III'$_A$ or (c) with a compound of the formula

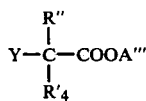

wherein Y is selected from the group consisting of halogen, sulfate and sulfonate, R" is selected from the group consisting of hydrogen and alkyl of 1 to 4 carbon atoms, $R_4'$ is selected from the group consisting of phenyl and —CN and A'" is an easily removeable group to obtain a compound of the formula

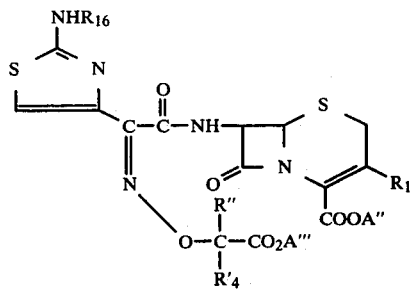

III$_B$ or (d) with a compound of the formula

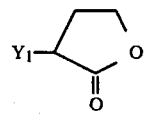

wherein $Y_1$ has the same definition as Y to obtain a compound of the formula

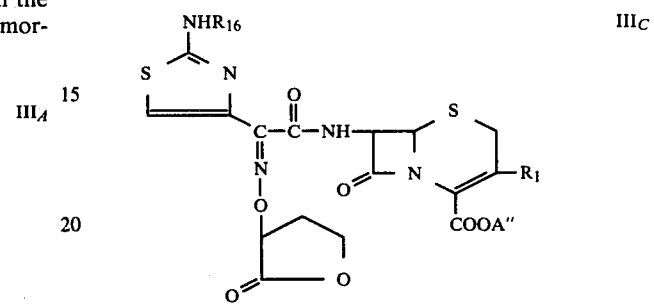

III$_C$ and treating the latter with an alkaline base to obtain a compound of the formula

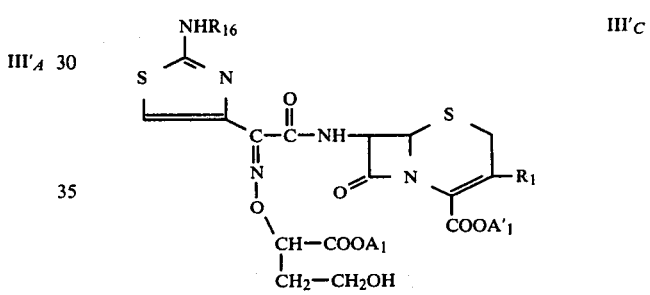

III'$_C$ wherein $A_1'$ is selected from the group consisting of alkali metal and an easily removable ester and $A_1$ is an alkali metal or (e) with a compound of the formula $Y_2$—(CH$_2$)$_{n'}$—$R_5'$ wherein n' is an integer from 1 to 4, $Y_2$ is the same as Y and $R_5'$ is selected from the group consisting of acyl of an alkanoic acid of 2 to 4 carbon atoms, alkoxy of 1 to 4 carbon atoms and alkylthio of 1 to 4 carbon atoms with the sulfur optionally oxidized to sulfone or sulfoxide to obtain a compound of the formula

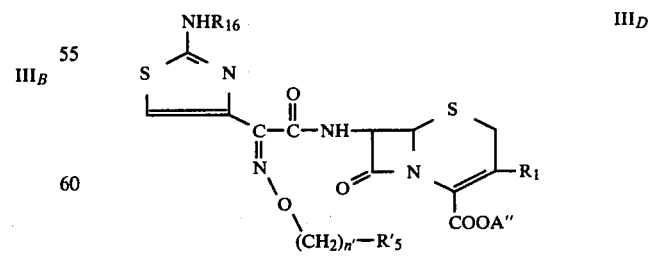

III$_D$ or (f) with a compound of the formula $Y_3$—(CH$_2$)$_{n2}$—CN wherein $Y_3$ has the value of Y and $n_2$ is an integer from 2 to 4 to obtain a compound of the formula

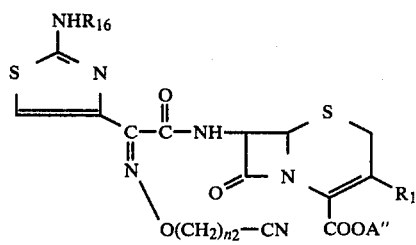

The compounds of formula I' may further be prepared by reacting a compound of the formula

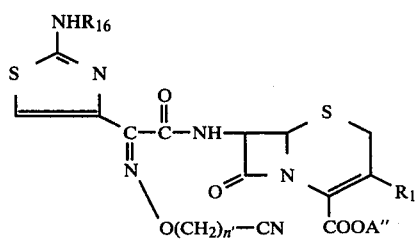

wherein $R_{16}$, $R_1$ and $A''$ have the above definitions and $n'$ is an integer from 1 to 4 with either hydrogen sulfide or when $n'$ is other than 1 by hydrolysis in the presence of a base to obtain a compound of the formula

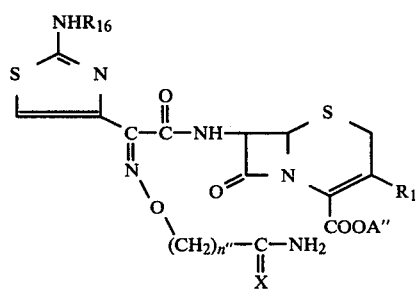

wherein X is sulfur or oxygen and $n''$ is an integer from 1 to 4 when X is sulfur and $n''$ is an integer of 2 to 4 when X is oxygen. When X is sulfur, the compound of formula $III_F$ may be reacted with a compound of the formula

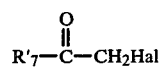

when $R_7'$ is selected from the group consisting of methyl and amino and Hal is halogen to obtain a compound of the formula

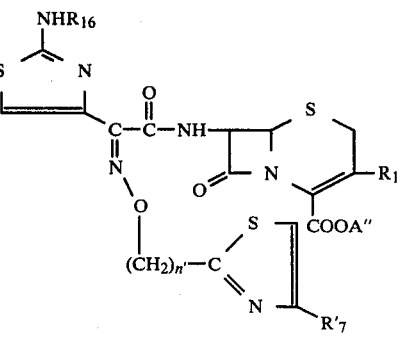

The compound of formula IV may also be reacted with azide to obtain a compound of the formula

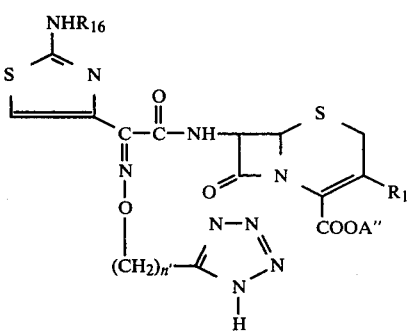

or the compound of formula II may be reacted with a compound of the formula Hal—$(CH_2)_{n'}$-Hal to obtain a compound of the formula

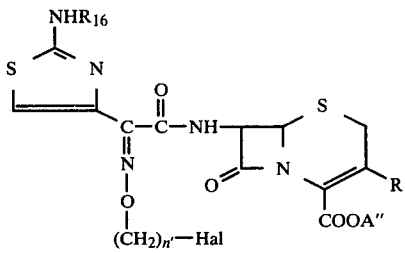

which can be reacted either with pyridine to obtain a compound of the formula

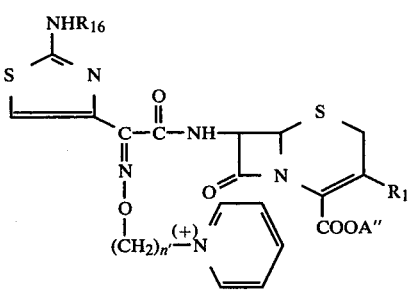

or with azide to obtain a compound of the formula

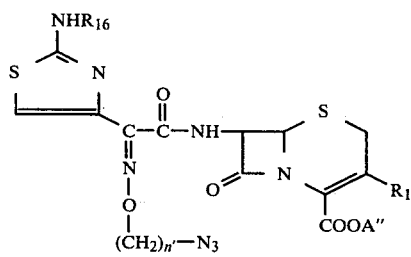

which, if desired, can be reacted with a reducing agent to obtain a compound of the formula

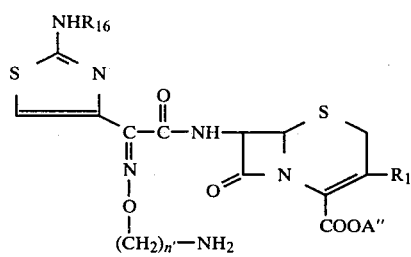

A compound of formula V may also be reacted with (a) an amine of the formula $R_{18}$—NH—$R_{19}$ wherein $R_{18}$ is selected from the group consisting of alkyl of 1 to 4 carbon atoms and groups easily removed by acid hydrolysis and hydrogenolysis and $R_{19}$ is selected from the group consisting of hydrogen and alkyl of 1 to 4 carbon atoms or $R_{18}$ and $R_{19}$ taken together form a phthalimido group to obtain a compound of the formula

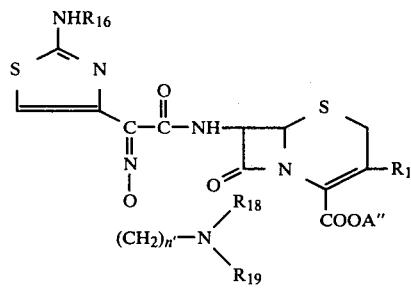

or (b) with a member of the group consisting of imidazole, morpholine and N-alkyl piperazine with 1 to 4 alkyl carbon atoms to obtain a compound of the formula

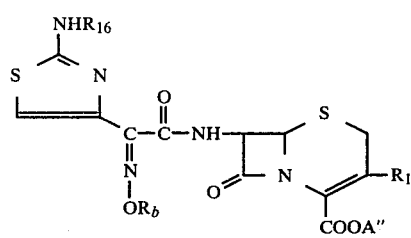

wherein $R_b$ has the above definition or (c) with a compound of the formula $R_{ar}$—SH wherein $R_{ar}$ has the above definition to form a compound of the formula

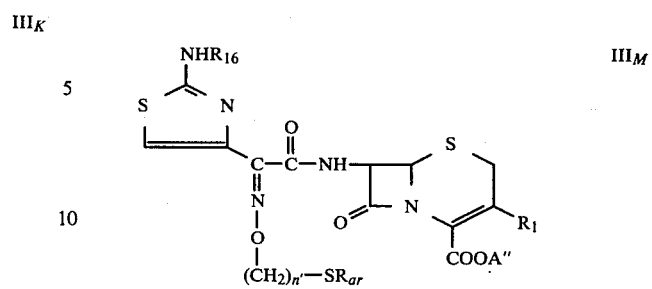

The various compounds of formulae $III_A$ to $III_M$ and $III_A'$, $III_C'$, $III_L'$, $III_K'$ and V may be treated with one or more acid hydrolysis agents, hydrogenolysis agents and thiourea to obtain the following compounds of formula I':

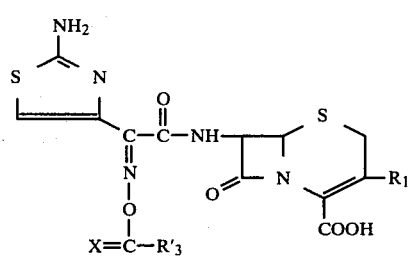

wherein X, $R_3'$ and $R_1$ have the above definitions,

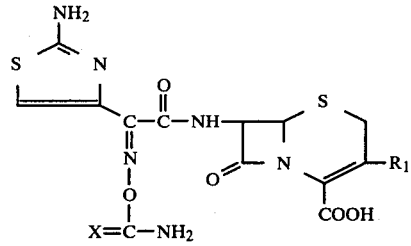

wherein X and $R_1$ have the above definitions

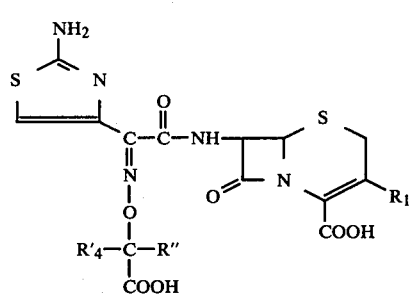

wherein $R_1$, R" and $R_4'$ have the above defintions,

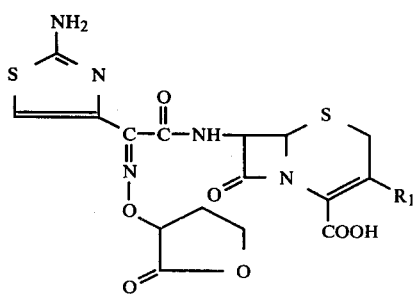

wherein R₁ has the above definition

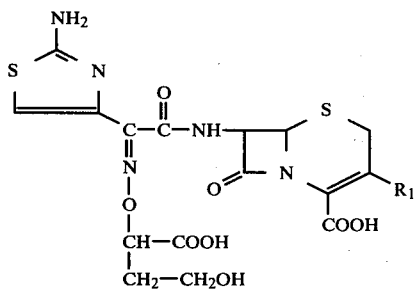

wherein R₁ has the above definition, which compounds I'$_C$ may be also obtained optionally by treatment of compounds I$_C$ with a base and then with an acid

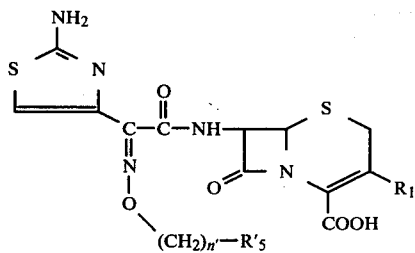

wherein n', R₁ and R₅' have the above definitions,

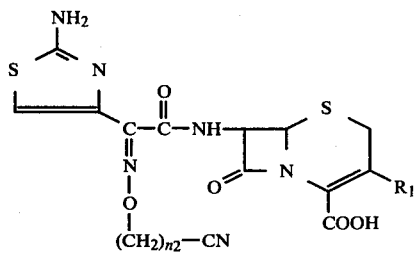

wherein n₂ and R₁ have the above definitions

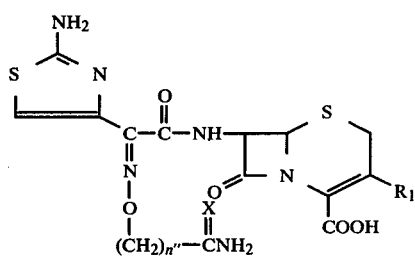

wherein n", R₁ and X have the above definitions,

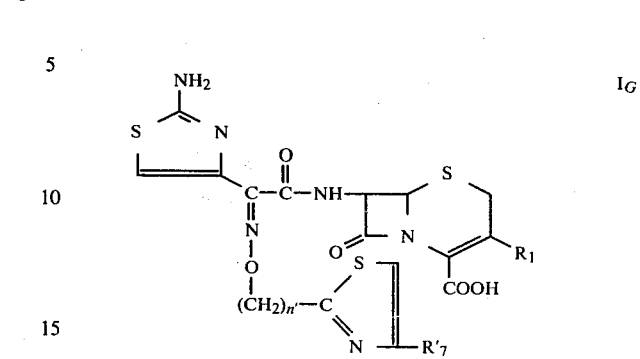

wherein n', R₇' and R₁ have the above definitions,

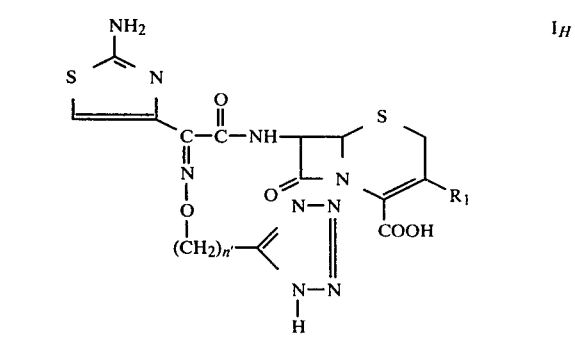

wherein n' and R₁ have the above definitions

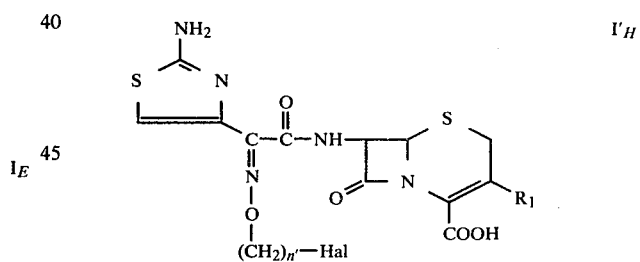

wherein n' Hal and R₁ have the above definitions,

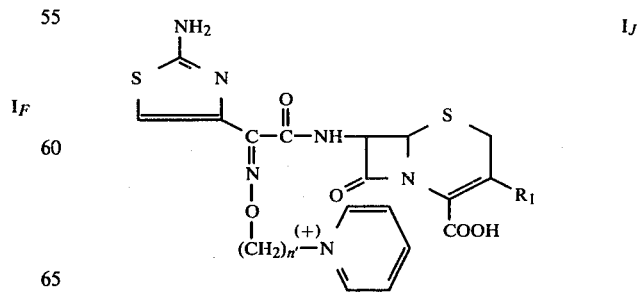

wherein n' and R₁ have the above definitions,

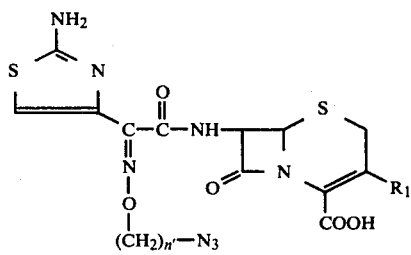

$I_K$ wherein n' and $R_1$ have the above definitions,

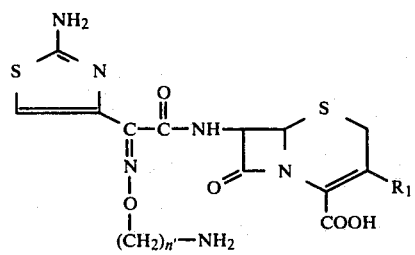

$I'_K$ wherein n' and $R_1$ have the above definitions,

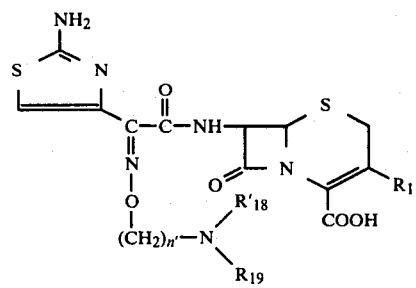

$I_L$ wherein n', $R_1$ and $R_{19}$ have the above definitions and $R_{18}'$ is selected from the group consisting of hydrogen and alkyl of 1 to 4 carbon atoms,

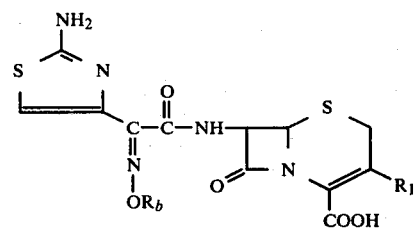

$I''_b$ wherein $R_1$ and $R_b$ have the above definitions and is the compound of formula $I_b$ when A is hydrogen, and

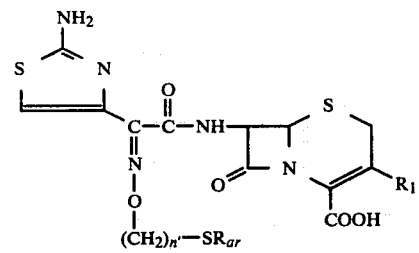

$I_M$ wherein $R_1$, n' and $R_{ar}$ have the above definitions and is the compound of formula $I_a$ when $R_{5a}$ is —$SR_{ar}$. All the said compounds may be salified or esterified, if desired, by known methods.

The groups $R_{16}$ may be any of the normal amine protecting group but is preferably alkyl of 1 to 6 carbon atoms, especially tert.-butyl or tert.-amyl. Examples of other useful groups are acyls of an organic carboxylic acid of aliphatic carboxylic acids, aromatic carboxylic acids, heterocyclic carboxylic acids and carbamoyl groups. Examples of suitable acyl groups are lower alkanoyl such as acetyl, formyl propionyl, butynyl, isobutynyl, valeryl, isovaleryl, oxalyl, succinyl and pivaloyl; lower alkoxycarbonyl and cycloalkoxycarbonyl such as methoxycarbonyl, ethoxycarbonyl, propoxycarbonyl, 1-cyclopropylethoxycarbonyl, isopropoxycarbonyl, butoxycarbonyl, tertbutoxycarbonyl, pentyloxycarbonyl, tert.-pentoxycarbonyl, hexyloxycarbonyl; benzoyl, toluolyl, napthoyl, phthaloyl, mesyl, phenylacetyl, phenylpropionyl; arylalkoxycarbonyl such as benzyloxycarbonyl. The acyl groups may be optionally substituted with at least one halogen such as chlorine, fluorine, bromine and iodine. Examples of such acyls are chloroacetyl, dichloroacetyl, trichloroacetyl, trifluoroacetyl and bromoacetyl.

Other examples of $R_{16}$ groups are lower aralkyl such as benzyl, 4-methoxybenzyl, phenethyl, trityl, 3,4-dimethoxybenzyl and benzhydryl; haloalkyl such as trichloroethyl; chlorobenzoyl, p-nitrobenzoyl, p-tert.-butylbenzoyl, phenoxyacetyl, caprylyl, n-decanoyl, and acryloxyl; methylcarbamoyl, phenylcarbamoyl, naphthylcarbamoyl as well as the corresponding thiocarbamoyls. The above list is not intended to be exhaustive as any amine protecting group known in peptide chemistry, for example, may be used.

Examples of —COOA" groups are esters formed with easily removable groups such as esters of alkyls like butyl, isobutyl, tert.-butyl, pentyl and hexyl esters as well as acetoxymethyl, propionyloxymethyl, butyryloxymethyl, valeryloxymethyl, pivaloyloxymethyl, 2-acetoxyethyl, 2-propionyloxyethyl and 2-butyryloxyethyl esters. Examples of other esters are 2-mesylethyl, 2-iodoethyl, $\beta,\beta,\beta$-trichloro ethyl, vinyl, allyl, ethynyl, propynyl, benzyl, 4-methoxybenzyl, 4-nitrobenzyl, phenethyl, trityl, 3,4-dimethoxybenzyl and diphenylmethyl esters. Other esters are phenyl, 4-chlorophenyl, tolyl and tert.-butylphenyl esters.

Functional acid derivatives of the group $R_3'$

are acid halides such as the acid chloride or acid bromide; symetric or mixed acid anhydride; a ketene or an acylazide. The acylation may also be effected with a haloformate fo example a chloroformate, when $R'_3$ is alkoxy when $R'_3$ is

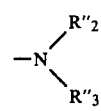

and one of $R_2''$ and $R'''$ is hydrogen, an isocyanate can also be used. The acylation may also be effected with a haloformate when $R_3'$ is

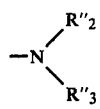

and one of $R_2''$ and $R_3''$ is hydrogen.

With isocyanates of the formula X=C=NH, the acylation of the hydroxy group is effected in an organic solvent such as halogenated hydrocarbon like methylene chloride, a cyclic ether like dioxane or tetrahydrofuran, a nitrile like acetonitrile, a nitrohydrocarbon such as nitromethane or an ester like ethyl acetate. The reaction with an acid halide is preferably effected in the presence of a base such as triethylamine, pyridine, propylene oxide, magnesium oxide, sodium carbonate or calcium carbonate.

The preparation of compounds of formula $III_B$ is effected by reacting a compound of formula II with a compound of the formula

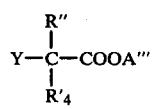

wherein Y may be chlorine, bromine, iodine, a sulfate or sulfonate group such as mesylate or tosylate. The etherification is preferably effected in the presence of a base such as potassium tert.-butylate, sodium hydride, triethylamine or pyridine. The reaction is effected in a solvent such as halogenated hydrocarbons like methylene chloride, cyclic ethers like dioxane or tetrahydrofuran, N,N-disubstituted amides such as dimethylformamide or dimethylsulfoxide. The optional separation of the optical isomers due to the presence of the asymetrical carbon atoms may be effected before or after the etherification.

The products of formula $III_C$ may be effected under the same conditions as that for formula $III_B$. The group $Y_1$ may be the same as Y and may be chlorine, bromine, iodine, a sulfate or a sulfonate such as mesylate or tosylate. The transformation of the compounds of $III_C$ into $III_{C'}$ is effected with an alkali metal base such as dilute potassium hydroxide or sodium hydroxide, sodium carbonate or sodium bicarbonate. The compounds of formulae $III_D$ and $III_E$ may be prepared in the same manner as the compounds of formula $III_B$ or $III_C$. The reaction of compounds of formula IV to obtain products of formula $III_F$ wherein X is S and n'' is an integer from 1 to 4 may be effected with hydrogen sulfide, preferably in the presence of a base such as triethylamine and the reaction is effected in a suitable solvent such as dimethylformamide. The careful hydrolysis of compounds of formula IV to obtain compounds of formula $III_F$ where X is oxygen and n'' is an integer from 2 to 4 is effected in a basic medium, preferably dilute sodium hydroxide.

The reaction of compounds of formula $III_F$ when X is sulfur with a compound of the formula

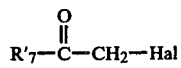

when Hal is chlorine or bromine is preferably effected without catalysts to obtain the corresponding halohydrate of the thiazole which is then treated with a base such as sodium bicarbonate to form the free base of formula $III_G$. The reaction may also be effected with a base catalyst such as sodium bicarbonate.

The compounds of formula $III_H$ may be prepared by reacting the compound of formula IV with an azide such as sodium azide but other alkali metal azides such as potassium azide may be used. Also useful are azides of organic amine bases such as the azide of tetramethylguanidine or the azide of triethylamine or an in situ azide of ammonium such as by the reaction of sodium azide and ammonium chloride. The said reactions are preferably effected in dimethylformamide but ethanol is equally useful.

The reaction of a compound of formula V with pyridine or a compound of the formula $R_{18}$—NH—$R_{19}$ is preferably effected in dimethylformamide. The preferred compounds of formula V are those where Hal is bromine or iodine but also useful are those where Hal is chlorine. The group of $R_{18}$ which is easily removable by acid hydrolysis or hydrogenolysis is preferably trityl but other appropriate known protecting groups are useful.

The reaction of a compound of formula V with an azide to form a compound of formula $III_K$ is effected under the same conditions as the reaction of a compound of formula IV with an azide. The reducing agent used to obtain compounds of formula $III_{K'}$ is preferably hydrogen sulfide in the presence of triethylamine in a solvent such as dimethylformamide in which triethylammonium sulfohydrate is formed in situ. However, other methods of specific reduction such as with alkaline sulfohydrates (sodium, potassium or ammonium) or stannous chloride may be used.

The reaction of a compound of formula V with imidazole, morpholine or N-alkyl-piperazine is preferably effected in the presence of a hydrogen halide receptor such an organic base like triethylamine. However, inorganic bases such as sodium carbonate, sodium bicarbonate or other alkali metal carbonate or bicarbonates may be used. A salt of the compound of formula V such as the diethylamine salt may also be used. The reaction may also be effected in the presence of a quaternary ammonium salt such as methyltricaprylammonium chloride.

The reaction of a compound of formula V with a compound of the formula $R_{ar}$—SH is also preferably effected in the presence of a hydrogen halide receptor such as organic base like triethylamine. However, inorganic bases such as sodium carbonate, sodium bicarbonate or other alkali metal carbonate or bicarbonate may be used. A salt of the compound of formula V such as the diethylamine salt may also be used. The reaction may also be effected in the presence of a quaternary ammonium salt such as methyltricaprylammonium chloride. The reaction may also be effected with an alkali metal derivative of the compound $R_{ar}$—SH such as the lithium derivative and the reaction is preferably effected in the presence of a catalyst such as alkali metal halide like lithium iodide.

The transformation of compounds of formulae $III_A$ to $III_M$ and V into compounds of formulae $I_A$ to $I_M$ is effected to remove the $R_{16}$ protective groups, the group A'' when it is not hydrogen, as well as the groups A''', $A_1$ and $R_{18}$. The removal of the $R_{16}$ group may be effected by acid or basic hydrolysis or with hydrazine. Acid hydrolysis is preferred for removing $R_{16}$ when it is an alkoxycarbonyl or cycloalkoxycarbonyl optionally substituted such as tert.-pentyloxycarbonyl or tert.-butoxycarbonyl or optionally substituted aralkoxycarbonyl such as benzyloxycarbonyl, trityl, tert.-butyl or 4-methoxybenzyl. The acid for the acid hydrolysis may be hydrochloric acid, benzene sulfonic acid, p-toluene sulfonic acid, formic acid or trifluoroacetic acid but other mineral or organic acids may be used.

The basic hydrolysis is preferably used to remove acyl protective groups such as trifluoroacetyl. The preferred bases are mineral bases such as alkali metal hydroxides like sodium hydroxide or potassium hydroxide, magnesium hydroxide, barium hydroxide or alkali metal carbonates or bicarbonates such as sodium carbonate, sodium bicarbonate, potassium carbonate and potassium bicarbonate. Also useful are sodium acetate or potassium acetate or other bases.

The hydrolysis with hydrazine is preferably used to remove protective groups such as phthaloyl. The zinc-acetic acid system may also be used to remove $R_{16}$ groups such as trichloroethyl.

The benzhydryl and benzyloxycarbonyl groups are preprably removed with hydrogen in the presence of a catalyst. Chloroacetyl is preferably removed with thiourea in a neutral or acid medium by the reaction of Masaki[J.A.C.S., Vol. 90 (1968), p. 4508]. Other known ways may be used to remove the amine protecting group.

The preferred protecting groups are formyl, acetyl, ethoxycarbonyl, mesyl, trifluoroacetyl, chloroacetyl, and trityl. The preferred acids are formic acid and trifluoroacetic acid.

Depending on the substituents of the R groups on the oxyimino group, certain protective groups can not be used. For example, when R is acetyl or acyl, $R_{16}$ can not be an acyl radical since the removal of the $R_{16}$ groups would risk the removal of the R group.

The removal of the A" group when it is other than hydrogen as well as the removal of A''', $A_1$ and $R_1'''$, is effected under the same conditions described previously for the removal of $R_{16}$. The hydrolysis may be effected under acidic or basic conditions and acid hydrolysis is preferably used for the removal of optionally substituted alkyl and aralkyl groups. The acid is preferably hydrochloric acid, formic acid, trifluoroacetic acid or p-toluene sulfonic acid. The other values for A''', $R_1'''$, A" and $A_1$ can be removed by known processes. The process is preferably effected under moderate conditions such as at room temperature or with slight heating.

Naturally, when $R_{16}$ and A", for example, are of different types of groups to be removed, the products of formula III may be treated with more than one of the agents recited above.

The compounds of formula $I_C$ are converted into the compounds of formula $I_{C'}$ by classical methods. For example, the base to be used is the same as that used to change the compound of formula $III_C$ into a compound of formula $III_{C'}$ such as dilute sodium hydroxide or potassium hydroxide or sodium carbonate or calcium carbonate.

In the preceding reactions as well as in the reactions discussed infra, a portion of the products obtained are the ceph-2-eme-products and those can be converted by known procedures from $\Delta_2$ products to $\Delta_3$ products. For example, the product containing some $\Delta_2$ product is oxidized to obtain the corresponding sulfoxide such as with a peracid like m-chloroperbenzoic acid. The passage from the $\Delta_2$ sulfoxide to $\Delta_3$ sulfoxide is effected in the presence of water or a hydroxylated solvent and the reduction of the $\Delta_3$ sulfoxide is effected in the presence of an acid halide or phosphorus trichloride. The transformation of $\Delta_2$ products to $\Delta_3$ products is described in U.S. Pat. No. 3,705,897, German patent No. 1,937,016, Kaiser et al [J. Org., Vol. 35, (1970), p. 2430] and Spry et al [J. Org., Vol. 40 (1975), p. 2411].

The products of formula I may be salified by known methods by treating the acids or a solvate thereof (such as ethanol solvate) or a hydrate thereof with a mineral base such as sodium hydroxide, potassium hydroxide, sodium bicarbonate, potassium bicarbonate, sodium carbonate or potassium carbonate or with salts of organic acid or mineral acid such as trisodiumphosphate.

Examples of salts of organic acids are sodium salts of saturated or unsaturated aliphatic carboxylic acids of 1 to 18 carbon atoms, preferably 2 to 10 carbon atoms, and the aliphatic group may be interrupted with at least one heteroatom such as oxygen or sulfur or substituted with aryl radicals such as phenyl, thienyl or furyl or with at least one hydroxyl or with at least one halogen such as fluorine, bromine or chlorine, preferably chlorine, or at least one carboxylic group or lower alkoxy carbonyl, preferably methoxy, ethoxy or propoxy or at least one aryloxy, preferably phenoxy. One can also use as the salts of organic acid the sufficiently soluble aromatic acids such as substituted benzoic acids where the preferred substituent is lower alkyl. Lower alkyl is intended to mean 1 to 6 carbon atoms in the description.

Examples of specific organic acids which are useful in their salt form are formic acid, acetic acid, acrylic acid, butyric acid, adipic acid, isobutyric acid, n-caproic acid, isocaproic acid, chloropropionic acid, crotonic acid, phenylacetic acid, 2-thienylacetic acid, 3-thienylacetic acid, 4-ethylphenylacetic acid, glutaric acid, monoethyl adipate, hexanoic acid, heptanoic acids, decanoic acids, oleic acid, stearic acid, palmitic acid, 3-hydroxypropionic acid, 3-methoxypropionic acid, 3-methylthiobutyric acid, 4-chlorobutyric acid, 4-phenylbutyric acid, 3-phenoxybutyric acid, 4-ethylbenzoic acid and 1-propylbenzoic acid. Especially preferred are sodium acetate, sodium 2-ethylhexanoate and sodium diethylacetate.

The salification may be effected with an organic base such as triethylamine, diethylamine, trimethylamine, propylamine, N,N-dimethylethanolamine, tris(hydroxymethyl) aminomethane as well as arginine, lysine, methylamine, ethanolamine pyridine, picoline, dicyclohexylamine, procaine, histidine, N-methylglucamine, morpholine and benzylamine.

The salification is preferably effected in at least one solvent such as water, ether, methanol, ethanol or acetone. The salts may be in amorphous or crystalline form depending on the reaction conditions. The crystalline salts are preferably formed by reacting the free acids of formula I with the salts of the above aliphatic carboxylic acids, especially sodium acetate.

The esterification of the compounds of formula I may be effected by classical methods such as reacting the acid of formula I with a derivative of the formula Z—$R_{20}$ wherein Z is related from the group consisting of —OH and halogen such as chlorine, bromine, iodine and fluorine and $R_{20}$ is the desired ester moiety as indicated above.

Another process of the invention for the preparation of compounds of formula I' comprises reacting the syn isomer of a compound of the formula

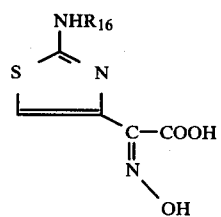

VI wherein R$_{16}$ is a group easily removable by acid hydrolysis or hydrogenolysis with (a) either a functional derivative of a radical

wherein X is oxygen or sulfur and R$_3'$ is selected from the group consisting of alkyl and alkoxy of 1 to 4 carbon atoms, phenyl and

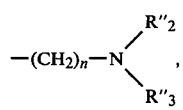

n is an integer from 0 to 4, R$_2''$ and R$_3''$ are selected from the group consisting of hydrogen and alkyl of 1 to 4 carbon atoms with the proviso that at least one is alkyl when n is 0 and R$_2''$ and R$_3''$ taken together with the nitrogen atom form a group selected from the group consisting of piperidino, morpholino and phthalimido to obtain the syn isomer of a compound of the formula

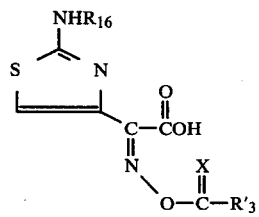

VI$_A$ or (b) with a compound of the formula X═C═NH wherein X is oxygen or sulfur to obtain the syn isomer of a compound of the formula

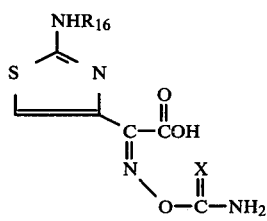

VI'$_A$ or (c) with a compound of the formula

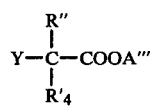

wherein R″ is hydrogen or alkyl of 1 to 4 carbon atoms, Y is halogen, sulfate or sulfonate, R$_4'$ is phenyl or nitrile and A‴ is a protective group easily removed by acid hydrolysis or hydrogenolysis to obtain the syn isomer of a compound of the formula

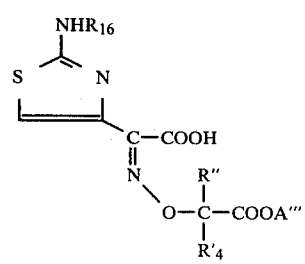

VI$_B$ or (d) with a compound of the formula

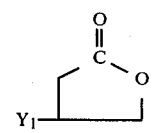

wherein Y$_1$ is the same as Y to obtain the syn isomer of a compound of the formula

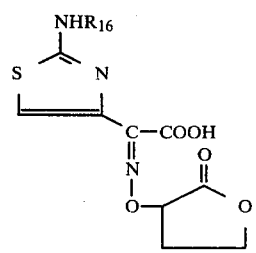

VI$_C$ or (e) with a compound of the formula Y$_2$—(CH$_2$)$_{n'}$—R$_5'$ wherein Y$_2$ is the same as Y, n′ is an integer from 1 to 4 and R$_5'$ is selected from the group consisting of acyl of an alkanoic acid of 2 to 4 carbon atoms, alkoxy of 1 to 4 carbon atoms and alkylthio of 1 to 4 carbon atoms whose sulfur atom can be oxidized to the sulfoxide or sulfonyl form to obtain the syn isomer of a compound of the formula

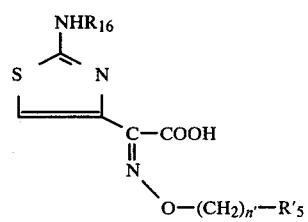

VI$_D$ or (f) a compound of formula VI may be reacted with a compound of the formula Y$_3$—(CH$_2$)$_{n_2}$—CN wherein n$_2$ is an integer from 2 to 4 and Y$_3$ is the same as Y to obtain the syn isomer of a compound of the formula

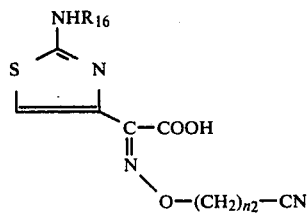

The syn isomer of compound of the formula

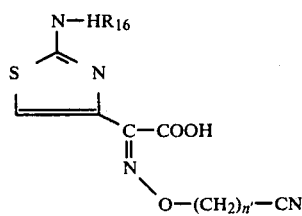

wherein n' is 2 to 4 may be reacted with hydrogen sulfide or when n' is other than 1 by hydrolysis in the presence of a base to obtain the syn isomer of a compound of the formula

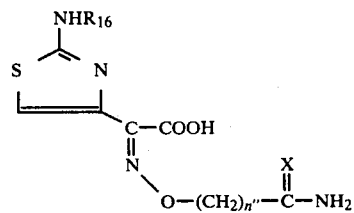

wherein X is oxygen or sulfur and n″ is a integer from 1 to 4 when X is sulfur and n″ is other than 1 when X is oxygen and optionally treating a compound of formula $VI_F$ when X is sulfur with a compound of the formula

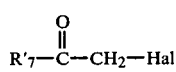

wherein $R_7'$ is methyl or amino and Hal is a halogen to obtain the syn isomer of a compound of the formula

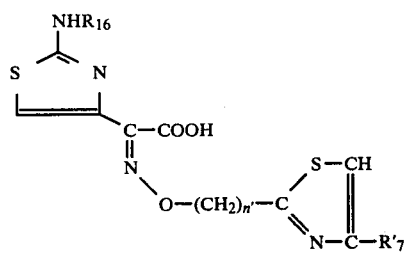

The compound of formula VII may also be reacted with an azide to obtain the syn isomer of a compound of the formula

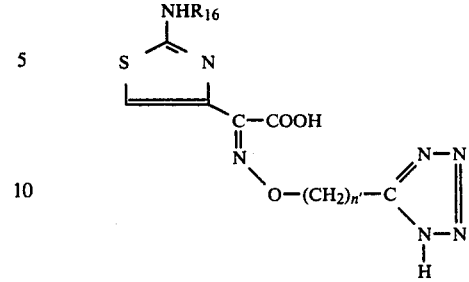

and the syn isomer of a compound of the formula

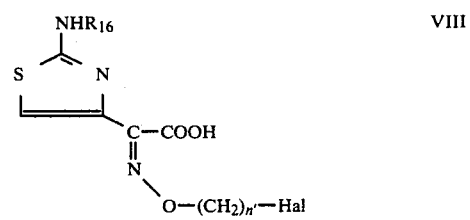

wherein Hal is halogen and n' has the above definition may be reacted with (a) pyridine to obtain the syn isomer of a compound of the formula

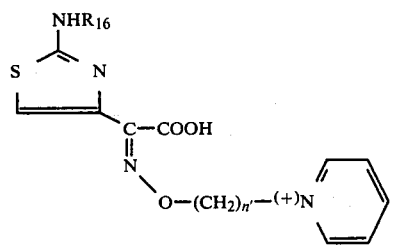

or (b) with an azide to obtain the syn isomer of a compound of the formula

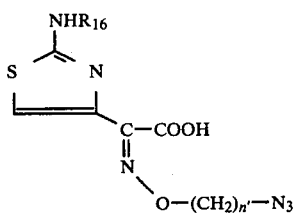

or (c) with a derivative of an amine of the formula $R_{18}$—NH—$R_{19}$ wherein $R_{18}$ is alkyl of 1 to 4 carbon atoms or a group easily removable by acid hydrolysis or hydrogenolysis and $R_{19}$ is hydrogen or alkyl of 1 to 4 carbon atoms and $R_{18}$ and $R_{19}$ together are phthalimido to obtain the syn isomer of a compound of the formula

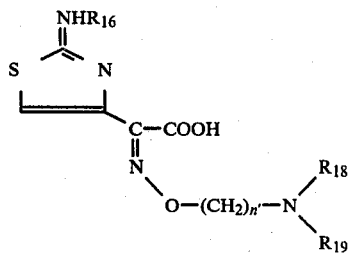
VI$_L$ or (d) with imidazole, morpholine or N-alkyl-piperazine to obtain the syn isomer of a compound of the formula

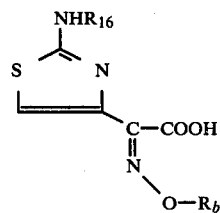
VI'$_L$ wherein R$_b$ has the above definition or (e) with a compound of the formula R$_{ar}$—SH wherein R$_{ar}$ has the above definition to obtain the syn isomer of a compound of the formula

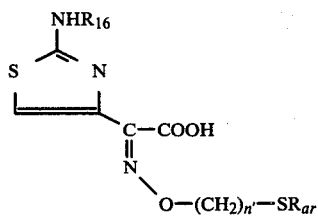
VI$_M$

The products of formulae VI$_A$, VI$_A$', VI$_B$, VI$_C$, VI$_D$, VI$_E$, VI$_F$, VI$_G$, VI$_H$, VIII, VI$_J$, VI$_K$, VI$_L$, VI$_L$' and VI$_M$ or acid derivatives thereof are then reacted with a compound of the formula

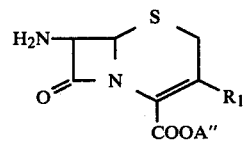
IX wherein R$_1$ has the above definition and A" is hydrogen or a group easily removed by said hydrolysis or hydrogenolysis to obtain the corresponding respective compounds of formulae III$_A$, III$_A$', III$_B$, III$_C$, III$_D$, III$_E$, III$_F$, III$_G$, III$_H$, V, III$_J$, III$_K$, III$_L$, III$_L$' and III$_M$ and the product of formula III$_C$ can be reacted with an alkaline base to form a compound of formula III$_C$' and all the said products can then be transformed into the compounds of formula I'.

The preparation of compounds of formula VI$_A$ from compounds of formula VI may be effected under the same conditions as those for changing a compound of formula II to a compound of formula III$_A$ and the preparation of compounds of formula VI$_A$' from a compound of formula VI is effected in the same fashion as those for converting a compound of formula II into a compound of formula III$_A$'. The same is true for the following compounds.

The reaction of a compound of formula VIII with imidazole, morpholine or N-alkyl-piperazine is effected under the same conditions as the reaction of the said compounds with a compound of formula V. The reaction of a compound of formula VIII with R$_{ar}$—SH is effected under the same conditions as the said compound with a compound of formula V.

In a preferred method of the process, the compound of formula IX is reacted with an acid functional derivative of a product of formulae VI$_A$ to VI$_L$, VI$_L$', VI$_M$ and VIII. The functional derivative may be an acid halide, symmetrical or mixed acid anhydride, an amide or an active ester. An example of mixed anhydride is that formed with isobutyl chloroformate and the acid halide may be the acid chloride or the acid bromide. An example of an active ester is that formed with 2,4-dinitrophenol or with 1-hydroxy-benzo-1-triazole. Also useful are the acid azide or acid amide. The acid anhydride may be formed in situ by reaction with N,N'-disubstituted carbodiimides such as N,N-dicyclohexylcarbodiimide.

The acylation of the compound of formula IX is preferably effected in an organic solvent such as methylene chloride but other solvents such as tetrahydrofuran, chloroform or dimethylformamide may be used. When the acid halide or mixed anhydride formed with isobutyl chloroformate are used, the reaction is preferably effected in the presence of a base such as sodium hydroxide, potassium hydroxide, sodium carbonate, potassium carbonate, sodium bicarbonate, potassium bicarbonate, sodium acetate, pyridine, triethylamine, morpholine or N-methyl-morpholine. The reaction is generally effected at room temperature or below.

The transformation of the products of formulae III$_A$ to III$_L$, III$_L$' III$_M$ and V into compounds of formula I' may be effected under the conditions described above. In an especially preferred mode of the process, R$_{16}$ is selected from the group consisting of trityl, chloroacetyl, tert.-pentyloxycarbonyl, tert.-butoxycarbonyl and benzyloxycarbonyl.

The compounds of formula VIII may be prepared by reacting the syn isomer of a compound of the formula

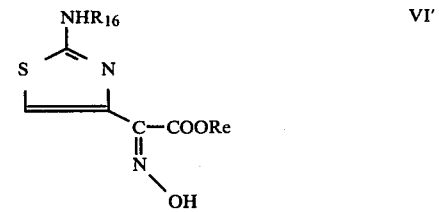
VI' wherein R$_{16}$ is an amino protecting group as indicated above and Re is selected from the group consisting of hydrogen and alkyl of 1 to 4 carbon atoms with a compound of the formula Hal—(CH$_2$)$_{n'}$—Hal wherein n' is an integer from 1 to 4 and Hal is a halogen to obtain the syn isomer of a compound of the formula

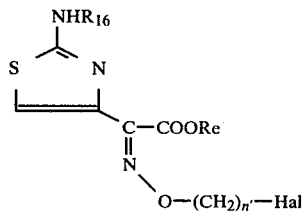

wherein R₁₆, Re, n' and Hal have the above definitions and when Re is alkyl of 1 to 4 carbon atoms, the product of formula VI″ is treated with a base and then an acid.

The reaction of the compounds of formula VI' with a compound of formula: Hal—(CH₂)ₙHal wherein Hal is preferably bromine or iodine preferably effected in the presence of a basic hydrogen halide receptor such as a mineral base like sodium carbonate, sodium bicarbonate, potassium carbonate or potassium bicarbonate but organic amine bases may also be used. The compounds of VI″ wherein Re is alkyl of 1 to 4 carbon atoms may be saponified by known means such as by treatment with a base such as sodium hydroxide potassium hydroxide or baryta followed by treatment with an acid such as dilute hydrochloric acid, acetic acid or formic acid.

The antibiotic compositions of the invention are comprised of an antibiotically effective amount of at least one compound of formula I' and an inert pharmaceutical carrier. The compositions may be in the form of tablets, dragees, gelules, granules, suppositories, injectable solutions or suspensions, creams, pomades, gels, etc. prepared in the usual fashion.

These compositions can also be presented in the form of a powder intended to be dissolved extemporaneously in an appropriate vehicle, for example apyrogenetic sterile water.

Examples of suitable excipients or pharmaceutical carriers are talc, arabic gum, lactose, starch, magnesium stearate, cacao butter, aqueous or non-aqueous vehicles, fatty bodies of vegetable or animal origin, paraffinic derivatives, glycols, preservatives, diverse wetting agents, dispersants and emulsifiers. The compositions of the invention and particularly those containing the compounds of formula I in the syn form possess very good antibiotic activity against gram positive bacteria such as staphylococcus, streptococcus, particularly penicillin resistant staphylococcus as well as against gram negative bacteria such as coliform bacteria, Klebsiella, Salmonella and Proteus.

The compositions are therefore useful in the treatment of germ sensitive infections and particularly those of staphylococcia such as staphylococcal septicemia, staphylococcia malignant on the face or skin, pyodermatitis, septic or suppurantes sores, anthrax, phlegmons, eresipels, acute primitive or post-grip staphylococcia, bronchopneumonia or pulmonary suppurations. They are equally useful for the treatment of collibacillosis and associated infections, infections of Proteus, Klebsiella and Salmonella and other infections caused by gram negative bacteria.

Among the preferred compositions of the invention are those having compounds of formula I' wherein R₁₂ is acyl selected from the group consisting of acetyl, butyryl and propionyl or a heterocyclic selected from the group consisting of 1,2,3-thiadiazolyl, 1,2,5-thiadiazolyl, 1,3,4-thiadiazolyl, 1,2,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl, the said heterocycles being optionally substituted with at least one substituent selected from the group consisting of methyl, ethyl, propyl, isopropyl, methoxy, ethoxy, propoxy, isopropoxy, amino-hydroxycarbonylmethyl, dimethylaminoethyl and diethylaminoethyl.

Among the preferred compositions of the invention are those having products of formula I' in which R₁₂ is selected from the group formed by the acetyl, 1-methyl-tetrazolyl, 2-methyl-1,3,4,-thiadiazolyl, 3-methyl 1,2,4-thiadiazol-5-yl, 3-methoxy-1,2,4-thiadiazolyl, 1,3,4-thiadiazol-5-yl, 2-amino 1,3,4-thiadiazol-5-yl, 3-hydroxycarbonylmethyl 1,2,4-thiadiazol-5-yl, 5 methoxy 1,2,4-thiadiazol-3-yl, 4-methyl 5-hydroxycarbonylmethyl 1,3-thiazol-3-yl and /1-dimethylaminoethyl 1,2,3-4-tetrazol-5-yl radicals.

Also preferred are those compositions wherein R is

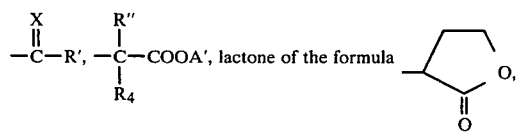

or —(CH₂)ₙ—R₅, X is oxygen, R' is alkyl of 1 to 4 carbon atoms, phenyl or

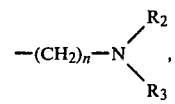

n is 0 or 1, R₂ and R₃ have the above definitions, A' and R″ are hydrogen, R₄ is phenyl or hydroxyethyl, n' is 1 or 2, R₅ is

where R₆ and R₇ have the above definitions or

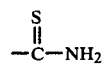

or acetyl or 1,2,3,4-tetrazol-5-yl, R₁ is acetoxymethyl, alkyl of 1 to 5 carbon atoms or —CH₂—S—R₁₂ and R₁₂ is 2-methyl-1,3,4-thiadiazolyl or 1-methyl-tetrazolyl and A is hydrogen, alkali metal, alkaline earth metal, magnesium, —NH₄ or a non-toxic, pharmaceutically acceptable organic amine.

Especially preferred compositions are those wherein R is selected from the group consisting of acetyl, benzoyl, phthalimidoacetyl, N,N-dimethylcarbamoyl, α-carboxyphenylmethyl, 2-oxo-3-tetrahydropyranyl, 1,4-dihydroxy 1-oxo-2-butyl, phthalimidomethyl, aminoethyl, tetrazol-5-yl methyl, 2-amino-2-thioxoethyl and 2-oxo-propyl, R₁ is selected from the group consisting of methyl, acetoxymethyl, 2-methyl-1,3,4-thiadiazol-5-yl-thiomethyl and 1-methyltetrazolyl-thiomethyl and A is hydrogen or sodium especially those wherein R is selected from the group consisting of acetyl, benzoyl, phthalimidoacetyl, 5-tetrazolyl, aminoethyl and α-carboxyphenylmethyl and R₁ is selected from the group consisting of acetoxymethyl, 2-methyl-1,3,4-thiadiazol-5-yl-thiomethyl and 1-methyl-tetrazol-5-yl-thiomethyl.

Especially prefered compositions are those having products of formule $I_a$ in which $R_{5a}$ represents a bromine or iodine atom or a phenylthio, 2-pyridinylthio, 2-amino 1,3,4-thiadiazol-5-yl thio, 1-methyl 1H-tetrazol-5-yl thio, 2-aminophenyl thio, 5-nitro 2-pyridinyl thio or 3-cyano 6-methyl 2-pyridinyl thio group.

Especially preferred are the compositions containing as the active ingredient a member of the group consisting of the syn isomer of 3-acetoxymethyl-7-[2-(2-amino-4-thiazolyl-2-(2-aminoethoxyimino)-acetamido]-ceph-3-eme-4-carboxylic acid, the syn isomer of 3-acetoxymethyl-7-[2-(2-amino-4-thiazolyl)-2-(2-bromoethoxyimino)-acetamido]-ceph-3-eme-4-carboxylic acid, the syn isomer of 3-acetoxymethyl-7-[2-(2-iodoethoxyimino)-acetamido]-ceph-3-eme-4-carboxylic acid and their alkali metal, alkaline earth metal, magnesium, ammonium and organic amine salts and their easily cleaved esters, pharmaceutically acceptable.

The novel method of the invention for combatting bacterial infections in warm-blooded animals, including humans, comprises administering to warm-blooded animals an antibacterially effective amount of at least one compound of formula I'. The compounds may be administered orally, rectally, parenterally or locally by topical application to the skin or mucous. The usual daily dose is 5 to 8.0 mg/kg depending on the specific compound and the method of administration. The compositions are also useful for sterilizing medical instruments.

The novel intermediates of the invention are syn isomers of compounds selected from the group consisting of formulae

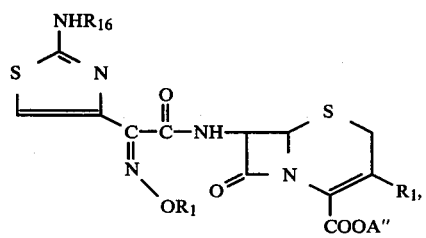   A

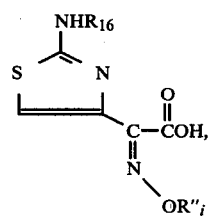   B

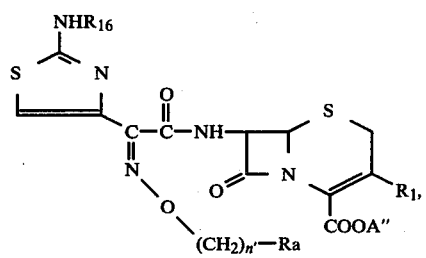   XII

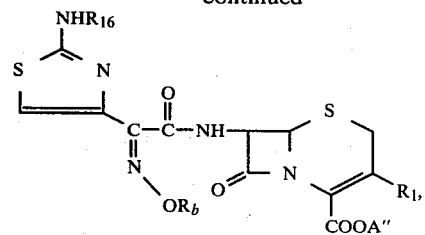   III'$_L$

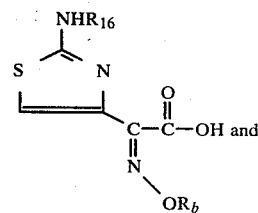   VI'$_L$

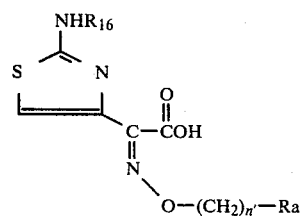   XIII wherein $R_{16}$, $R_1$ and $A''$ have the above definitions, $R_i$ is selected from the group consisting of

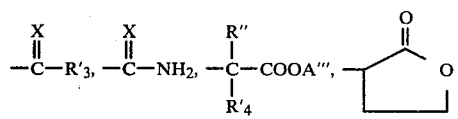

$-(CH_2)_{n'}-R_5'$, $-(CH_2)_{n2}-CN$,

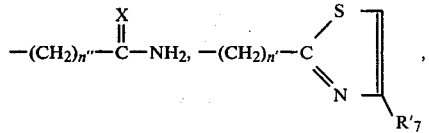

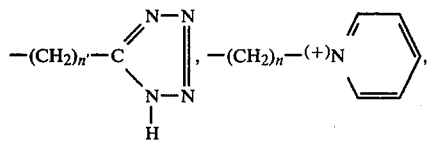

$-(CH_2)_{n'}-N_3$ and

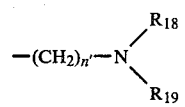

wherein $R_3'$, $X$, $R''$, $R_4'$, $A'''$, $n'$, $R_5'$, $n_2$, $n''$, $R_7'$, $R_{18}$ and $R_{19}$ are as defined hereinbefore, with the proviso that $R_{16}$ can not be chloroacetyl in formula A when $R_i$ is

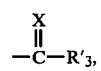

in which R₃' is methyl, and R₁ is

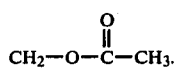

R'' is selected from the group consisting of

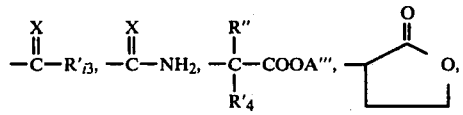

—(CH₂)ₙ'—R₅', —(CH₂)ₙ₂—CN,

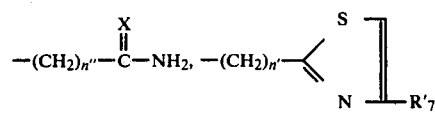

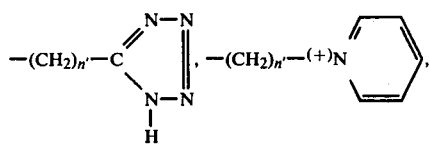

—(CH₂)ₙ'—N₃ and

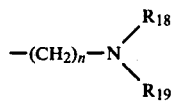

and R$_{i3}$' is the same as R₃' except for methyl.

Particularly preferred are the compounds of formula XII having the formula

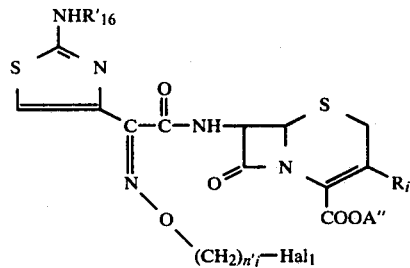

wherein R₁₆' is trityl or chloroacetyl, n$_i$' is 1 or 2, Hal₁, is bromine or iodine, A'' is hydrogen or an easily removable ester and R$_i$ is hydrogen, acetoxy, carbamoyloxy, 1-methyltetrazol-5-yl or 2-methyl-1,3,4-thiadiazol-5-yl and the compounds of formula XIII having the formula

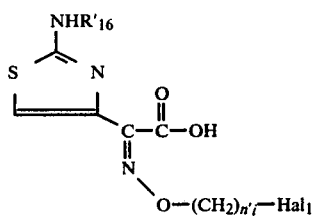

wherein R₁₆', n$_i$' and Hal₁ have the above definitions.

The starting compounds of formula II may be prepared by reacting a compound of the formula

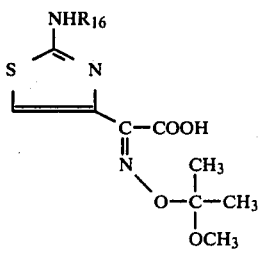

or an acid derivative thereof such as a symetrical acid anhydride with a compound of the formula

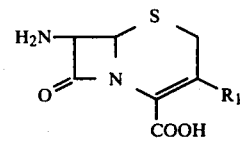

to obtain a compound of the formula

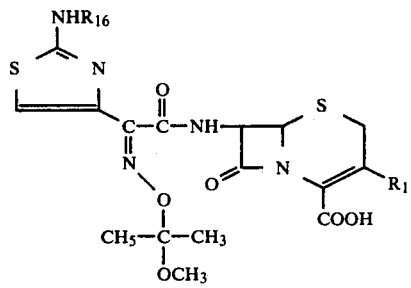

which may be treated with an aqueous mineral acid such as dilute hydrochloric acid to obtain the corresponding compound of formula II.

The compounds of formula C may be prepared by reacting a compound described in Belgium Patent No. 850,662 of the formula

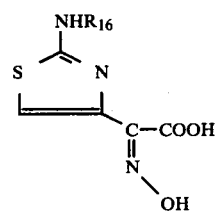

with 2-methoxy-propene.

The starting products of formula V may be prepared by treating a compound of formula VI with 2-methoxy-propene to obtain a compound of the formula

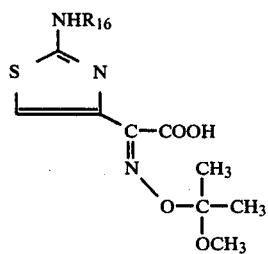

which may be reacted, for example in the form of an acid derivative such as the symetrical anhydride with a compound of formula IX

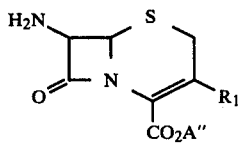

to obtain a compound of the formula

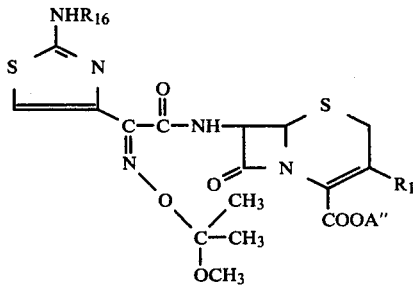

which is reacted with an aqueous mineral acid such as dilute hydrochloric acid to obtain a compound of the formula

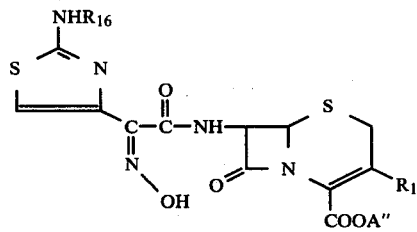

which is then reacted with a compound of the formula Hal—(CH$_2$)$_{n'}$—Hal to obtain the compound of formula V.

The starting compounds of formula III$_K$ used to prepare the compounds of formula I$_K'$ may be prepared by reacting a compound of formula V with an azide such as sodium azide. A compound of formula VIII may also be reacted with an azide and then be condensed with a compound of formula IX.

In the following examples there are described several prefererred embodiments to illustrate the invention. However, it should be understood that the invention is not intended to be limited to the specific embodiments. The 3-acetoxymethyl 7-//2-(2-amino thiazol-4-yl)2-(carbamoyl oxyimino)acetyl/amino/ceph-3-eme carboxylic acid, syn isomer, its salt, with the alkali-metals, the alcaline earth metals, magnesium ammonium and the organic amino bases and its esters with the easily removable groups can also be obtained according to the invention.

EXAMPLE 1 syn isomer of 3-acetoxymethyl-7-[2-(2-amino-4-thiazolyl)-2-acetoxyimino-acetamido]-ceph-3-eme-4-carboxylic acid STEP A: syn isomer of 2-(2-tritylamino-4-thiazolyl)-2-(1-methyl-1-methoxyethoxyimino)-acetic acid A mixture of 12.9 g of the syn isomer of 2-hydroxyimino-2-(2-tritylamino-4-thiazolyl)-acetic acid, 120 ml of methylene chloride and 12 ml of 2-methoxy-propene was stirred at room temperature for 20 minutes and was evaporated to dryness. The residue was stirred with 60 ml of methylene chloride and 12 ml of 2-methoxy-propene for 30 minutes and the mixture was evaporated to dryness to obtain the syn isomer of 2-(2-tritylamino-4-thiazolyl)-2-(1-methyl-1-methoxyethoxyimino)-acetic acid which was used as is for the next step.

STEP B: syn isomer of diethylamine 3-acetoxymethyl-7-[2-(2-tritylamino-4-thiazolyl)-2-(1-methyl-1-methoxyethoxyimino)acetamido]-ceph-3-eme-4-carboxylate 12.5 g of dicyclohexylcarbodiimide were added to a solution of the product of Step A starting from 47.25 g of 2-(2-tritylamino-4-thiazolyl)-2-hydroxyimino-acetic acid in 230 ml of methylene chloride and the mixture was stirred at room temperature for one hour and was vacuum filtered to remove dicyclohexylurea. The filter was rinsed with methylene chloride and a solution of 13.6 g of 7-amino-cephalosporanic acid in 70 ml of methylene chloride and 14 ml of triethylamine was added to the filtrate. The mixture was stirred at room temperature for 2 hours and was washed with 350 ml of N hydrochloric acid. The decanted organic phase was washed with water, dried and evaporated to dryness. The residue was dissolved in 100 ml of ethyl acetate and crystallization was induced. After 30 minutes of crystallization, the mixture was vacuum filtered to recover 5.5 g of the starting material. The filtrate was evaporated to dryness and the residue in 200 ml of isopropyl ether was stirred for 30 minutes and was vacuum filtered. The product was dried to obtain 37.35 g of raw product which was dissolved in 148 ml of ethyl acetate. 5.5 ml of diethylamine was added to the solution which was then vigorously stirred while adding 650 ml of ether thereto. The mixture was vacuum filtered and the recovered product was washed with ether and dried to obtain 26.35 g of the syn isomer of diethylamine 3-acetoxymethyl-7-[2-(2-tritylamino-4-thiazolyl)-2-(1-methyl-1-methoxyethoxyimino)-acetamido]-ceph-3eme-4-carboxylate. The filtrate was evaporated to dryness and the residue was taken up in ether to obtain a second crop of 2.8 g of product identical to the first product, in CCM.

RMN Spectrum (deuterochloroform):

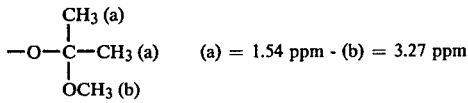

6.78 ppm (thiazolyl ring proton):

STEP C: syn isomer of diethylamine 3-acetoxymethyl-7-[2-(2-tritylamino-4-thiazolyl)-2-hydroxyimino-acetamido]-ceph-3-eme-4-carboxylate A solution of 7.6 of the salt of Step B in 30 ml of acetone and 10 ml of 2 N hydrochloric acid was stirred at room temperature for 40 minutes and after the addition of 20 ml of water, the acetone was evaporated from the mixture at 30° C. under reduced pressure. 25 ml of ethyl acetate were added to the mixture and the decanted aqueous phase was reextracted. The combined organic phases were washed with water, dried and vacuum filtered. 1 ml of diethylamine was added to the filtrate and the mixture was triturated and iced. The mixture was vacuum filtered and the product was washed with ether to obtain 6 g of pure syn isomer of diethylamine 3-acetoxymethyl-7-[2-(2-tritylamino-4-thiazolyl)-2-hydroxyimino)-acetamido]-ceph-3-eme-4-carboxylate.

Analysis: $C_{38}H_{40}O_7N_6S_2$; Calculated: %C 60.30, %H 5.33, %N 11.10, %S 8.47; Found: 60.5, 5.7, 10.9, 8.2.

RMN Spectrum (CDCl$_3$-60 MHz): 6.63 ppm (thiazole proton); 7.33 ppm (trityl proton)

STEP D: syn isomer of 3-acetoxymethyl-7-[2-(2-amino-4-thiazolyl)-2-acetoxyimino-acetamido]-ceph-3-eme-4-carboxylic acid 3 ml of water were added to a solution of 0.756 g of the product of Step C in 1 ml of pyridine and 0.5 ml of acetic acid anhydride was stirred for 30 minutes at room temperature and the pH was adjusted to 1 by addition of 2 N hydrochloric acid. The mixture was vacuum filtered and the product was washed with water and was dried to obtain 0.750 g of raw product. A suspension of 5.20 g of the said product in 1 ml of 2-1 formic acid-water mixture was stirred for 5 minutes at 45° C. in a water bath and after the addition of 0.5 ml of water thereto, the mixture was stirred for 10 minutes at 45° C. 5 ml of ethanol were added to the mixture which was then evaporated to dryness under reduced pressure. The residue was taken up in ether and the mixture was vacuum filtered. The mixture was washed and dried to obtain 0.304 g of impure product containing a desacetyl derivative. The product dissolved in 1 ml of acetic acid anhydride and 2 drops of pyridine and 10 ml of ether were added thereto to precipitate 0.300 g of the syn isomer of 3-acetoxymethy-7-[2-(2-amino-4-thiazolyl)-2-acetoxyimino-acetamido]-ceph-3-eme-4-carboxylic acid.

Analysis: $C_{17}H_{17}O_8N_5S_2$: molecular weight=523.0; Calculated: %C 44.80, %H 3.75, %N 14.70, %S 12.26; Found: 44.6, 3.8, 14.5, 11.7.

RMN: Spectrum) 2.05 ppm: OAc 6.75 ppm: H$_5$ of the thiazole

EXAMPLE 2 syn isomer of 3-acetoxymethyl-7-[2-(2-amino-4-thiazolyl)-2-phthalimidoacetoxyimino-acetamido]-ceph-3-eme-4-carboxylic acid 0.335 g of phthalimidoacetyl chloride were added to a suspension of 0.756 g of the syn isomer of diethylamine 3-acetoxymethyl-7-[2-(2-tritylamino-4-thiazolyl)-2-hydroxyimino-acetamido]-ceph-3-eme-4-carboxylate in 4 ml of methylene chloride and after standing at room temperature for 5 minutes, 10 ml of isopropyl ether was added to the mixture. The mixture was vacuum filtered and the recovered product was empasted with water and was dried to obtain a raw product. The product in 2 ml of a 2-1 formic acid-water mixture was stirred for 20 minutes at 35°–40° C. and 10 ml of water was added thereto. The mixture was vacuum filtered and the product was taken up in ether and vacuum filtered again. The product was dried and dissolved in 4 ml of acetone. The mixture was vaccum dried and was crystallization from 10 ml of ether to obtain 0.280 g of the syn isomer of 3-acetoxymethyl-7-[2-(2-amino-4-thiazolyl)-2-phthalimidoacetoxyiminoacetamido]-ceph-3-eme-4-carboxylic acid.

Analysis: $C_{15}H_{20}O_{10}N_6S_2$; molecular weight=628.6; Calculated: %N 13.77, %S 10.20; Found: 12.5, 10.4.

| U.V. Spectrum (ethanol): | |
|---|---|
| Max. at 217-218 nm | $E_1^1 = 782$ |
| Inflex. at 230 nm | $E_1^1 = 844$ |
| Inflex. at 238 nm | $E_1^1 = 453$ |
| Inflex. at 260 nm | $E_1^1 = 242$ |
| Inflex. at 300 nm | $E_1^1 = 107$ |
| U.V. Spectrum (0.1N HCl-ethanol): | |
| Max. at 217-218 nm | $E_1^1 = 773$ |
| Inflex. at 231 nm | $E_1^1 = 429$ |
| Max at 239 nm | $E_1^1 = 352$ |
| Max. at 258 nm | $E_1^1 = 286$ |
| Inflex. at 280 nm | $E_1^1 = 230$ |

RMN Spectrum (dimethylsulfoxide): 7.18 ppm (thiazole ring)

EXAMPLE 3 syn isomer of 3-acetoxymethyl-7-[2-(2-amino-4-thiazolyl)-2-dimethylaminocarbamoyloxyimino-acetamido]-ceph-3-eme-4-carboxylic acid 0.2 ml of pyridine and 0.2 ml of dimethylcarbamoyl chloride were dissolved in a suspension of 0.756 g of the syn isomer of the diethylamine salt of Step C of Example 1 in 4 ml of methylene chloride and the mixture was washed with water and then with water with a pH of 2. The organic phase was dried and evaporated to dryness. The residue was triturated with ether and the mixture was vacuum filtered to obtain 0.600 g of raw product. The said product in 2 ml of a 2-1 formic acid-water mixture was stirred at 40° C. for 15 minutes and 5 ml of ethanol were added thereto. The mixture was evaporated to dryness and the residue was taken in ethyl acetate to obtain 0.384 g of raw product. The latter was dissolved in 1-1 acetone-methanol mixture and ether was added thereto until floculation occured. The mixture was vacuum filtered and ether was added to the filtrate to obtain 0.213 g of the syn isomer of 3-acetoxymethyl-7-[2-(2-amino-4-thiazolyl)-2-dimethylaminocarbamoyloxyimino-acetamido]-ceph-3-eme-4-carboxylic acid.

Analysis: $C_{18}H_{20}O_8N_6S_2$; molecular weight=511.52; Calculated: %N 16.4; Found: 15.2

I.R. Spectrum (Nujol): 1770 cm$^{-1}$ ($\beta$-lactam); 1724 cm$^{-1}$ (C=O); 1667 cm$^{-1}$ (amide); 1532 cm$^{-1}$ (amide II).

| U.V. Spectrum (ethanol): | | |
|---|---|---|
| Max. at 230 nm | $E_1^1 = 357$ | $\epsilon = 18,300$ |
| Inflex. at 251 nm | $E_1^1 = 261$ | |
| Max. at 300 nm | $E_1^1 = 87$ | |
| U.V. Spectrum (0.1N HCl-ethanol): | | |
| Max. at 256 nm | $E_1^1 = 270$ | $\epsilon = 13,800$ |

| -continued | |
|---|---|
| Inflex. at 280 nm | $E_1^1 = 218$ |

RMN Spectrum (dimethylsulfoxide): 10.3 ppm (thiazole ring)

EXAMPLE 4 syn isomer of trifluoroacetate of
3-acetoxymethyl-7-[2-(2-amino-4-thiazolyl)-2-phthalimidomethyloxyimino-acetamido]ceph-3-eme-4-carboxylic acid STEP A: syn isomer of diphenylmethyl
3-acetoxymethyl-7-[2-(2-tritylamino-4-thiazolyl]-2-(1-methyl-1-methoxyethoxyimino)acetamido-ceph-3-eme-4-carboxylate A mixture of 4.15 g of the diethylamine salts of Step B of Example 1, 40 ml of methylene chloride and 55 ml of 0.1 N hydrochloric acid was stirred at room temperature for 10 minutes and the decanted organic phase was washed twice with 25 ml of water, dried and vacuum filtered. The filter was rinsed with methylene chloride and 15 ml of 8% diazomethane in benzene were added to the filtrate. The mixture was stirred for 15 minutes at room temperature and was then evaporated to dryness under reduced pressure at 30° C. The residue was taken up in isopropyl ether and after efflorescence, the mixture was evaporated to dryness under reduced pressure. The product was taken up in isopropyl ether and the mixture was vacuum filtered. The recovered product was rinsed and dried to obtain 4.41 g of the syn isomer of diphenylmethyl 3-acetoxymethyl-7-[2-(2-tritylamino-4-thiazolyl)-2-(1-methyl-1-methoxyethoxyimino)-acetamido]-ceph-3-eme-4-carboxylate.

RMN Spectrum (CDCl₃-60 MHz):

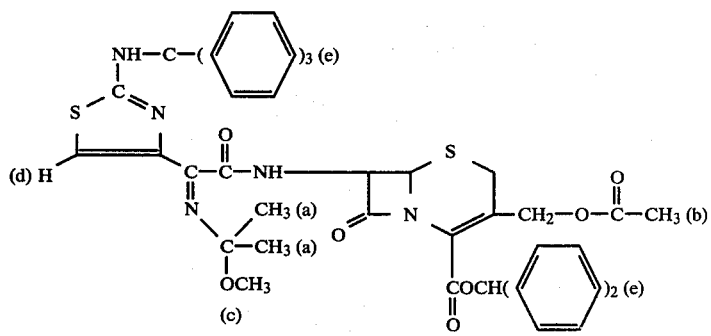

a=1.53 ppm; b=2.01 ppm; c=3.26 ppm; d=6.78 ppm; e=7.33 ppm.

STEP B: syn isomer of diphenylmethyl
3-acetoxymethyl-7-[2-(2-tritylamino-4-thiazolyl)-2-hydroxyimino-acetamido]-ceph-3-eme-4-carboxylate A mixture of 2.775 g of the product of Step A, 14 ml of acetone and 4.5 ml of N hydrochloric acid was stirred for 2 hours at room temperature and the acetone was evaporated under reduced pressure. 20 ml of ethyl acetate were added thereto and the mixture was stirred and decanted. The organic phase was washed 4 times with 10 ml of slightly salted water and the wash waters were extracted with 5 ml of ethyl acetate. The combined organic phases were dried and vacuum filtered and the filter was rinsed with ethyl acetate. The filtrate was evaporated to dryness under reduced pressure and the residue was taken up in ether and was crystallized. Efflorescence occurred and the mixture was vacuum filtered. The product was rinsed with ether and was dried to obtain 1.88 g of the syn isomer of diphenylmethyl 3-acetoxymethyl-7-[2-(2-tritylamino-4-thiazolyl)-2-hydroxyimino-acetamido]-ceph-3-eme-4-carboxylate with a Rf=0.5 (eluant-ether containing 20% acetone).

RMN Spectrum (CDCl₃ 60 MHz): 6.88 ppm (thiazole ring proton); 7.33 ppm (phenyl rings proton)

STEP C: syn isomer of diphenylmethyl
3-acetoxymethyl-7-[2-(2-tritylamino-4-thiazolyl)-2-phthalimidomethyloxyimino-acetamido]-ceph-3-eme-4-carboxylate A mixture of 0.085 g of the product of Step B, 0.12 g of bromomethyl phthalimide, 0.069 g of potassium carbonate and 0.4 ml of dimethylsulfoxide was vigorously stirred for 15 minutes at room temperature and 10 ml of 0.1 N hydrochloric acid were added thereto. The mixture was vacuum filtered and the product was washed with water and dried to obtain 0.124 g of raw product. The latter was dissolved in 1 ml of ethyl acetate and the solution was treated with activated carbon and the solvent was distilled off. The residue was efflorescenced with ether and the mixture was vacuum filtered to obtain 0.075 g of syn isomer of diphenylmethyl 3-acetoxymethyl-7-[2-(2-tritylamino-4-thiazolyl)-2-phthalimidomethyloxyimino-acetamido]-ceph-3-eme-4-carboxylate.

I.R. Spectrum (CHCl₃): absorption at 3408 cm⁻¹ (—NH); at 1782 cm⁻¹ (β-lactam of phthalimide I); at 1730 cm⁻¹ (phthalimide II ester); at 1665 cm⁻¹ (amide); at 1614, 1599 and 1511 cm⁻¹ (C=C, C=N, aromatic amide II); at 1493 cm⁻¹ (NH); 1033 cm⁻¹ (C=N—OR).

RMN Spectrum (deuterochloroform): peaks at 7.03 ppm (trityl-dibenzyl aromatics); at 7.8 ppm (phthalimide); at 6.9 ppm

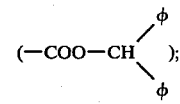

at 3.4 ppm (CH₂S—).

STEP D: syn isomer of trifluoroacetate of 3-acetoxymethyl-7-[2-(2-amino-4-thiazolyl)-2-phthalimidomethyloxyimino-acetamido]-ceph-3-eme-4-carboxylic acid 3 ml of trifluoroacetic acid were added to 0.32 g of the product of Step C and the mixture was vigorously stirred for 10 minutes. The mixture was evaporated to dryness under reduced pressure at 30° C. and 30 ml of isopropyl ether were added thereto. The residue was efflorescenced and was vacuum filtered. The product was rinsed with isopropyl ether to obtain 0.21 g of syn isomer of trifluoroacetate of 3-acetoxymethyl-7-[2-(2-amino-4-thiazolyl)-2-phthaliminomethyloxyiminoacetamido]-ceph-3-eme-4-carboxylic acid.

EXAMPLE 5 syn isomer of sodium 3-acetoxymethyl-7-[2-(2-amino-4-thiazolyl)-2-phthalimidomethyloxyimino-acetamido]-ceph-3-eme-4-carboxylate 0.6 ml of a molar solution of sodium acetate in methanol was added to a solution of 0.21 g of the product of Example 4 in 0.4 ml of methanol and then 2 ml of ethanol were slowly added thereto. The mixture was vacuum filtered and the product was rinsed with ethanol and then with ether to obtain 0.127 g of syn isomer of sodium 3-acetoxymethyl-7-[2-(2-amino-4-thiazolyl)-2-phthalimidomethyloxyimino-acetamido]-ceph-3-eme-4-carboxylate.

| U.V. Spectrum (0.1N HCl in ethanol): | |
|---|---|
| Max. at 217 nm | $\epsilon = 46,500$ |
| Inflex. at 237 nm | $\epsilon = 20,000$ |
| Max. at 252 nm | $\epsilon = 16,300$ |
| Inflex. at 301 nm | $\epsilon = 7,400$ |
| Inflex. at 320 nm | $\epsilon = 5,850$ |

RMN Spectrum (dimethylsulfoxide): peaks at 8.05 ppm (aromatics); at 2 ppm (acetyloxy).

I.R. Spectrum (Nujol): absorption at 1776, 1764, 1724 cm$^{-1}$ (C═O); at 1689 cm$^{-1}$ (amide); and at 1659, 1611, 1545, 1525 and 1511 cm$^{-1}$ (C═C, —C═N, aromatic, amide II, COO$^-$).

EXAMPLE 6 syn isomer of trifluoroacetate of 3-acetoxymethyl-7-[2-(2-amino-4-thiazolyl)-2-(α-carboxyphenylmethoxyimino)-acetamido]ceph-3-eme-4-carboxylic acid STEP A: syn isomer of diethylamine 3-acetoxymethyl-7-[2-(2-tritylamino-4-thiazolyl)-2-(α-tertbutoxycarbonyl-benzyloxyimino)-acetamido]-ceph-3-eme-4-carboxylate A mixture of 1.37 g of the product of Step C of Example 1 in 20 ml of methylene chloride was stirred at room temperature and 20 ml of water were added thereto. Then, 2.8 ml of triethylamine were slowly added thereto and a solution of 4.8 g of tertbutyl α-bromophenylacetate in 5 ml of methylene chloride was added to the resulting emulsion. The mixture was stirred at room temperature for 23 hours and was adjusted to a pH of 1 by addition of 10 ml of 2 N hydrochloric acid. The mixture was extracted with chloroform and the organic phase was washed with water, dried and evaporated to dryness under reduced pressure at 30° C. to obtain 6.1 g of a brown oil. The oil was dissolved in 5 ml of ethyl acetate and 0.25 ml of diethylamine and then 50 ml of isopropyl ether were added thereto. The mixture was vacuum filtered to obtain 1.11 g of the syn isomer of diethylamine 3-acetoxymethyl-7-[2-(2-tritylamino-4-thiazolyl)-2-(α-tertbutoxycarbonyl-benzyloxyimino)acetamido]-ceph-3-eme-4-carboxylate and the mother liquors yielded another 0.1 g of the same product. The combined fractions were dissolved in 5 ml of ethyl acetate and the solution was filtered. The filtrate was evaporated to dryness and the residue was taken up in ether. The mixture was vacuum filtered. The product was rinsed with ether and was then dried at room temperature under reduced pressure to obtain 0.96 g of the desired product which was used as is for the next step.

I.R. Spectrum (CHCl$_3$): absorption at 3372 cm$^{-1}$ (NH and associated); at 1781 cm$^{-1}$ (β-lactam); shoulder at 1738 cm$^{-1}$ (acetyloxy); at 1729 cm$^{-1}$ (C═O ester); at 1681 cm$^{-1}$ (amide); at 1602, 1526 and 1493 cm$^{-1}$ (COO$^-$ and amide II); at 1063 cm$^{-1}$ (C═N—OR).

| U.V. Spectrum (ethanol): | | |
|---|---|---|
| Inflex. at 230 nm | $E_1^1 = 304$ | |
| Inflex. at 260 nm | $E_1^1 = 189$ | |
| Inflex. at 303 nm | $E_1^1 = 60$ | $\epsilon = 9,700$ |
| Max. at 447 nm | $E_1^1 = 8$ | |
| Max. at 515 nm | $E_1^1 = 3$ | |
| U.V. Spectrum (0.1N HCl in ethanol): | | |
| Max. at 267 nm | $E_1^1 = 160$ | $\epsilon = 15,000$ |

RMN Spectrum: peak at 6.8 ppm (thiazole).

STEP B: syn isomer of trifluoroacetate of 3-acetoxymethyl-7-[2-(2-amino-4-thiazolyl)-2-(α-carboxyphenylmethoxyimino)-acetamido]-3-ceph-4-carboxylic acid A mixture of 0.882 g of the product of Step A in 8.9 ml of trifluoroacetic acid was stirred for 10 minutes at room temperature and after dissolution, the mixture was concentrated at 30° C. under reduced pressure to a volume of about 3 ml. The mixture was cooled and the residue was taken up in 30 ml of isopropyl ether. The mixture was stirred at room temperature for 10 minutes and was vacuum filtered and the product was rinsed with isopropyl ether and dried under reduced pressure at 20°–25° C. to obtain 0.512 g of product. The product was taken up in 2 ml of acetone containing 1% of water and the mixture was stirred for 5 minutes at room temperature. The mixture was slowly diluted with 20 ml of ether with stirring and after 10 minutes, the mixture was vacuum filtered. The product was rinsed with ether and dried under reduced pressure at room temperature to obtain 0.443 g of the syn isomer of trifluoroacetate of 3-acetoxymethyl-7-[2-(2-amino-4-thiazolyl)-2-(α-carboxyphenylmethoxyimino)-acetamido]-3-ceph-4-carboxylic acid.

EXAMPLE 7 syn isomer of sodium 3-acetoxymethyl-7-[2-(2-amino-4-thiazolyl)-2-(α-carboxyphenylmethoxyimino)-acetamido]-ceph-3-eme-4-carboxylate 40 mg of activated carbon were added to a solution of 0.421 g of the product of Example 6 in 2.1 ml of methanol and 2.1 ml of 1 M sodium acetate in methanol at room temperature and the mixture was vacuum filtered. The filtrate was concentrated was under reduced pressure at 30° C. to a volume of 1 ml. 10 ml of ethanol were added thereto and the mixture was vacuum filtered. The product was rinsed with ethanol and then with ether and was dried under reduced pressure at room temperature to obtain 0.275 g of the syn isomer of sodium 3-acetoxymethyl-7-[2-(2-amino-4-thiazolyl)-2-(α-carboxyphenylmethoxyimino)-acetamido]-ceph-3-eme-4-carboxylate.

Analysis: $C_{23}H_{19}O_9N_5S_2Na_2$; molecular weight=619.5; Calculated: %C 44.59, %H 3.09, %N 11.3, %S 10.35; Found: 44.8, 3.5, 11.3, 10.2.

| U.V. Spectrum (0.1N HCl in ethanol): | | |
|---|---|---|
| Max. at 260 nm | $E_1^1 = 266$ | $\epsilon = 16,500$ |
| Inflex. at 276 nm | $E_1^1 = 222$ | $\epsilon = 13,700$ |
| Inflex. at 395 nm | $E_1^1 = 8$ | |

I.R. Spectrum (Nujol): absorption at 1761 cm$^{-1}$ (β-lactam); at 1532 cm$^{-1}$ (amide II); at 1027 cm$^{-1}$ (C=N—OR).

EXAMPLE 8 syn isomer of 3-acetoxymethyl-7-[2-(2-amino-4-thiazolyl)-2-(2-oxo-3-tetrahydrofuranyloxyimino)-acetamido]-ceph-3-eme-4-carboxylic acid STEP A: Mixture of syn isomer of Δ$^2$ and Δ$^3$-isomers of diphenylmethyl 3-acetoxymethyl-7-[2-(2-tritylamino-4-thiazolyl)-2-(2-oxo-3-tetrahydrofuranyloxyimino)-acetamido]-ceph-3-eme-4-carboxylate 0.69 of anhydrous potassium carbonate and then 3.2 ml of α-bromo-γ-butyrolacetone were added at room temperature with stirring to a solution of 1.7 g of the product of Example 4 in 8.5 ml of dimethylformamide and the suspension was stirred under an inert atmosphere at room temperature for 45 minutes. The mixture was poured into a mixture of 20 ml of water, 12 ml of N hydrochloric acid and 30 ml of ethyl acetate and the mixture was decanted. The organic phase was washed with aqueous sodium chloride solution until the wash water was neutral and was dried. The solution was evaporated to dryness under reduced pressure at 35° C. to obtain 2.6 g of a clear brown oil which was taken up in isopropyl ether. The mixture was stirred at 40° C. for 5 minutes and the decanted isopropyl ether was treated as before to obtain 2.5 g of dry residue. The latter was treated in the same manner with ethyl ether and the residue was taken up in 20 ml of ether at room temperature with stirring for 15 minutes. The mixture was vacuum filtered and the solids was rinsed with ether and was dried under reduced pressure to obtain 1.513 g of the mixture of syn isomer of Δ$^2$ and Δ$^3$-isomers of diphenylmethyl 3-acetoxymethyl-7-[2-(2-tritylamino-4-thiazolyl)-2-(2-oxo-3-tetrahydrofuranyloxyimino)-acetamido]-ceph-3-eme-4-carboxylate in the form of a yellow amorphous product which was used as is for the next step.

I.R. Spectrum: absorptions at 3395 cm$^{-1}$ (NH); at 1785 cm$^{-1}$ (β-lactam-γ-lactone); at 1744 cm$^{-1}$ (acetyloxy+ester); at 1691 cm$^{-1}$ (amide); at 1655, 1599, 1588, 1515 and 1493 cm$^{-1}$ (C=C, C=N, amide II aromatic).

RMN Spectrum (deuterochloroform): peaks at 6.80 ppm (thiazole).

STEP B: syn isomer of diphenylmethyl 1-oxo-3-acetoxymethy-7-[2-(2-tritylamino-4-thiazolyl)-2-(2-oxo-3-tetrahydrofuranyloxyimino)-acetamido]-ceph-3-eme-4-carboxylate A solution of 0.420 g of m-chloro-perbenzoic acid in 8 ml of methylene chloride was added under an inert atmosphere to a stirred solution of 1.525 g of the product of Step A in 8 ml of methylene chloride cooled on an ice bath to 0° to 5° C. and the mixture was stirred for one hour at that temperature. The mixture was evaporated to dryness under reduced pressure and the residue was taken up in 20 ml of ethyl acetate. The organic phase was washed with aqueous sodium bicarbonate solution and then with aqueous sodium chloride until the wash waters were neutral, dried and evaporated to dryness under reduced pressure at a temperature less than 30° C. The residue was taken up in 10 ml of ether and the mixture was vacuum filtered at room temperature. The product was rinsed with ether to obtain 1.390 g of the syn isomer of diphenylmethyl 1-oxo-3-acetoxymethyl-7-[2-(2-tritylamino-4-thiazolyl)-2-(2-oxo-3-tetrahydrofuranyloxyimino)-acetamido]-ceph-3-eme-4-carboxylate in the form of a yellow product.

I.R. Spectrum (CHCl$_3$): absorption at 3386 cm$^{-1}$ (NH); at 1797 cm$^{-1}$ (C=O of γ-lactone+β-lactam); 1737 and 1691 cm$^{-1}$ (OAc+conjugated ester+amide); at 1634, 1599, 1587, 1523 and 1595 cm$^{-1}$ (C=C, C=N, aromatic, amide II); at 1044, 1035 and 1023 cm$^{-1}$ (possible S+O, oxime ether).

| U.V. Spectrum (ethanol): | | |
|---|---|---|
| Inflex. at 257 nm | $E_1^1 = \approx 196$ | |
| Inflex. at 305 nm | $E_1^1 = \approx 53$ | $\epsilon \approx 5,000$ |
| U.V. Spectrum (0.1N HCl in ethanol): | | |
| max. at 265 nm | $E_1^1 = \approx 200$ | $\epsilon \approx 19,000$ |
| Inflex. at 300 nm | $E_1^1 = \approx 85$ | $\epsilon \approx 8,100$ |

RMN Spectrum (deuterochloroform): peaks at 2 ppm (acetyloxy); at 6.73 and 6.77 ppm (thiazole); at 6.7 ppm

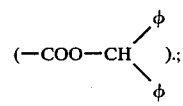

at 7.3 ppm (aromatics)

STEP C: syn isomer of diphenylmethyl 3-acetoxymethyl-7-[2-(2-tritylamino-4-thiazolyl)-2-(2-oxo-3-tetrahydrofuranyloxyimino)-acetamido]-ceph-3-eme-4-carboxylate 0.6 ml of phosphorus trichloride were added over 30 seconds at −20° C. under an inert atmosphere to a solution of 1.328 g of the product of Step B in 6.6 ml of dimethylformamide and the solution was stirred at −20° C. for 5 minutes and was poured into 30 ml of ethyl acetate, 30 ml of saturated sodium bicarbonate solution and 15 g of ice. The mixture was extracted with ethyl acetate and the decanted aqueous phase was extracted again with ethyl acetate. The combined organic phases were washed with aqueous sodium chloride until the wash waters were neutral, dried and distilled to dryness under reduced pressure at less than 40° C. The residue was added to 10 ml of ether and the mixture was vacuum filtered. The product was rinsed and dried at room temperature under reduced pressure to obtain 1.039 g of product which was chromatographed over silica gel. Elution with methylene chloride containing 10% of ether and evaporation of the solvent yielded a residue which was vacuum filtered at room temperature. The product was dried to obtain 0.751 g of the syn isomer of diphenylmethyl 3-acetoxymethyl-7-[2-(2-tritylamino-4-thiazolyl)-2-(2-oxo-3-tetrahydrofuranyloxyimino)-acetamido]-ceph-3-eme-4-carboxylate.

RMN Spectrum (deuterochloroform): peaks at 2 ppm (acetyloxy); at 6.8 ppm (thiazole ring); at 6.9 ppm

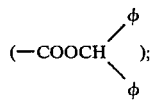

at 7.3 ppm (aromatics).

STEP D: syn isomer of 3-acetoxymethyl-7-[2-(2-amino-4-thiazolyl)-2-(2-oxo-3-tetrahydrofuranyloxyamino)-acetamido]-ceph-3-eme-4-carboxylic acid A mixture of 7.2 ml of trifluoroacetic acid and 0.720 g of the product of Step C was stirred at 20°–25° C. for 10 minutes and the mixture was evaporated to a volume of 2 ml under reduced pressure at less than 30° C. The mixture was cooled in an ice-water bath and was then taken up in 30 ml of isopropyl ether. The mixture was stirred at room temperature for 10 minutes and was then vacuum filtered to obtain 0.483 g of a product. A mixture of the latter product, 0.5 ml of anisol and 4.8 ml of trifluoroacetic acid was stirred 5 minutes at room temperature and the mixture was concentrated to about 1 ml. The mixture was poured into 20 ml of isopropyl ether and was vacuum filtered to obtain 0.472 g of product, 0.458 g of the latter was added to 1.8 ml of 50% aqueous formic acid and the mixture was heated at 50° C. for 10 minutes under an inert atmosphere. The mixture was filtered hot and the filtrate was evaporated to dryness under reduced pressure at less than 30° C. The residue was taken up in 3 ml of water and the mixture was vacuum filtered. The product was rinsed with a very little water and then ether to obtain 0.283 g of the syn isomer of 3-acetoxymethyl-7-[2-(2-amino-4-thiazolyl)-2-(2-oxo-3-tetrahydrofuranyloxyimino)-acetamido]-ceph-3-eme-4-carboxylic acid which was used as is for in next example.

EXAMPLE 9 syn isomer of sodium 3-acetoxymethyl-7-[2-(2-(amino-4-thiazolyl)-2-(2-oxo-3-tetrahydrofuranyloxyimino)-acetamido]-ceph-3-eme-4-carboxylate A solution of 0.283 g of the product of Example 8, 1 ml of 1 M sodium acetate in methanol and 1 ml of methanol was treated with 30 g of activated carbon and the mixture was filtered. The filter was rinsed 3 times with methanol and the filtrate was evaporated under reduced pressure at a temperature less than 30° C. to a volume of 1 ml. The solution was diluted with 10 ml of ethanol at 100° C. and was vacuum filtered. The mixture was rinsed with 100° C. ethanol and then with ether to obtain 0.165 g of the syn isomer of sodium 3-acetoxymethyl-7-[2-(2-amino-4-thiazolyl)-2-(2-oxo-3-tetrahydrofuranyloxyimino)-acetamido]-ceph-3-eme-4-carboxylate.

Analysis: $C_{19}H_{18}O_9N_5S_2Na$; molecular weight=547.5; Calculated: %C 41.68, %H 3.31, %N 12.79, %S 11.72, %Na 4.1; Found: 43.8, 3.5, 11.8, 10.7, 4.2.

| U.V. Spectrum (0.1N HCl in ethanol): | | |
|---|---|---|
| Inflex. at 220 nm | $E_1^1 = 255$ | |
| Max. at 260 nm | $E_1^1 = 302$ | $\epsilon = 16,500$ |

I.R. Spectrum (Nujol): absorption at 1765 cm$^{-1}$ ($\beta$-lactam-$\gamma$-lactone); at 1673 cm$^{-1}$ (amide); at 1611 cm$^{-1}$ (C=C, C=N, COO$^-$); at 1535 cm$^{-1}$ (amide II).

RMN Spectrum (dimethylsulfoxide): peaks at 1.98 ppm (acetyloxy); 6.78 ppm (thiazole ring); at 4.33 ppm (COOCH$_2$).

EXAMPLE 10 syn isomer of disodium 3-acetoxymethyl-7-[2-(2-amino-4-thiazolyl)-2-[1,4-dihydroxy-1-oxo-2-butyloxyimino-acetamido]-ceph-3-eme-4-carboxylate A mixture of 0.257 g of the product of Example 9 and 2.7 ml of 0.0865 M aqueous sodium carbonate was stirred for 4 hours at room temperature and after 16 hours, the mixture was evaporated to dryness under reduced pressure at less than 30° C. The residue was added to 2 ml of methanol and the brown insolubles were filtered off. The filtrate was evaporated to dryness and the residue was taken up in 2.5 ml of ethanol. The mixture was vacuum filtered and the product was rinsed with ethanol and then with ether to obtain 0.226 g of the syn isomer of disodium 3-acetoxymethyl-7-[2-(2-amino-4-thiazolyl)-2-[1,4-dihydroxy-1-oxo-2-butyloxyimino-acetamido]ceph-3-eme-4-carboxylate.

Analysis: $C_{19}H_{19}O_{10}Na_2S_2N_5$; molecular weight=587.5; Calculated: %C 38.84, %H 3.26, %N 11.92, %S 10.91, %Na 7.82; Found: 39.8, 3.7, 10.7, 10.1, 7.6.

| U.V. Spectrum (0.1N HCl in ethanol): | | |
|---|---|---|
| Inflex. at 224 nm | $E_1^1 = 198$ | |
| Max. at 262 nm | $E_1^1 = 225$ | $\epsilon = 15,000$ |

RMN Spectrum (D$_2$O): peak at 7.03 ppm (thiazole ring)

I.R. Spectrum (Nujol): absorption at 1763 cm$^{-1}$ ($\beta$-lactam); at 1667 cm$^{-1}$ (amide); at 1575 cm$^{-1}$ (COO$^-$).

EXAMPLE 11 syn isomer of 3-acetoxymethyl-7-[2-(2-amino-4-thiazolyl)-2-(2-oxo-3-tetrahydrofuranyloxyimino)-acetamido]-ceph-3-eme-4-carboxylic acid STEP A: Diethylamine 3-acetoxymethyl-7-[2-(2-tritylamino-4-thiazolyl)-2-(2-oxo-3-tetrahydrofuranyloxyimino)-acetamido]ceph-3-eme-4-carboxylate 20 ml of water and 2.8 ml of triethylamine were added to the solution of 1.367 g of the product of Step C of Example 1 in 20 ml of methylene chloride and after the addition of 1 ml of α-bromo-γ-butyrolacetone thereto, the mixture was stirred at room temperature for 17 hours. Another 1 ml of α-bromo-γ-butyrolacetone was added thereto and the mixture was stirred for 3 hours, 1.4 ml of triethylamine was added thereto and the mixture was stirred for 5 hours. Then, 1.5 ml of α-bromo-γ-butyrolacetone and 1.4 ml of triethylamine were added thereto and the mixture was stirred for 16 hours. The mixture was acidified with 20 ml of 2 N hydrochloric acid and the decanted organic phase was washed with water until the wash water was neutral. The organic phase was dried and evaporated to dryness under reduced pressure and the residue was added to 10 ml of ethyl acetate. The mixture was vacuum filtered and the filter was rinsed. The filtrate was dried and evaporated to dryness and the residue was added to 10 ml of ethyl acetate. 0.2 ml of diethylamine were slowly added thereto and the mixture was vacuum filtered at room temperature to remove the starting salt. The filter was rinsed in the ethyl acetate and then with ether and the filtrate was evaporated to dryness. The residue was taken up in 2 ml of ethyl acetate and 20 ml of isopropyl ether were added thereto. The mixture was vacuum filtered to obtain 0.500 g of the diethylamine 3-acetoxymethyl-7-[2-(2-tritylamino-4-thiazolyl)-2-(2-oxo-3-tetrahydrofuranyloxyimino)-acetamido]-ceph-3-eme-4-carboxylate.

| U.V. Spectrum (0.1N HCl in ethanol): | | |
|---|---|---|
| max. at 265 nm | $E_1^1 = 179$ | $\epsilon = 15,000$ |

RMN Spectrum (deuterochloroform): peak at 6.76 ppm (thiazole):

STEP B: Trifluoroacetate of syn isomer of 3-acetoxymethyl-7-[2-(2-amino-4-thiazolyl)-2-(2-oxo-3-tetrahydrofuranyloxyimino)-acetamido]-ceph-3-eme-4-carboxylic acid A mixture of 0.5 g of the product of Step A and 5 ml of trifluoroacetic acid was stirred for 15 minutes at room temperature and was then evapoated under reduced pressure to a volume of about 2 ml. 20 ml of isopropyl ether were added thereto all at once and the mixture was stirred at room temperature for 15 minutes and was then vacuum filtered. The product was rinsed 5 times with 2 ml of isopropyl ether and was dried under reduced pressure to obtain the trifluoroacetate of syn isomer of 3-acetoxymethyl-7-[2-(2-amino-4-thiazolyl)-2-(2-oxo-3-tetrahydrofuranyloxyimino)-acetamido]-ceph-3-eme-4-carboxylic acid.

STEP C: syn isomer of 3-acetoxymethyl-7-[2-(2-amino-4-thiazolyl)-2-(2-oxo-3-tetrahydrofuranyloxyimino)-acetamido]-ceph-3-eme-4-carboxylic acid A mixture of the product of Step B, 2 ml of a 1-1 methanol-methylene chloride mixture and 0.5 ml of a 1 M pyridine solution in ethanol was empasted at room temperature for 15 minutes and was diluted by the addition of 8 ml of ether containing 2% ethanol over 2 minutes. The mixture was stirred and vacuum filtered and the recovered product was rinsed with ether and dried under reduced pressure to obtain the syn isomer of 3-acetoxymethyl-7-[2-(2-amino-4-thiazolyl)-2-(2-oxo-3-tetrahydrofuranyloxyimino)-acetamido]-ceph-3-eme-4-carboxylic acid.

EXAMPLE 12 syn isomer of sodium 3-acetoxymethyl-7-[2-(2-amino-4-thiazolyl)-2-(tetrazol-5-yl-methyloxyimino)-acetamido]-ceph-3-eme-4-carboxylate STEP A: syn isomer of cyanomethyl 2-(cyanomethyloxyimino)-2-(2-tritylamino-4-thiazolyl)-acetate A mixture of 12.9 g of the syn isomer of 2-(hydroxyimino)-2-(2-tritylamino-4-thiazolyl)-acetic acid, 60 ml of dry dimethylformamide and 7.6 ml of acetonitrile was stirred under an inert atmosphere until the mass solidified and the mixture stood for 65 hours in a closed atmosphere. The mass was poured into a mixture of 750 ml of water, 130 ml of N hydrochloric acid and 150 ml of ethyl acetate and the mixture was stirred and was vacuum filtered. The filter was rinsed with ethyl acetate and with water and the decanted organic phase was washed with 100 ml of water. The wash water was extracted 3 times with 100 ml of ethyl acetate. The combined organic phases were dried and vacuum filtered. The filter was rinsed and the filtrate was evaporated to dryness. The residue was chromatographed over silica gel and elution with ether. The ether was evaporated to obtain 8.69 g of the syn isomer of cyanomethyl 2-(cyanomethyloxyimino)-2-(2-tritylamino-4-thiazolyl)-acetate in the form of an oil.

RMN Spectrum (deuterochloroform-60 MHz): peaks at 6.8 ppm (thiazole proton); at 7.37 ppm (trityl protons).

STEP B: syn isomer of 2-(cyanomethyloxyimino)-2-(2-tritylamino-4-thiazolyl)-acetic acid 17.1 ml of N sodium hydroxide solution was added dropwise over 20 minutes to a mixture of 8.69 g of the product of Step A in 52 ml of dioxane in an ice bath and the mixture was abandoned whereby there was a spontaneous heating. 10.5 ml of 2 N hydrochloric acid were added thereto and the dioxane and almost all the water was evaporated. 20 ml of water and 30 ml of ether were added thereto and the mixture was stirred for 15 minutes. The crystals were recovered by vacuum filtration, were rinsed with water and ether and dried to obtain 4.32 g of the syn isomer of 2-(cyanomethyloxyimino)-2-(2-tritylamino-4-thiazolyl)-acetic acid with a melting point of 180° C. (with decomposition).

RMN Spectrum (deuterochloroform-60 MHz): peaks at 4.7 ppm (OCH2CN); at 6.7 ppm (thiazole proton); at 7.34 ppm (trityl proton).

STEP C: syn isomer of 2-(2-tritylamino-4-thiazolyl-2-(tetrazol-5-yl-methyloxyimino)-acetic acid A mixture of 2.43 g of the product of Step B and 12 ml of dimethylformamide was stirred and 1.5 g of sodium nitride and 1.5 g of ammonium chloride were added thereto. The mixture was heated at 75° C. for 5 hours and was then cooled to room temperature. 120 ml of distilled water, 40 ml of ethyl acetate and 30 ml of formic acid were added thereto and the mixture was vacuum filtered. The recovered precipitate was rinsed with water, with ethyl acetate and then with ether and was dried to 1.275 g of the syn isomer of 2-(2-tritylamino-4-thiazolyl)-2-(tetrazol-5-yl-methyloxyimino)-acetic acid and the filtrate was evaporated to dryness to obtain 0.127 g of the same product.

Analysis: $C_{26}H_{21}O_3N_7S$: molecular weight=511.55; Calculated: %C 61.0, %H 4.1, %N 19.2, %S 6.3; Found: 61.1, 4.6, 17.8, 5.8.

| U.V. Spectrum (ethanol + DMSO): | |
|---|---|
| Inflex. at 259 nm | |
| Inflex. at 265 nm | $\epsilon = 11,000$ |
| Inflex. at 271 nm | |
| Inflex. at 294 nm | $\epsilon = 6,600$ |
| U.V. Spectrum (0.1N HCl in ethanol): | |
| Inflex. at 270 nm | |
| Max. at 275 nm | $\epsilon = 13,700$ |

RMN Spectrum (DMSO): peaks at 7.28 ppm (trityl); at 6.88 ppm (thiazole).

I.R. Spectrum (Nujol): absorption at 1608 cm$^{-1}$ (aromatic); at 1624 cm$^{-1}$ (NH); at 1580 cm$^{-1}$ (C=N, N=N); at 1557 and 1491 cm$^{-1}$ (COO−).

STEP D: syn isomer of tert.-butyl 3-acetoxymethyl-7-[2-(2-tritylamino-4-thiazolyl)-2-(tetrazol-5-yl-methyloxyimino)acetamido]-ceph-3-eme-4-carboxylate A solution of 0.5 g of dicyclohexylcarbodiimide in 5 ml of methylene chloride was added to a mixture of 1.024 g of the product of Step C, 0.656 mg of tert.-butyl 7-amino-3-acetoxymethyl-ceph-3-eme-4-carboxylate and 2 ml of pyridine and the mixture was stirred for one hour at room temperature. The mixture was vacuum filtered and 25 ml of N hydrochloric acid were added to the filtrate. The mixture was stirred for 5 minutes and the decanted organic phase was washed with 25 ml of water, was dried and evaporated to dryness under reduced pressure. The residue was taken up in isopropyl ether and efflorescenced. The mixture was vacuum filtered and the recovered product was rinsed with isopropyl ether and dried to obtain 1.778 g of raw product. The latter was dissolved in 4 ml of ethyl acetate and the solution was treated with activated carbon and was filtered. 20 ml of isopropyl ether were added to the filtrate over 5 minutes with stirring and after stirring for another 5 minutes, the mixture was vacuum filtered. The recovered product was rinsed with isopropyl ether and dried to obtain 1.412 g of the syn isomer of tert.-butyl 3-acetoxymethyl-7-[2-(2-tritylamino-4-thiazolyl)-2-(tetrazol-5-yl-methyloxyimino)-acetamido]-ceph-3-eme-4-carboxylate in the form of a white product melting at 158° C.

Analysis: $C_{40}H_{39}O_7N_9S_2$; Calculated: %C 58.5, %H 4.8, %N 15.3, %S 7.8; Found: 58.5, 5.0, 14.7, 7.6.

| U.V. Spectrum (0.1 N HCl in ethanol): | |
|---|---|
| max. at 267–268 nm | $\epsilon = 19,400$ |
| Inflex. at 290 nm | |

I.R. Spectrum (CHCl$_3$): absorption at 1787 cm$^{-1}$ ($\beta$-lactam); at 1738 cm$^{-1}$ (esters); at 1686 and 1673 cm$^{-1}$ (amide).

RMN Spectrum (deuterochloroform): peaks at 7.2 ppm (trityl); at 6.75 ppm (thiazole); at 1.5 ppm (tert.-butyl); at 2.05 ppm (acyl).

STEP E: Trifluoroacetate of the syn isomer of 3-acetoxymethyl-7-[2-(2-amino-4-thiazolyl)-2-(tetrazol-5-yl)-methyloxyimino)-acetamido]-ceph-3-eme-4-carboxylic acid A mixture of 1.226 g of the product of Step D and 12 ml of trifluoroacetic acid was stirred at room temperature for 30 minutes and the acid was partially evaporated under reduced pressure. 120 ml of isopropyl ether were added thereto to effect precipitation. The mixture was vacuum filtered and the recovered product was rinsed with isopropyl ether and dried to obtain 1.061 g of impure product containing the starting material which was partially reacted. The trifluoroacetic acid operation was repeated twice to obtain 0.879 g of the trifluoroacetate of the syn isomer of 3-acetoxymethyl-7-[2-(2-amino-4-thiazolyl)-2-(tetrazol-5-yl)-methyloxyimino)-acetamido]-ceph-3-eme-4-carboxylic acid.

STEP F: syn isomer of sodium 3-acetoxymethyl-7-[2-(2-amino-4-thiazolyl)-2-(tetrazol-5-yl-methyloxyimino)-acetamido]-ceph-3-eme-4-carboxylic acid The product of Step E was dissolved in 1.8 ml of methanol and 2.8 ml of a molar solution of sodium acetate in methanol was slowly added thereto with stirring at room temperature and then 18 ml of ethanol were added over 5 minutes. The mixture was stirred on an ice bath for 15 minutes and was then vacuum filtered. The product was rinsed with ethanol, then with ether and dried to obtain 0.447 g of the syn isomer of sodium 3-acetoxymethyl-7-[2-(2-amino-4-thiazolyl)-2-(tetrazol-yl-methyloxyimino)-acetamido]-ceph-3-eme-4-carboxylic acid.

Analysis: $C_{17}H_{17}O_7N_9S_2$; molecular weight=523.5; Calculated: %C 37.4, %H 3.0, %N 23.1, %S 11.8; Found: 37.8, 3.2, 21.1, 11.1.

RMN Spectrum (deuterochloroform): peaks at 6.73 ppm (thiazole); at 7.25 ppm (trityl).

EXAMPLE 13 syn isomer of 3-acetoxymethyl-7-[2-(2-amino-4-thiazolyl)-2-(phenylcarbonyloxyimino)-acetamido]-ceph-3-eme-4-carboxylic acid STEP A: syn isomer of diethylamine 3-acetoxymethyl-7-[2-(2-tritylamino-4-thiazolyl)-2-(phenylcarbonyloxyimino)-acetamido]-ceph-3-eme-4-carboxylate A mixture of 0.683 g of the syn isomer of 3-acetoxymethyl-7-[2-(2-tritylamino-4-thiazolyl)-2-(hydroxyimino)-acetamido]-ceph-3-eme-4-carboxylic acid, 10 ml of methylene chloride, 0.2 ml of pyridine and 0.2 ml of benzoyl chloride was stirred at room temperature for 10 minutes and was washed with water acidified to a pH of 1. The organic phase was dried, vacuum filtered and evaporated to dryness to obtain 0.737 g of raw product. The latter was dissolved in 5 ml of ethyl acetate and 0.1 ml of diethylamine was added thereto. After 10 minutes, the mixture was vacuum filtered to obtain 0.27 g of the syn isomer of diethylamine 3-acetoxymethyl-7-[2-(2-tritylamino-4-thiazolyl)-2-(phenylcarbonyloxyimino)-acetamido]-ceph-3-eme-4-carboxylate.

STEP B: syn isomer of 3-acetoxymethyl-7-[2-(2-amino-4-thiazolyl)-2-(phenyl-carbonyloxyimino)-acetamido]-ceph-3-eme-4-carboxylic acid A mixture of 0.27 g of the product of Step A and 2 ml of 50% aqueous formic acid was stirred at 45° C. for 10 minutes and was thn evaporated to dryness. The residue was triturated with ether and 1.55 g of raw product were recovered which was dissolved in 0.5 ml of methanol. 5 ml of ether were added thereto to recover 0.14 g of the syn isomer of 3-acetoxymethyl-7-[2-(2-amino-4-thiazolyl-2-(phenylcarbonyloxyimino)-acetamido]-ceph-3-eme-4-carboxylic acid.

Analysis: $C_{22}H_{19}O_6N_5S_2$; molecular weight=513.5; Calculated: %N 13.64; Found: 13.4.

EXAMPLE 14

Bis-trifluoroacetate of the syn isomer of 3-acetoxymethyl-7-[2-(2-amino-4-thiazolyl)-2-(2-amino-ethoxyimino)-acetamido]-ceph-3-eme-4-carboxylic acid

STEP A: syn isomer of ethyl 2-(2-bromoethoxyimino)-2-(2-tritylamino-4-thiazolyl)-acetate A mixture of 4.94 g of the syn isomer of ethyl 2-hydroxyimino-2-(2-tritylamino-4-thiazolyl)-acetate hydrochloride in 10 ml of dimethylformamide was admixed under an inert atmosphere at room temperature over 3 minutes with 4.14 g of potassium carbonate and the mixture was stirred at 20° C. for 20 minutes. 8.65 ml of 1,2-dibromoethane were added thereto and the mixture was stirred for 30 hours and was then poured into a mixture of 100 ml of distilled water and 20 ml of methylene chloride. The decanted aqueous phase was extracted with methylene chloride and the combined organic phases were rinsed with distilled water. The wash water was reextracted with methylene chloride and the combined organic solution were dried and vacuum filtered. The filter was rinsed with methylene chloride and the filtrate was evaporated to dryness. The residue was chromatographed over silica gel and was eluted with benzene containing 5% ether. The first fraction was crystallized from methanol after dissolution at 50°-60° C. and was vacuum filtered at 0° to 5° C. to obtain 1.16 g of of the syn isomer of ethyl 2-(bromoethoxyimino)-2-(2-tritylamino-4-thiazolyl)-acetate in the form of a white cream product melting at 117° C. and a second homogeneous fraction of 1.258 of product was also obtained.

RMN Spectrum (deuterochloroform): triplet=3.55 ppm J=7 Hz (C$\underline{H}_2$Br); triplet=4.51 ppm J=6 Hz (N—O—C$\underline{H}_2$); singulet-6.55 ppm (triazole proton).

STEP B: syn isomer of ethyl 2-(2-iodo-ethoxyimino)-2-(2-tritylamino-4-thiazolyl)-acetate A mixture of 6 g of the product of Step A, 60 ml of methyl ethyl ketone and 2.141 g of sodium iodide was refluxed for 70 minutes and was evaporated to dryness under reduced pressure. The residue was taken up in 120 ml of methylene chloride and the solution was washed 5 times with 40 ml of water. Each of the wash waters were extracted with 2 ml of methylene chloride and the organic phase was dried and evaporated to dryness under reduced pressure to obtain 6.22 g of the syn isomer of ethyl 2-(2-iodo-ethoxyimino)-2-(2-tritylamino-4-thiazolyl)-acetate melting at 110° C.

RMN Spectrum (deuterochloroform): center triplet at 3.31 ppm (CH$_2$I); J=7 Hz; peak at 6.53 ppm (proton of 5-thiazol).

STEP C: syn isomer of ethyl 2-(2-tritylaminoethoxyimino)-2-(2-tritylamino-4-thiazolyl)-acetate A mixture of 12.2 g of the product of Step B, 80 ml of anhydrous dimethylformamide and 12.4 g of triethylamine was refluxed under an inert atmosphere at 100° C. for 5 hours and 6.2 g of tritylamine were added thereto. The mixture was held at 100° C. for 7 hours and was then allowed to cool to room temperature and was poured into 1600 ml of distilled water. The mixture was extracted 6 times with 250 ml of benzene and the combined organic phases were washed with water, with a saturated sodium bicarbonate solution and with a saturated sodium chloride solution, dried and evaporated to dryness to obtain 23.5 g of a resin. The latter was chromatographed over silica gel and was eluted with a 95-5 benzene-ether mixture. The principal fraction was eluted with pure methylene chloride to obtain 3.6 g of pure syn isomer of ethyl 2-(2-tritylaminoethoxyimino)-2-(2-tritylamino-4-thiazolyl)-acetate RMN Spectrum (deuterochloroform): peak at 6.46 ppm (thiazole proton); at 2.45 ppm (CH$_2$—NH center triplet); J=5 Hz

STEP D: syn isomer of 2-(2-tritylamino-ethoxyimino)-2-(2-tritylamino-4-thiazolyl)-acetic acid 3 ml of N sodium hydroxide solution was added under nitrogen to a solution of 2 g of the product of Step C in 10 ml of dioxane and 6.6 ml of absolute ethanol and after 65 hours, the mixture was vacuum filtered. The recovered product was washed 3 times with 3.5 ml of a 1-6.6 dioxane-ethanol mixture to obtain a first yield of 1.445 g of the syn isomer of sodium 2-(2-tritylaminoethoxyimino)-2-(2-tritylamino-4-thiazolyl)-acetate. The mother liquors were saponified under the same conditions to obtain another 0.440 g of the said sodium salt. The 1.445 g of the first yield were poured into 30 ml of water and 30 ml of chloroform and the mixture was vigorously stirred. N hydrochloric acid was added to the mixture until the pH was 2 (about 0.9 ml) and the decanted organic phase was washed 4 times with 10 ml of water. Each fraction of wash water was extracted with 3 ml of chloroform. The combined organic phases were dried and evaporated to dryness and the resulting white powder was empasted twice with 2 ml of dichloroethane and then twice with 2 ml of isopropyl ether. The product was dried to a constant weight under reduced pressure to obtain 1.202 g of the syn isomer of 2-(2-tritylamino-ethoxyimino)-2-(2-tritylamino-4-thiazolyl)-acetic acid melting at 176° C. (with decomposition). The second crop was treated in the same way to obtain 0.325 g of the said product melting at 176° C. for a total yield of 1.527 g.

RMN Spectrum (deuterochloroform): peaks at 6.65 ppm (proton in 5 of thiazole); at 2.95 ppm (CH$_2$—N).

STEP E: syn isomer of diphenylmethyl 3-acetoxymethyl-7-[2-(2-tritylamino-4-thiazolyl)-2-(2-tritylaminoethoxyimino)-acetamido]-ceph-3-eme-4-carboxylate 0.4 ml of a solution prepared extemporaneously by mixing 1.4 ml of triethylamine and sufficient methylene chloride to obtain a final volume of 10 ml was added dropwise with stirring under nitrogen to a suspension of 0.286 g of the product of Step D in 2 ml of methylene chloride and the mixture was cooled to −20° C. in a bath of acetone and frozen carbon dioxide for 5 minutes to obtain an equilibrium. Then 0.4 ml of a solution prepared extemporaneously by mixing 1.25 ml of pivaloyl chloride with methylene chloride to obtain a final volume of 10 ml was added dropwise to the mixture and the bath mass allowed to rise to −10° C. The mixture was held at the said temperature for 30 minutes and was then rinsed to 10° C. 0.17 g of diphenylmethyl 7-aminocephalospornate was added thereto all at once. The temperature was allowed to rise to room temperature and after 80 minutes, another 17.6 g of the said diphenylmethyl ester were added thereto. The mixture was stirred for 30 minutes at room temperature and was then iced for 15 hours. The temperature was allowed to rise to room temperature and the mixture was evaporated to dryness under reduced pressure. The residue was chromatographed over silica gel and was eluted with an 8-2 benzene-ethyl acetate mixture to obtain 0.208 g of the syn isomer of diphenylmethyl 3-acetoxymethyl-7-[2-(2-tritylamino-4-thiazolyl)-2-(2-tritylaminoethoxyimino)-acetamido]-ceph-3-eme-4-carboxylate.

RMN Spectrum (deuterochloroform): peaks at 1.99 ppm

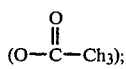

at 4.38 ppm (N—OCH$_2$); at 6.71 ppm (proton of 5-thiazole); at 6.88 ppm

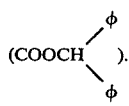

STEP F: Bis trifluoroacetate of syn isomer of 3-acetoxymethyl-7-[2-(2-amino-4-thiazolyl)-2-(2-aminoethoxyimino)-acetamido]-ceph-3-eme-4-carboxylic acid A yellow solution of 186 mg of the product of Step E in 1.8 ml of pure trifluoroacetic acid was standing for 3 minutes at room temperature and was then placed under an inert atmosphere in an ice bath. 18 ml of isopropyl ether were rapidly added thereto and the mixture was stirred for 10 minutes and was vacuum filtered. The product was rinsed with isopropyl ether, and was dried to obtain 120 mg of the bis trifluoroacetate of syn isomer of 3-acetoxymethyl-7-[2-(2-amino-4-thiazolyl)-2-(2-aminoethoxyimino)-acetamido]-ceph-3-eme-4-carboxylic acid in the form of a white powder melting at 210° C. (with decomposition).

RMN Spectrum (deuterochloroform): peaks at 2.03 ppm

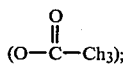

at 3.17 ppm (=NOCH$_2$); at 6.85 ppm (proton of 5-thiazole).

EXAMPLE 15 syn isomer of 3-acetoxymethyl-7-[2-(2-amino-4-thiazolyl)-2-(2-aminoethoxyimino)-acetamido]-ceph-3-eme-4-carboxylic acid 1.6 ml of a molar solution of sodium acetate in methanol were added to 220 mg of the bis-trifluoroacetate of Example 14 in a tube and the mixture was stirred until dissolution occured. The walls were rinsed with 0.66 ml of methanol and 18.6 ml of absolute ethanol were added thereto. The resulting mixture was added to a similar mixture starting from 100 mg of bis-trifluoroacetate of Example 14 and after 110 minutes, the mixture was vacuum filtered. The recovered product was washed with ethanol and then with ether and was dried to obtain 181 mg of a white powder melting at 270° C. (with decomposition) and having an Rf=0.12 (60-25-15 ethyl acetate-ethanol-water mixture).

A mixture of 120 mg of the said product and 1 ml of distilled water was stirred for 5 minutes and then pyridine was slowly added thereto to adjust the pH to 7.0 to 7.2. After stirring for 15 minutes, the mixture was vacuum filtered and the filter was rinsed with 0.5 ml of water. 40 ml of acetone were added to the filtrate and after stirring for 5 minutes and standing for 20 minutes, the mixture was vacuum filtered. The recovered product was washed three times with acetone and dried to obtain 99.5 mg of syn isomer of 3-acetoxymethyl-7-[2-(2-amino-4-thiazolyl)-2-(2-aminoethoxyimino)-acetamido]-ceph-3-eme-4-carboxylic acid in the form of a white powder.

U.V. Spectrum: Max. at 261 nm $E_1^1 = 348$

EXAMPLE 16 syn isomer of 3-acetoxymethyl-7-[2-(2-amino-4-thiazolyl)-2-(2-amino-2-thioxoethoxyimino)-acetamido]-ceph-3-eme-4-carboxylic acid STEP A: syn isomer of tert.-butyl 3-acetoxymethyl-7-[2-(2-tritylamino-4-thiazolyl)-2-(cyanomethyloxyimino)-acetamido]-ceph-3-eme-4-carboxylate A solution of 960 mg of dicyclohexylcarbodiimide in 12 ml of dry methylene chloride were added under an inert atmosphere to a stirred mixture of 1.875 g of the syn isomer of Example 12 (step B), 1.312 g of tert.-butyl 7-amino-cephalosporanate and 12 ml of dry methylene chloride and the mixture stood at room temperature for 105 minutes and was vacuum filtered to remove 457 mg of dicyclohexylurea. The filtrate was evaporated to dryness and the residue was chromatographed over silica gel. Elution was effected with methylene chloride and then with ether and the ether fraction was evaporated to dryness. The residue was taken up in ether and crystallization was induced. The mixture was iced to effect slow crystallization and was then vacuum filtered. The recovered product was empasted with ether at 0° C. and was dried to obtain 776 mg of the syn isomer of tert.-butyl 3-acetoxymethyl-7-[2-(2-tritylamino-4-thiazolyl)-2-(cyanomethyloxyimino)-acetamido]-ceph-3-eme-4-carboxylate melting at 180° C. (with decomposition).

RMN Spectrum (deuterochloroform-60 MHz): 4.9 ppm (O—CH$_2$—N); 6.8 ppm (thiazole ring proton); 7.31 ppm (trityl proton).

STEP B: syn isomer of sodium 3-acetoxymethyl-7-[2-(2-amino-4-thiazolyl)-2-(cyanomethyloxyimino)-acetamido]-ceph-3-eme-4-carboxylate A mixture of 779 mg of the product of Step A and 4 ml of trifluoroacetic acid was stirred until dissolution occurred and after standing for 17 minutes, the solution was poured into 40 ml of isopropyl ether. The mixture was stirred and vacuum filtered and the product was dried to obtain 523 mg of the trifluoroacetate of the syn isomer of 3-acetoxymethyl-7-[2-(2-amino-4-thiazolyl)-2-(cyanomethyloxyimino)-acetamido]-ceph-3-eme-4-carboxylic acid. The said product was dissolved in 2 ml of N sodium acetate in methanol and the solution was diluted with 6.6 ml of ethanol. The mixture was stirred for 10 minutes and was vacuum filtered and the recovered product was rinsed with ethanol and was dried to obtain 226 mg of the syn isomer of sodium 3-acetoxymethyl-7-[2-(2-amino-4-thiazolyl)-2-(cyanomethyloxyimino)-acetamido]-ceph-3-eme-4-carboxylate with a melting point of 200° C. (with decomposition).

Analysis: $C_{17}H_{15}O_7N_6S_2Na$; Calculated: %C 40.64, %H 3.01, %Na 4.57; Found: 40.2, 3.3, 4.5.

RMN Spectrum (deuterochloroform-60 MHz): at 4.98 ppm (O—CH$_2$—CN); at 6.86 ppm (thiazole ring proton).

STEP C: syn isomer of 3-acetoxymethyl-7-[2-(2-amino-4-thiazolyl)-2-(2-amino-2-thioxoethoxyimino)-acetamido]-ceph-3-eme-4-carboxylic acid Gaseous hydrogen sulfide was bubbled for 15 minutes through a solution of 0.502 g of the product of Step B in 2 ml of dimethylformamide and 0.14 ml of triethylamine and the mixture then stood for 20 minutes at room temperature. 20 ml of isopropyl ether were added thereto and the mixture was stirred. The isopropyl ether phase was separated and cooled and the resulting oil was added to 7 ml of ethanol with stirring. The mixture was vacuum filtered and the recovered product was rinsed with ethanol and dried to obtain 0.388 g of raw product. 0.309 g of the latter were dissolved in 1.5 ml of water and the solution and 30 mg of carbon black was stirred and vacuum filtered. The filter was rinsed with water and 5 drops of pure formic acid were added to the filtrate. The product was vacuum filtered and the product was rinsed with water and dried to obtain 0.195 g of the syn isomer of 3-acetoxymethyl-7-[2-(2-amino-4-thiazolyl)-2-(2-amino-2-thioxoethoxyimino-acetamido]-ceph-3-eme-4-carboxylic acid.

RMN Spectrum (dimethylsulfoxide):

(a)-singulet at 2.02 ppm; (b) singulet at 3.55 ppm; (c) singulet at 4.75 ppm; (d) singulet at 6.83 ppm; (e) singulet at 7.25 ppm; (f) doublet center about 9.73 ppm. J=8 Hz U.V. Spectrum (0.1 N HCl in ethanol): Max. at 265 nm; $E_1^1 = 468$; $\epsilon = 24,100$

EXAMPLE 17 syn isomer of 3-acetoxymethyl-7[2-(2-amino-4-thiazolyl)-2-(2-amino-2-thioxoethoxyimino)-acetamido]-ceph-3-eme-4-carboxylic acid

STEP A: 2-(2-tritylamino-4-thiazolyl)-2-(2-amino-2-thioxoethoxyimino)-acetic acid Gaseous hydrogen chloride was bubbled for 30 minutes at room temperature through a mixture of 2.814 g of 2-(2-tritylamino-4-thiazolyl)-2-(cyanomethoxyimino)-acetic acid and 12 ml of a solution of 1.6 ml of triethylamine in 20 ml of dimethylformamide and the mixture was then stirred for 130 minutes and poured into 100 ml of water and 14.4 ml of N hydrochloric acid. The mixture was vigorously stirred and vacuum filtered. The product was rinsed with water and the mixture was added to methylene chloride after which crystallization occured. The mixture was vacuum filtered and the recovered product was rinsed and dried to obtain 2.47 g of 2-(2-tritylamino-4-thiazolyl)-2-(2-amino-2-thioxoethoxyimino)-acetic acid melting at ≃180° C.

RMN Spectrum (DMSO): 6.96 ppm (trityl); 7.33 ppm (5-proton of thiazole).

STEP B: syn isomer of 3-acetoxymethyl-7-[2-(2-tritylamino-4-thiazolyl)-2-(2-amino-2-thioxoethoxyimino)-acetamido]-ceph-3-eme-4-carboxylic acid A solution of 0.5 g of dicyclohexyldicarbodiimide in 5 ml of methylene chloride was added to a solution of 1.01 g of the product of Step A, 2 ml of pyridine and 0.656 g of 7-amino-cephalosporanic acid and the mixture was stirred at room temperature to effect precipitation and was vacuum filtered. The product was rinsed with methylene chloride and dried to remove about 0.5 g of dicyclohexylurea. The filtrate was poured into 25 ml of hydrochloric acid and the mixture was stirred for 5 minutes. The decanted organic phase was washed with 25 ml of water and was dried and vacuum filtered. The filtrate was evaporated to dryness and the residue was taken up in isopropyl ether. Efflorescence occured and the mixture was vacuum filtered. The recovered product was rinsed and was dissolved in 4 ml of ethyl acetate 0.18 g of activated carbon were added thereto and the mixture was vacuum filtered. The filter was rinsed with ethyl acetate and the filtrate was stirred while 20 ml of isopropyl ether were added over 5 min-

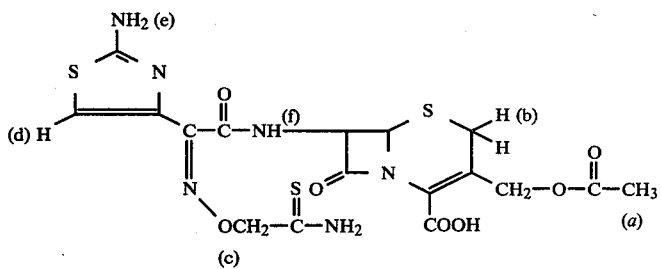

utes. The mixture was stirred another 5 minutes and was vacuum filtered. The recovered product was rinsed with isopropyl ether and was dried to obtain the syn isomer of 3-acetoxymethyl-7-[2-(2-tritylamino-4-thiazolyl)-2-(2-amino-2-thioxoethoxyimino)-acetamido]-ceph-3-eme-4-carboxylic acid.

STEP C: syn isomer of 3-acetoxymethyl-7-[2-(2-amino-4-thiazolyl)-2-(2-amino-2-thioxoethoxyimino)-acetamido]-ceph-3-eme-4-carboxylic acid A mixture of the product of Step B and 12 ml of trifluoroacetic acid was stirred for 30 minutes at room temperature and part of the acid was evaporated under reduced pressure. 120 ml of isopropyl ether were added thereto. Efflorescence occured and the mixture was occur filtered. The product was rinsed with isopropyl ether and dried to obtain the syn isomer of 3-acetoxymethyl-7-[2-(2-amino-4-thiazolyl)-2-(2-amino-2-thioxoethoxyimino)-acetamido]-ceph-3-eme-4-carboxylic acid identical to the product of Example 16.

EXAMPLE 18

Trifluoroacetate of syn isomer of 3-acetoxymethyl-7-[2-(2-amino-4-thiazolyl)-2-(2-oxopropyloxyimino)-acetamido]-ceph-3-eme-4-carboxylic acid STEP A: syn isomer of 3-acetoxymethyl-7-[2-(2-tritylamino-4-thiazolyl)-2-(2-oxopropyloxyimino)-acetamido]-ceph-3-eme-4-carboxylic acid 14 ml of triethylamine were added at 20° C. with stirring to a mixture of 7.6 g of the syn isomer of diethylamine 3-acetoxymethyl-7-[2-(2-tritylamino-4-thiazolyl)-2-hydroxyimino-acetamido]-ceph-3-eme-4-carboxylate, 114 ml of distilled water and 114 ml of methylene chloride and after stirring the mixture for 5 minutes, 8.45 ml of bromoacetone were added thereto at 20°-25° C. The mixture was stirred at 25° C. for 5 hours and was then acidified to a pH of 1 to 2 with 6 ml of hydrochloric acid. The decanted aqueous phase was extracted twice with 50 ml of methylene chloride and the combined organic phases were washed with water. The wash waters were extracted with methylene chloride and the organic phase was dried and evaporated to dryness to obtain 8.48 g of a resin. The latter was dissolved in 8.5 ml of methylene chloride and the addition of 85 ml of ether thereto caused precipitation. The mixture was stirred at room temperature for 2 hours and was vacuum filtered. The recovered product was rinsed 3 times with 10 ml of ether and was dried to obtain 6.27 g of product.

The said product was taken up in 62 ml of ethyl acetate and the mixture was empasted for 5 minutes and was vacuum filtered. The filter was rinsed with ethyl acetate and the filtrate was concentrated to a volume of 50 ml. 0.6 ml of diethylamine were added all at once thereto and the mixture was stirred. The resulting gum was rinsed 3 times with 5 ml of ethyl acetate and the filtrate was diluted with 130 ml of isopropyl ether. The mixture was stirred for 15 minutes and was vacuum filtered and the recovered product was rinsed with isopropyl ether and dried to obtain 3.27 g of the syn isomer of diethylamine 3-acetoxymethyl-7-[2-(2-tritylamino-4-thiazolyl)-2-(2-oxopropyloxyimino)-acetamido]-ceph-3-eme-4-carboxylate.

3.25 g of the said salt were dissolved in 25 ml of distilled water and 98 ml of ethyl acetate and 50 ml of an aqueous saturated sodium chloride solution were added thereto. A gum was decanted off and the aqueous phase was acidified to a pH of 1 to 2 with 2.5 ml of concentrated hydrochloric acid after the addition of 50 ml of methylene chloride. The decanted aqueous phase was extracted twice with 50 ml of methylene chloride and the combined organic phases were washed with water, dried and vacuum filtered. The filtrate was evaporated to dryness to obtain 1.79 g of a resin which was dissolved in 4 ml of methylene chloride. The solution was diluted with 40 ml of ether and was vacuum filtered. The product was rinsed with ether and dried to obtain 1.22 g of the syn isomer of 3-acetoxymethyl-7-[2-(2-tritylamino-4-thiazolyl)-2-(2-oxopropyloxyimino)-acetamido]-ceph-3-eme-4-carboxylic acid.

RMN Spectrum (deuterochloroform): peaks at 2.03 ppm

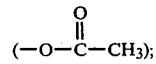

at 2.13 ppm

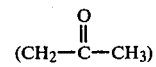

at 6.8 ppm (5-proton of thiazole)

STEP B: Trifluoroacetate of syn isomer of 3-acetoxymethyl-7-[2-(2-amino-4-thiazolyl)-2-(2-oxopropyloxyimino)-acetamido]-ceph-3-eme-4-carboxylic acid A mixture of 1.22 g of the product of Step A and 12 ml of trifluoroacetic acid was stirred at 20°-22° C. for 15 minutes and the mixture was evaporated under reduced pressure to a volume of 6 ml. 60 ml of isopropyl ether were added thereto and the mixture was stirred at room temperature for 15 minutes and was vacuum filtered. The recovered product was rinsed 5 times with 5 ml of isopropyl ether and was dried under reduced pressure to obtain 0.97 g of raw product. The latter was dissolved in 4 ml of acetone containing 1% of water and after the addition of 0.2 g of activated carbon, the mixture was stirred for 5 minutes at 20°-22° C. and was filtered. The filter was rinsed with 1 ml of acetone containing 1% of water and the product was added at 20°-22° C. to 90 ml of ether. The mixture was stirred for one hour at 20°-22° C. and was vacuum filtered. The product was rinsed with ether and dried to obtain 0.57 g of trifluoroacetate of syn isomer of 3-acetoxymethyl-7-[2-(2-amino-4-thiazolyl)-2-(2-oxopropyloxyimino)acetamido]-ceph-3-eme-4-carboxylic acid.

EXAMPLE 19 syn isomer of sodium 3-acetoxymethyl-7-[2-(2-amino-4-thiazolyl)-2-(2-oxopropyloxyimino)-acetamido]-ceph-3-eme-4-carboxylate A solution of 0.57 g of the trifluoroacetate of Example 18, 0.25 ml of distilled water, 2.3 ml of methanol and 2.3 ml of a solution of N sodium acetate in methanol was then filtered and the filter was rinsed with 2.3 ml of ethanol. The filtrate was concentrated to a volume of 3 ml of a colorless solution which was diluted with 20 ml of ethanol, stirred for 10 minutes at 20°-22° C. and was vacuum filtered. The recovered product was rinsed 3 times with 3 ml of ethanol and dried to obtain 0.38 g of product. The filtrate was evaporated to dryness to obtain another 0.12 g of the product which was empasted at 20° C. for 5 minutes with 0.6 ml of methanol. The mixture was diluted with 6 ml of ethanol and then rinsed to obtain 0.07 g of the product. The 0.45 g of combined products were dissolved at room temperature in 2 ml of distilled water and 12 ml of acetone were slowly added thereto with stirring at 20° C. The mixture was vacuum filtered to remove the gummy precipitated and the filtrate was evaporated to dryness. The treatment was repeated with 1.5 ml of water and 10 ml of acetone and the residue was taken up in 5 ml of pure ethanol. The mixture was vacuum filtered at 20° C. and the recovered product was rinsed 3 times with 1 ml of ethanol and was dried under reduced pressure to obtain 0.26 g of the syn isomer of sodium 3-acetoxymethyl-7[2-(2-amino-4-thiazolyl)-2-(2-oxopropyloxyimino)-acetamido]ceph-3-eme-4-carboxylate RMN Spectrum (DMSO): at 2 ppm

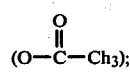

at 2.13 ppm

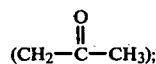

at 6.78 ppm (5 proton of thiazole).

EXAMPLE 20

Bis trifluoroacetate of syn isomer of 3-methyl-7-[2-(2-amino-4-thiazolyl)-2-(2-aminoethoxyimino)-acetamido]-ceph-3-eme-4-carboxylic acid STEP A: syn isomer of diphenylmethyl 3-methyl-7-[2-(2-tritylamino-4-thiazolyl)-2-(2-tritylaminoethoxyimino)-acetamido]-ceph-3-eme-4-carboxylate 1.3 ml of a solution of 1.25 ml of pivaloyl chloride in sufficient methylene chloride for a final volume of 10 ml were added at −20° C. to a solution of 0.923 g of the syn isomer of 2-(2-tritylamino-4-thiazolyl)-2-(2-trityaminoethoxyimino)acetic acid 6.5 ml of methylene chloride and 1.3 ml of a solution of 1.4 ml of triethylamine in sufficient methylene chloride for a final volume of 10 ml and the mixture was held at −10° C. for 35 minutes. The temperature then rose to 10° C. and 0.494 g of the dibenzyl ester of 7-amino-desacetoxy-cephalosporanic acid were added to the mixture. The temperature was allowed to rise to room temperature and the mixture was stirred for 80 minutes. Another 77 mg of the dibenzyl ester were added thereto and the mixture was stirred for one hour and was then evaporated to dryness under reduced pressure. The residue was chromatographed over silica gel and was eluted with an 8-2 benzene-ethyl acetate mixture to obtain 504 mg of the syn isomer of diphenylmethyl 3-methyl-7-[2-(2-tritylamino-4-thiazolyl)-2-(2-tritylaminoethoxyimino)-acetamido]-ceph-3-eme-4-carboxylate.

RMN Spectrum (deuterochloroform): peaks at 2.1 ppm (3-methyl); at 6.93 ppm (proton of phenylmethyl)

STEP B: Bis trifluoroacetate of syn isomer of 3-methyl-7-[2-(2-amino-4-thiazolyl)-2-(2-aminoethoxyimino)-acetamido]-ceph-3-eme-4-carboxylic acid A mixture of 357 mg of the product of Step A and 3 ml of trifluoroacetic acid was stirred for 2½ hours in an ice bath and then 40 ml of a 1-1 isopropyl ether-petroleum ether (b.p.=64°-75° C.) were rapidly added thereto with stirring. The mixture was stirred for 10 minutes and was vacuum filtered. The recovered product was rinsed with isopropyl ether and then with ether and dried to a constant weight to obtain 200 mg of the bis trifluoroacetate of syn isomer of 3-methyl-7-[2-(2-amino-4-thiazolyl)-2-(2-aminoethoxyimino)acetamido]-ceph-3-eme-4-carboxylic acid in the form of a white powder melting at 250° C. (with decomposition).

RMN Spectrum (DMSO): at 2.03 ppm (3-methyl); at 6.88 ppm (5-proton of thiazole).

EXAMPLE 21

Trifluoroacetate of syn isomer of 3-acetoxymethyl-7-[2-(2-amino-4-thiazolyl)-2-(2-bromoethoxyimino)-acetamido]-ceph-3-eme-4-carboxylic acid STEP A: syn isomer of 2-(2-bromoethoxyimino)-2-(2-tritylamino-4-thiazolyl)-acetic acid 4.14 g of potassium carbonate were added over 3 minutes under argon at room temperature to a mixture of 4.94 g of syn isomer of ethyl 2-(2-tritylamino-4-thiazolyl)-2-hydroxyimino-acetate hydrochloride and 10 ml of dimethylformamide, and after stirring the mixture at 20° C. for 20 minutes, 8.65 ml of 1,2-dibromoethane were added thereto. The mixture was stirred for 30 hours and was poured into 100 ml of distilled water and 20 ml of methylene chloride. The mixture was decanted and the aqueous phase was extracted with methylene chloride. The combined organic phases were dried and vacuum filtered. The filter was rinsed and the filtrate was evaporated to dryness to obtain a raw product which was chromatographed over silica gel. Elution with benzene containing 5% of ether yielded a first fraction which was crystallized from methanol after dissolution at 50°-60° C. Vacuum filtration at 0° to 5° C. yielded 1.16 g of the syn isomer of ethyl 2-(2-tritylamino-4-thiazolyl)-2-(2-bromoethoxyimino)-acetate in the form of a white cream product melting at 117° C. Next obtained was a homogenous fraction of 1.258 g of product.

A mixture of 2.88 g of the said ester and 4.3 ml of dioxane was stirred under an inert atmosphere at room temperature until dissolution occured and then 30.6 ml of a solution of 0.5 M potassium hydroxide in ethanol were added thereto over 3 minutes at 20°-25° C. The mixture was stirred at room temperature under an inert atmosphere for 24 hours and after 2 or 3 hours a potassium salt crystallized. The mixture was vacuum filtered at room temperature and the recovered product was rinsed with 1 ml of ether and 3 times with 2 ml of methylene chloride to obtain 1.6 g of the syn isomer of potassium 2-(2-tritylamino-4-thiazolyl)-2-(2-bromoethoxyimino)-acetate.

The said potassium salt was taken up in a mixture of 10 ml of distilled water, 10 ml of methylene chloride and 1 ml of 2 N hydrochloric acid, and after stirring for a few minutes in a flask, another 10 ml of distilled water, 10 ml of methylene chloride and 1 ml of 2 N hydrochloric acid were added thereto. The organic phase was washed 3 times with 20 ml of distilled water until neutral and the wash waters were extracted with 10 ml of methylene chloride. The combined organic phases were dried and vacuum filtered and the filter was rinsed. The filtrate was evaporated to dryness to obtain 1.465 g of resin which was taken up in 15 ml of 1,2-dichloroethane. The mixture was heated to 40° C. for dissolution and was cooled to 20° C. after which crystallization was induced. The mixture was stirred at 20° C. for 3 hours and was vacuum filtered. The recovered product was rinsed with 0.5 ml of 1,2-dichloroethane and dried to obtain 1.185 g of the syn isomer of 2-(2-tritylamino-4-thiazolyl)-2-(2-bromoethoxyimino)-acetic acid in the form of a white product melting at 150° C. and having a Rf=0.65 (acetone containing 5% water).

Analysis: Calculated: %C 58.21, %H 4.13, %N 7.82, %S 5.98, %Br 14.89; Found: 58.0, 4.2, 7.8, 5.9, 15.2.

RMN Spectrum (deuterochloroform): Peaks at 3.44 ppm (triplet—$CH_2Br$ J=7.5 Hz); at 4.3 ppm (triplet—$N\overline{O}$—$CH_2$— J=7 Hz); at 6.55 ppm (singulet—5-proton of thiazole).

STEP B: syn isomer of tert.-butyl 3-acetoxymethyl-7-[2-(2-tritylamino-4-thiazolyl)-2-(2-bromoethoxyimino)-acetamido]-ceph-3-eme-4-carboxylate 4.75 ml of 0.5 M dicyclohexylcarbodiimide in methylene chloride was slowly added under an inert atmosphere to a cooled mixture of 1.185 g of the product of Step A, 0.725 g of tert-butyl ester of 7-amino-cephalosporanic acid and 20 ml of methylene chloride and the mixture was stirred at 0° to 5° C. for 90 minutes and at 20°–25° C. for one hour. The mixture ws vacuum filtered at 20° C. and the filter was rinsed with methylene chloride to remove 0.293 g of dicyclohexylurea. The filtrate was evaporated to dryness under reduced pressure to obtain 2.09 g of a residue which was chromatographed over silica gel. Elution with a 1-1 benzene-ether mixture to obtain 1.129 g of the syn isomer of tert.-butyl 3-acetoxymethyl-7-[2-(2-tritylamino-4-thiazolyl)-2-(2-bromoethoxyimino)-acetamido]-ceph-3-eme-4-carboxylate.

STEP C: Trifluoroacetate of syn isomer of 3-acetoxymethyl-7-[2-(2-amino-4-thiazolyl)-2-(2-bromoethoxyimino)-acetamido]ceph-3-eme-4-carboxylic acid A mixture of 1.301 g of the product of Step B and 13 ml of trifluoroacetic acid was stirred under an inert atmosphere for 10 minutes at room temperature with dissolution occuring in the first minute and the mixture was evaporated under reduced pressure at a temperature less than 35° C. to a volume of about 5 ml. The mixture was cooled in an ice bath and 42 ml of isopropyl ether were added thereto all at once with stirring to obtain a yellow precipitate. The mixture was stirred at room temperature for 30 minutes and was vacuum filtered. The recovered product was rinsed 3 times with 2.6 ml of isopropyl ether and dried under reduced pressure to obtain 0.893 g of the trifluoroacetate of syn isomer of 3-acetoxymethyl-7-[2-(2-amino-4-thiazolyl)-2-(2-bromoethoxyimino)-acetamido]-ceph-3-eme-4-acid.

EXAMPLE 22 syn isomer of sodium 3-acetoxymethyl-7-[2-(2-amino-4-thiazolyl)-2-(2-bromoethoxyimino)-acetamido]-ceph-3-eme-4-carboxylate A mixture of 0.893 g of the product of Example 21 and 3.5 ml of a molar solution of sodium acetate in methanol was stirred under an inert atmosphere at room temperature until dissolution occured and the solution was filtered. The resulting product was rinsed once with 1 ml and twice with 0.5 ml of anhydrous pure methanol and the filtrate was added to 40 ml of absolute ethanol during which first a turbidity occured followed by a precipitation of a sodium salt. The mixture was stirred for 2 hours at room temperature and was vacuum filtered. The recovered product was rinsed 3 times with one ml of absolute ethanol and 3 times with 3 ml of ether and was dried under reduced pressure to obtain 0.545 g of the syn isomer of sodium 3-acetoxymethyl-7-[2-(2-amino-4-thiazolyl)-2-(2-bromoethoxyimino)-acetamido]-ceph-3-eme-4-carboxylate with a specific rotation of $[\alpha]_D^{20} = +45° \pm 1.5°$ (c=1% in water) and an Rf=0.6 (acetone containing 10% of water).

Analysis: Calculated: %C 35.80, %H 3.00, %N 12.28, %S 11.24, %Br 14.01; Found: 36.0, 3.1, 11.9, 11.2, 13.7.

RMN Spectrum (CD$_3$)$_2$SO peaks at 2.0 ppm

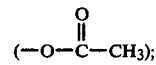

at 3.62 ppm (triplet —$CH_2Br$) J=6 Hz; at 4.33 ppm (triplet —=N—O—$CH_2$—) J=6 Hz; at 6.75 ppm (5-proton of thiazole).

EXAMPLE 23 syn isomer of 3-acetoxymethyl-7-[2-(2-amino-4-thiazolyl)-2-{2-(2-aminophenylthio)-ethoxyimino}-acetamido]-ceph-3-eme-4-carboxylic acid STEP A: syn isomer of 3-acetoxymethyl-7-[2-(2-tritylamino-4-thiazolyl)-2-(2-bromoethoxyimino)-acetamido]-ceph-3-eme-4-carboxylic acid A mixture of 26.85 g of the syn isomer of 2-(2-tritylamino-4-thiazolyl)-2-(2-bromoethoxyimino)-acetic acid, 7.25 g of 1-hydroxy-1H-benzo-triazole, 12 g of dicyclohexylcarbodiimide and 350 ml of methylene chloride was stirred at room temperature for 23 hours and was vacuum filtered to remove dicyclohexylurea. The filtrate was washed with water, with aqueous 0.1 M sodium bicarbonate solution and then with water, was dried and evaporated to dryness under reduced pressure. The residue was taken up in 150 ml of ether to obtain 25.4 g of crystals which were dissolved in 235 ml of anhydrous methylene chloride to which was added 10.56 g of 7-amino-cephalosporanic acid, 200 ml of anhydrous methylene chloride and 10.9 ml of triethylamine. The mixture was stirred for 65 hours and then 350 ml of water and 45 ml of 2 N hydrochloric acid were added thereto. The mixture was stirred and the organic phase was washed with water, dried and evaporated to dryness under reduced pressure. The residue was taken up in 75 ml of ethyl acetate and the mixture was diluted with 520 ml of ether and was vacuum filtered to obtain 24.75 g of the syn isomer of 3-acetoxymethyl-7-[2-(2-tritylamino-4-thiazolyl)-2-(2-bromoe-thoxyimino)-acetamido]-ceph-3-eme-4-carboxylic acid.

STEP B: syn isomer of 3-acetoxymethyl-7-[2-(2-tritylamino-4-thiazolyl-2-{-2-(2-aminophenylthio)-ethoxyimino}-acetamido]-ceph-3-eme-4-carboxylic acid 790 mg of the product of Step A, 8 ml of benzene and 0.28 ml of pure triethylamine were successively introduced and after total dissolution occurred, 0.14 ml of 2-amino-thiophenol and 5 ml of distilled water and a few mg of methyl tricapryl ammoniun chloride were added thereto. The mixture was vigorously stirred overnight and 2 ml of 0.1 N hydrochloric acid were added thereto. The mixture was extracted with methylene chloride and the organic phase was washed with water, dried and evaporated to dryness. The residue was taken up in ether and the mixture was vacuum filtered to obtain 690 mg of the syn isomer of 3-acetoxymethyl-7-[2-(2-trityl-amino-4-thiazolyl)-2-{(2-aminophenylthio)ethoxyimino}-acetamido]-ceph-3-eme-4-carboxylic acid.

STEP C: syn isomer of 3-acetoxymethyl-7-[2-(2-amino-4-thiazolyl)-2-{2-(2-aminophenylthio)-ethoxyimino}-acetamido]ceph-3-eme-4-carboxylic acid A mixture of the product of Step B and 5.3 ml of 66% aqueous formic acid was heated at 55° C. for 15 minutes and was then cooled and vacuum filtered. The filtrate was evaporated to dryness under reduced pressure and the residue was taken up in ethanol. The solution was evaporated to dryness under reduced pressure to allow the syn isomer of 3-acetoxymethyl-7-[2-(2-amino-4-thiazolyl)-2-{2-(2-aminophenylthio)-ethoxyimino}-acetamido]-ceph-3-eme-4-carboxylic acid which was used as is for the next example.

EXAMPLE 24 syn isomer of sodium 3-acetoxymethyl-7-[2-(2-amino-4-thiazolyl)-2-{2-(2-aminophenylthio)-ethoxyimino}-acetamido]ceph-3-eme-4-carboxylate 1 ml of methanol was added to a mixture of the product of Example 23 and 1.5 ml of molar sodium acetate in methanol and the mixture was diluted with 6 ml of ethanol and was vacuum filtered. The recovered product was washed with ethanol and empasted with ether to obtain 235 mg of the syn isomer of sodium 3-acetoxymethyl-7-[2-(2-amino-4-thiazolyl)-2-{2-(2-aminophenylthio)-ethoxyimino}-acetamido]-ceph-3-eme-4-carboxylate.

RMN Spectrum(CD$_3$)$_2$SO peaks at 1.99 ppm

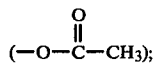

at ~4.08 ppm (=N—O—CH$_2$—); at 6.73 ppm (5-proton of thiazole).

Analysis: C$_{23}$H$_{23}$O$_7$N$_6$S$_3$Na; molecular weight=614.65; Calculated: %C 44.94, %H 3.77, %N 13.67, %S 15.65; Found: 44.8, 3.7, 13.3, 14.8.

EXAMPLE 25 syn isomer of 3-acetoxymethyl-7-[2-(2-amino-4-thiazolyl)-2-[(2-amino-1,3,4-thiadiazol-5-yl)-thioethoxyimino]-acetamido]-ceph-3-eme-4-carboxylic acid STEP A: syn isomer of 3-acetoxymethyl-7-[{2-(2-tritylamino-4-thiazolyl)-2-(2-amino-1,3,4-thiadiazol-5-yl)-thioethoxyimino}-acetamido]-ceph-3-eme-4-carboxylic acid A solution of 1.9 g of 2-amino-5-thiol-1,3,4-thiadiazole and 15 ml of a molar solution of lithium methylate in methanol was evaporated to dryness under reduced pressure to obtain the lithium derivative of 2-amino-5-thiol-1,3,4-thiadiazole in the form of a resin. A mixture of 7.91 g of the syn isomeer of 3-acetoxymethyl-7-[{2-(2-tritylamino-4-thiazolyl)-2-(2-bromoethoxyimino)}-acetamido]-ceph-3-eme-4-carboxylic acid, 30 ml of anhydrous dimethylformamide and 670 mg of lithium iodide was stirred until dissolution occured and then a mixture of the above lithium derivative in 15 ml of dimethylformamide was added thereto. The mixture was stirred at room temperature for 5½ hours and then 450 ml of water and 1 ml of formic acid were added thereto. The mixture was extracted with ethyl acetate and the organic phase was dried and evaporated to dryness under reduced pressure. The residue was chromatographed over silica gel and was eluted with an 70-20-10-1 ethyl acetate-methanol-water-triethylamine mixture to obtain 2.36 g of the syn isomer of 3-acetoxymethyl-7-[{2-(2-tritylamino-4-thiazolyl)-2-(2-amino-1,3,4-thiadiazol-5-yl)-thioethoxyimino}-acetamido]-ceph-3-eme-4-carboxylic acid.

STEP B: syn isomer of 3-acetoxymethyl-7-[2-(2-amino-4-thiazolyl)-2-[(2-amino-1,3,4-thiadiazol-5-yl)-thioethoxyimino]-acetamido]-ceph-3-eme-4-carboxylic acid A mixture of 843 mg of the product of Step A in 6.4 ml of 66% aqueous formic acid was stirred at 55° C. for 15 minutes and the mixture was evaporated to dryness under reduced pressure. The residue was taken up in a mixture of 5 ml of ethanol and 50 ml of ether and the mixture was vacuum filtered to obtain 606 mg of raw syn isomer of 3-acetoxymethyl-7-[2-(2-amino-4-thiazolyl)-2-[(2-amino-1,3,4-thiadiazol-5-yl)thioethoxyimino]-acetamido]-ceph-3-eme-4-carboxylic acid.

EXAMPLE 26 syn isomer of sodium 3-acetoxymethyl-7-{[2-(2-amino-4-thiazolyl)-2-(2-amino-1,3,4-thiadiazol-5-yl)-thioethoxyimino}acetamido]-ceph-3-eme-4-carboxylate A mixture of the product of Example 25, 1.5 ml of a molar solution of sodium acetate in methanol and 0.5 ml of dimethylformamide was admixed with 5 ml of ethanol and the mixture was vacuum filtered. The recovered product was taken up in 7 ml of methanol and the mixture was refluxed and then added and vacuum filtered to remove impurities. The filtrate was evaporated to dryness under reduced pressure and the residue was efflorescenced in ethanol. The mixture was vacuum filtered and the product was dried to obtain 146 mg of the syn isomer of sodium 3-acetoxymethyl-7-{[2-(2-amino-4-thiazolyl)-2-(2-amino-1,3,4-thiadiazol-5-yl)-thioethoxyimino}-acetamido]-ceph-3-eme-4-carboxylate.

Analysis: $C_{19}H_{19}O_7N_8S_4Na$; molecular weight=622.66; Calculated: %C 36.65, %H 3.08, %N 17.99, %S 20.60; Found: 37.0, 3.7, 17.5, 19.8.

RMN Spectrum ((CD$_3$)$_2$SO): peaks at 1.99 ppm

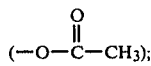

at 18 4.25 ppm (=N—O—C$\underline{H}_2$); at 6.76 (5-proton of thiazole).

EXAMPLE 27 syn isomer of
3-acetoxymethyl-7-[2-(2-amino-4-thiazolyl)-2-[2-(5-nitro-2-pyridinyl)-thioethoxyimino]-acetamido]-ceph-3-eme-4-carboxylic acid

STEP A: syn isomer of
3-acetoxymethyl-7-[2-(2-tritylamino-4-thiazolyl)-2-[2-{5-nitro-2-pyridinyl}-thioethoxyimino]-acetamido]-ceph-3-eme-4-carboxylic acid 396 mg of the syn isomer of 3-acetoxymethyl-7-[2-(2-tritylamino-4-thiazolyl)-2-bromoethoxyimino)-acetamido]-ceph-3-eme-4-carboxylic acid, 4 ml of benzene and 0.14 ml of triethylamine were successively added and after dissolution occured, 92 mg of 2-thiol-5-nitro-pyridine, 5 ml of distilled water and a few mg of methyltricaprylammonium chloride were added thereto. The mixture was stirred at room temperature for 72 hours and after the addition of 1 ml of N hydrochloric acid thereto, the mixture was extracted with ethyl acetate. The organic phase was dried and evaporated to dryness under reduced pressure. The residue was taken up in ether and the mixture was vacuum filtered to obtain 416 mg of the syn isomer of 3-acetoxymethyl-7-[2-(2-tritylamino-4-thiazolyl)-2-[2-{5-nitro-2-pyridinyl}-thioethoxyimino]-acetamido]-ceph-3-eme-4-carboxylic acid.

STEP B: syn isomer of
3-acetoxymethyl-7-[2-(2-amino-4-thiazolyl)-2-{2-(5-nitro-2-pyridinyl)-thioethoxyimino}-acetamido]-ceph-3-eme-4-carboxylic acid A mixture of the product of Step A and 3.2 ml of 66% aqueous formic acid was heated at 55° C. for 15 minutes and was then vacuum filtered to remove triphenylcarbinol. The filtrate was evaporated to dryness under reduced pressure and the residue was taken up in ethanol. The mixture was evaporated to dryness under reduced pressure to obtain syn isomer of 3-acetoxymethyl-7-[2-(2-amino-4-thiazolyl)-2-{2-(5-nitro-2-pyridinyl)-thioethoxyimino}-acetamido]-ceph-3-eme-4-carboxylic acid.

EXAMPLE 28 syn isomer of sodium 3-acetoxymethyl-7-[2-(2-amino-4-thiazolyl)-2-{2-(5-nitro-2-pyridinyl)-thioethoxyimino}-acetamido]-ceph-3-eme-4-carboxylate 2 ml of a molar solution of sodium acetate in methanol were added to a mixture of the product of Example 27 in a little methanol and the mixture was vacuum filtered to remove traces of insolubles. The filtrate was evaporated to dryness under reduced pressure and the residue was taken up in ethanol. The mixture was vacuum filtered to obtain 153 mg of the syn isomer of sodium 3-acetoxymethyl-7-[2-(2-amino-4-thiazolyl)-2-{2-(5-nitro-2-pyridinyl)-thioethoxyimino}-acetamido]-ceph-3-eme-4-carboxylate.

Analysis: $C_{22}H_{20}O_9N_7S_3Na$; molecular weight=645.63; Calculated: %C 40.93, %H 3.12, %N 15.19, %S 14.90; Found: 39.0, 3.3, 13.2, 12.9.

RMN Spectrum [(CD$_3$)$_2$SO]: peaks at 2.0 ppm

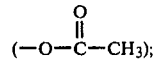

at 3.86–4.3–4.4 ppm (=N—O—C$\underline{H}_2$); at 6.76 ppm (5-proton of thiazole).

EXAMPLE 29 syn isomer of
3-acetoxymethyl-7-[2-(2-amino-4-thiazolyl)-2-{2-(3-cyano-6-methyl-2-pyridinyl)-thioethoxyimino}-acetamido]-ceph-3-eme-4-carboxylic acid

STEP A: syn isomer of
3-acetoxymethyl-7-{2-(2-tritylamino-4-thiazolyl)-2-[2-(3-cyano-6-methyl-2-pyridinyl)-thioethoxyimino]-acetamido}-ceph-3-eme-4-carboxylic acid A mixture of 791 mg of the syn isomer of 3-acetoxymethyl-7-{2-(2-tritylamino-4-thiazolyl)-2-[2-(2-bromo-ethoxyimino)]-acetamido}-ceph-3-eme-4-carboxylic acid, 326 mg of 2-thiol-3-cyano-6-methyl-pyridine, 10 ml of benzene, 0.42 ml of triethylamine, 10 ml of water and a few mg of methyltricaprylammonium chloride was stirred at room temperature for 44 hours and was then acidified with 3 ml of N hydrochloric acid. The mixture was extracted with ethyl acetate and the organic phase was dried and evaporated to dryness under reduced pressure. The residue was taken up in ether and the mixture was vacuum filtered to obtain 877 mg of raw syn isomer of 3-acetoxymethyl-7-{2-(2-tritylamino-4-thiazolyl)-2-[2-(3-cyano-6-methyl-2-pyridinyl)-thioethoxyimino]-acetamido}-ceph-3-eme-4-carboxylic acid.

STEP B: syn isomer of
3-acetoxymethyl-7-[2-(2-amino-4-thiazolyl)-2-{2-(3-cyano-6-methyl-2-pyridinyl)-thioethoxyimino}-acetamido]-ceph-3-eme-4-carboxylic acid A mixture of the product of Step A and 7 ml of 66% aqueous formic acid was stirred at 55° C. for 15 minutes and was cooled and vacuum filtered. The filtrate was evaporated to dryness under reduced presssure and the residue was taken up in ethanol. The mixture was evaporated to dryness and the raw residue was purified by forming the sodium salt which was then treated with formic acid to obtain the syn isomer of 3-acetoxymethyl-7-[2-(2-amino-4-thiazolyl)-2-{-2(3-cyano-6-methyl-2-pyridinyl)-thioethoxyimino}-acetamido]-ceph-3-eme-4-carboxylic acid.

Analysis: $C_{24}H_{23}O_7N_7S_3$; molecular weight=617.69; Calculated: %C 46.67, %H 3.75, %N 15.87, %S 15.57; Found: 46.2, 3.8, 15.2, 14.5.

RMN Spectrum (DMSO): peaks at 2.0 ppm

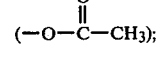

at ≃4.2–4.3–4.4 ppm (=N—OC$\underline{H}_2$—); at 6.8 ppm (5-proton of thiazole).

EXAMPLE 30 syn isomer of sodium 3-acetoxymethyl-7-[2-(2-amino-4-thiazlyl)-2-{2-(3-cyano-6-methyl-2-pyridinyl)-thioethoxyimino}-acetamido]-ceph-3-eme-4-carboxylate 4 ml of a molar solution of sodium acetate in methanol were added to a mixture of the product of Example 29 and 5 ml of methanol and the mixture was evaporated to dryness under reduced pressure. The residue was efflorescenced in ethanol and the mixture was vacuum filtered to obtain 5505 mg of the syn isomer of sodium 3-acetoxymethyl-7[2-(2-amino-4-thiazolyl)-2-{2-(3-cyano-6-methyl-2-pyridinyl)-thioethoxyimino}-acetamido]-ceph-3-eme-4-carboxylate.

EXAMPLE 31 syn isomer of 3-acetoxymethyl-7-[2-(2-amino-4-thiazolyl)2-{2-(1-methyl-5-tetrazolyl)-thioethoxyimino}-acetamido]-ceph-3-eme-4-carboxylic acid STEP A: syn isomer of diethylamine 3-acetoxymethyl-7-[2-(2-tritylamino-4-thiazolyl)-2-(2-bromoethoxyimino)-acetamido]-ceph-3-eme-4-carboxylate 0.12 ml of diethylamine was added to a solution of 0.79 g of syn isomer of 3-acetoxymethyl-7-[2-(2-tritylamino-4-thiazolyl)-2-(2-bromoethoxyimino)-acetamido]-ceph-3-eme-4-carboxylic acid in 5 ml of ethyl acetate and the mixture was stirred and vacuum filtered. The recovered product was rinsed with ethyl acetate and dried to obtain the syn isomer of diethylamine 3-acetoxymethyl-7-[2-(2-tritylamino-4-thiazolyl)-2-(2-bromoethoxyimino)-acetamido]-ceph-3-eme-4-carboxylate.

STEP B: syn isomer of 3-acetoxymethyl-7-[2-(2-tritylamino-4-thiazolyl)-2-2-(1-methyl-5-tetrazolyl)-thioethoxyimino-acetamido]-ceph-3-eme-4-carboxylic acid A mixture of 432 mg of the syn isomer of diethylamine 3-acetoxymethyl-7-[2-(2-tritylamino-4-thiazolyl)-2-(2-bromoethoxyimino)-acetamido]-ceph-3-eme-4-carboxylate, 64 mg of 1-methyl-5-mercapto-1,2,3,4-tetrazole and 2.2 ml of anhydrous dimethylformamide were heated at 50° C. in a water bath for 110 minutes, was stirred at room temperature for 90 minutes and stirred at 55° C. for 70 minutes. The mixture was cooled, diluted with 20 ml of water and stirred. The mixture was vacuum filtered to obtain 406 mg of raw syn isomer of 3-acetoxymethyl-7-[2-(2-tritylamino-4-thiazolyl)-2-{2-(1-methyl-5-tetrazolyl)-thioethoxyimino}-acetamido]-ceph-3-eme-4-carboxylic acid.

STEP C: syn isomer of 3-acetoxymethyl-7-[2-(2-amino-4-thiazolyl)-2-{2-(1-methyl-5-tetrazolyl)-thioethoxyimino}-acetamido]-ceph-3-eme-4-carboxylic acid A solution of 406 mg of the product of Step B in 3.2 ml of 66% aqueous formic acid was heated in a water-bath at 55° C. for 15 minutes and was then vacuum filtered to remove triphenylcarbinol. The filtrate was evaporated to dryness under reduced pressure and the residue was taken up in ethanol. The mixture was evaporated to dryness under reduced pressure and the residue was dissolved in 3 ml of methanol. The solution was diluted with 30 ml of ether and the mixture was vacuum filtered. The 201 mg of recovered raw product were dissolved in 1 ml of hot methanol and 5 ml of ether were added thereto to cause precipitation. The mixture was vacuum filtered to obtain 171 mg of the syn isomer of 3-acetoxymethyl-7-[2-(2-amino-4-thiazolyl)-2-{2-(1-methyl-5-tetrazolyl)-thioethoxyimino}-acetamido]-ceph-3-eme-4-carboxylic acid.

Analysis: $C_{19}H_{21}O_7N_9S_3$; Calculated: %C 39.10, %H 3.63, %N 21.6, %S 16.48; Found: 38.6, 3.7, 20.9, 16.

RMN Spectrum [$(CD_3)_2SO$]: peaks at 2.03 ppm

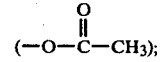

at 4.33 ppm (triplet-=N—O—CH$_2$—) J=6 Hz; at 6.76 ppm (5-proton of thiazole); at 3.91 (singulet =N—CH$_3$).

EXAMPLE 32 syn isomer of 3-acetoxymethyl-7-[2-(2-amino-4-thiazolyl)-2-(2-azidoethoxyimino)-acetamido]-ceph-3-eme-4-carboxylic acid STEP A: syn isomer of sodium 2-(2-tritylamino-4-thiazolyl)-2-(2-bromoethoxyimino)-acetate 28.2 g of ethyl 2-(2-tritylamino-4-thiazolyl)-2-(2-bromoethoxyimino)-acetate were added to a mixture of 6 g of sodium hydroxide pastilles in 280 ml of absolute ethanol and the mixture was stirred at room temperature for 65 hours and was vacuum filtered. The recovered product was washed with ethanol and dried under reduced pressure to obtain 29.2 g of the syn isomer of sodium 2-(2-tritylamino-4-thiazolyl)-2-(2-bromoethoxyimino)-acetate, solvated at 12%.

STEP B: syn isomer of 2-(2-tritylamino-4-thiazolyl)-2-(2-azidoethoxyimino)-acetic acid A mixture of 24.8 g of sodium 2-(2-tritylamino-4-thiazolyl)-2-(2-bromoethoxyimino)-acetate, 125 ml of dimethylformamide and 7.6 g of tetramethylguanidine azidure was stirred at 50° C. in a water bath for 60 minutes and after the addition of another 0.8 g of tetramethylguanidine azidure, the mixture was stirred for 45 minutes to obtain a lipid brown solution. The mixture was cooled to room temperature and 500 ml of water and 50 ml of 2 N hydrochloric acid were added thereto. The mixture was vacuum filtered and the recovered product was empasted 3 times with water and then triturated with methylene chloride. The filtrate was decanted and was washed with water, dried and evaporated under reduced pressure to a volume of 50 ml. 250 ml of ether were slowly added thereto and the mixture was vacuum filtered to obtain 15.58 g of the syn isomer of 2-(2-tritylamino-4-thiazolyl)-2-(2-azidoethoxyimino)-acetic acid.

STEP C: syn isomer of diethylamine 3-acetoxymethyl-7-[2-(2-tritylamino-4-thiazolyl)-2-(2-azidoethoxyimino)-acetamido]-ceph-3-eme-4-carboxylate A mixture of 9.84 g of the product of Step B, 2.93 g of 1-hydroxy-1H-benzotriazol, 4.88 g of dicyclohexylcarbodiimide and 130 ml of anhydrous methylene chloride was stirred for 20 hours at room temperature and was vacuum filtered to remove dicyclohexylurea. The filtrate was washed with aqueous sodium bicarbonate solution, then with water, was dried and evaporated to dryness under reduced pressure. The residue was taken up in ethyl acetate and after cooling the mixture at 0° C. for 30 minutes, the mixture was vacuum filtered to obtain 7.31 g of 1-hydroxy-1H-benzotriazole 2-(2-tritylamino-4-thiazolyl)-2-(2-azidoethoxyimino)-acetate. Another 1.5 g of the product were recovered by evaporation of the filtrate.

A mixture of 2.54 g of 7-amino-cephalosporanic acid, 25 ml of anhydrous methylene chloride and 2.6 ml of triethylamine was stirred at room temperature for 15 minutes and then 6.02 g of 1-hydroxy-1H-benzotriazole 2-(2-tritylamino-4-thiazolyl)-2-(2-azidoethoxyimino)-acetate were added thereto. The mixture was stirred at room temperature for 45 hours and 25 ml of water and 5 ml of N hydrochloric acid were added thereto. The decanted organic phase was washed with water, dried and evaporated to dryness under reduced pressure. The residue was taken up in 30 ml of ethyl acetate and 2.4 ml of diethylamino were added to the solution. The mixture was cooled at 0° C. and was vacuum filtered to obtain 5.9 g of the syn isomer of diethylamine 3-acetoxymethyl-7-[2-(2-tritylamino-4-thiazolyl)-2-(2-azidoethoxyimino)-acetamido]-ceph-3-eme-4-carboxylate.

STEP D: syn isomer of 3-acetoxymethyl-7-[2-(2-amino-4-thiazolyl)-2-(2-azidoethoxyimino)-acetamido]-ceph-3-eme-4-carboxylic acid A mixture of 1.238 g of the product of Step C and 6 ml of 70% aqueous formic acid was stirred at 50° C. for 15 minutes and was the vacuum filtered to remove triphenylcarbinol. The filtrate was evaporated to dryness under reduced pressure and the residue was taken up in water with efflorescence. The mixture was vacuum filtered and the recovered product was dried to obtain 0.358 g of the syn isomer of 3-acetoxymethyl-7-[2-(2-amino-4-thiazolyl)-2-(2-azidoethoxyimino)-acetamido]-ceph-3-eme-4-carboxylic acid.

EXAMPLE 33 syn isomer of sodium 3-acetoxymethyl-7-[2-(2-amino-4-thiazolyl)-2-(2-azidoethoxyimino)-acetamido]-ceph-3-eme-4-carboxylate 0.385 g of the acid of Example 32 was added to 1 ml of a molar solution of sodium acetate in methanol to obtain a lipid solution to which 5 ml of ethanol were slowly added. The mixture was vacuum filtered and the recovered product was rinsed with ethanol and then ether to obtain 0.215 g of the syn isomer of sodium 3-acetoxymethyl-7-[2-(2-amino-4-thiazolyl)-2-(2-azidoethoxyimino)-acetamido]-ceph-3-eme-4-carboxylate.

Analysis: $C_{17}H_{17}O_7N_8S_2Na$; molecular weight=532.49; Calculated: %C 38.4, %H 3.2, %N 21.0, %S 12.0; Found: 38.3, 3.2, 20.4, 12.1.

RMN Spectrum [(CD₃)₂SO]: peaks at 1.98 ppm

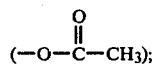

at 4.18 ppm (triplet-=N—O—C$\underline{H}_2$—) J=5 Hz; at 6.76 (5-proton of thiazole).

EXAMPLE 34 syn isomer of 3-acetoxymethyl-7-[2-(2-amino-4-thiazolyl)-2-(2-aminoethoxyimino)-acetamido]-ceph-3-eme-4-carboxylic acid STEP A: syn isomer of 3-acetoxymethyl-7-[2-(2-tritylamino-4-thiazolyl)-2-(2-aminoethoxyimino)-acetamido]-ceph-3-eme-4-carboxylic acid A mixture of 0.752 g of the compound of Example 32, 4 ml of dimethylformamide and 0.7 ml of anhydrous triethylamine had hydrogen sulfide bubbled therethrough for 15 minutes and then 40 ml of water followed by 0.7 ml of acetic acid were added thereto. The mixture was vacuum filtered to obtain 0.707 g of raw syn isomer of 3-acetoxymethyl-7-[2-(2-tritylamino-4-thiazolyl)-2-(2-aminoethoxyimino)-acetamido]-ceph-3-eme-4-carboxylic acid.

STEP B: syn isomer of 3-acetoxymethyl-7-[2-(2-amino-4-thiazolyl)-2-(2-aminoethoxyimino)-acetamido]-ceph-3-eme-4-carboxylic acid A mixture of 1.054 g of the product of Step A and 5 ml of 70% aqueous formic acid was heated at 50° C. for 15 minutes and the mixture was vacuum filtered to remove triphenylcarbinol. The filtrate was evaporated to dryness under reduced pressure and the residue was taken up in water. The mixture was filtered and the filtrate was evaporated to dryness and the residue was taken up in ethanol. After efflorescence, the mixture was vacuum filtered to obtain 0.125 g of the syn isomer of 3-acetoxymethyl-7-[2-(2-amino-4-thiazolyl)-2-(2-aminoethoxyimino)-acetamido]-ceph-3-eme-4-carboxylic acid.

EXAMPLE 35 syn isomer of sodium 3-acetoxymethyl-7-[2-(2-amino-4-thiazolyl)-2-(2-aminoethoxyimino)-acetamido]-ceph-3-eme-4-carboxylate The product of Example 34 was dissolved in 0.2 ml of a molar solution of sodium acetate in methanol and 0.4 ml of ethanol was slowly added thereto. The mixture was vacuum filtered and the filtrate was evaporated to dryness under reduced pressure. The residue was taken up in ethanol and after efflorescence, the mixture was vacuum filtered to obtain 0.047 g of the syn isomer of sodium 3-acetoxymethyl-7-[2-(2-amino-4-thiazolyl)-2-(2-aminoethoxyimino)-acetamido]-ceph-3-eme-4-carboxylate.

EXAMPLE 36 syn isomer of 3-[(1-methyl-1H-tetrazol-5-yl)-thiomethyl]-7-[2-(2-amino-4-thiazolyl)-2-(2-azidoethoxyimino)-acetamido]-ceph-3-eme-carboxylic acid STEP A: syn isomer of 3-[(1-methyl-1H-tetrazol-5-yl)-thiomethyl]-7-[2-(2-tritylamino-4-thiazolyl)-2-(2-azidoethoxyimino)-acetamido]-ceph-3-eme-4-carboxylic acid A mixture of 0.652 g of 3-[(1-methyl-1H-tetrazol-5-yl)-thiomethyl]-7-amino-ceph-3-eme-4-carboxylic acid, 6.5 ml of methylene chloride and 0.56 ml of triethylamine was stirred at room temperature for 15 minutes and then 1.29 g of 1-hydroxy-1H-benzotriazole 2-(2-azidoethoxyimino)-2-(2-tritylamino-4-thiazolyl)-acetate were added thereto. The mixture was stirred at room temperature for 20 hours and then 10 ml of water and 3 ml of 2 N hydrochloric acid were added thereto. The decanted organic phase was washed with water, dried and evaporated to dryness under reduced pressure. The residue was taken up in 5 ml of ethyl acetate and 10 ml of ether were added thereto. The mixture was stirred for 30 minutes at room temperature and was vacuum filtered to obtain 1.416 g of raw syn isomer of 3-[(1-methyl-1H-tetrazol-5-yl)-thiomethyl]-7-[2-(2-tritylamino-4-thiazolyl)-2-(2-azidoethoxyimino)-acetamido]-ceph-3-eme-4-carboxylic acid.

STEP B: syn isomer of 3-[(1-methyl-1H-tetrazol-5-yl)-thiomethyl]-7-[2-(2-amino-4-thiazolyl)-2-(2-azidoethoxyimino)-acetamido]-ceph-3-eme-4-carboxylic acid A mixture of 1.336 g of the product of Step A and 7 ml of formic acid were stirred at 50° C. for 15 minutes and was vacuum filtered to remove triphenylcarbinol. The filtrate was evaporated to dryness and the residue was taken up in water. After efflorescence, the mixture was vacuum filtered to obtain 0.77 g of raw product which was dissolved in minimum of aqueous 10% sodium bicarbonate solution. 0.77 g of activated carbon were added thereto and the mixture was vacuum filtered. Formic acid was added to the filtrate to adjust the pH to 2 and the mixture was vacuum filtered to obtain 0.171 g of syn isomer of 3-[(1-methyl-1H-tetrazol-5-yl)-thiomethyl]-7-[2-(2-amino-4-thiazolyl)-2-(2-azidoethoxyimino)-acetamido]-ceph-3-eme-4-carboxylic acid.

EXAMPLE 37 syn isomer of sodium 3-[(1-methyl-1H-tetrazol-5-yl)-thiomethyl]-7-[2-(2-amino-4-thiazolyl)-2-(2-azidoethoxyimino)-acetamido]-ceph-3-eme-4-carboxylate 1 ml of ethanol was added to a solution of 0.162 g of the product of Example 36 in 0.3 ml of a molar solution of sodium bicarbonate in water and the mixture was vacuum filtered. The filtrate was evaporated to dryness undere reduced pressure and the residue was taken up in ethanol. After efflorescence, the mixture was vaccum filtered to obtain 0.09 g of the syn isomer of sodium 3-[(1-methyl-1H-tetrazol-5-yl)-thiomethyl]-7-[2-(2-amino-4-thiazolyl)-2-(2-azidoethoxyimino)-acetamido]-ceph-3-eme-4-carboxylate.

Analysis: $C_{17}H_{17}O_5N_{12}S_3Na$; molecular weight=588.584; Calculated: %C 34.7, %H 2.9, %N 28.5, %S 16.3; Found: 34.5, 3.2, 25.3, 15.3.

RMN Spectrum [$(CD_3)_2SO$]: peaks at 3.9 ppm (—NCH$_3$); at 6.76 ppm (5-proton of thiazole); at 9.35–9.48

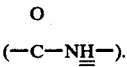

EXAMPLE 38 syn isomer of 3-[(1-methyl-1H-tetrazol-5-yl)-thiomethyl]-7-[2-(2-amino-4-thiazolyl)-2-(2-aminoethoxyimino)-acetamido]-ceph-3-eme-4-carboxylic acid STEP A: syn isomer of sodium 3-[(1-methyl-1H-tetrazol-5-yl)-thiomethy]-7-[2-(2-tritylamino-4-thiazolyl)-2-(2-azidoethoxyimino)-acetamido]-ceph-3-eme-4-carboxylic acid A mixture of 8.47 g of the syn isomer of 2-(2-tritylamino-4-thiazolyl)-2-(2-azidoethoxyimino)-acetic acid, 50 ml of methylene chloride and 1.93 g of dicyclohexylcarbodiimide was stirred at room temperature for one hour and was vacuum filtered to remove dicyclohexylurea. The filtrate was added over 20 minutes to a mixture of 3.07 g of 3-[(1-methyl-1H-tetrazol-5-yl)-thiomethyl]-7-amino-ceph-3-eme-4-carboxylic acid, 40 ml of anhydrous methylene chloride and 3.9 ml of triethylamine and the mixture was stirred for one hour and was evaporated to dryness under reduced pressure. The residue was taken up in 50 ml of ethyl acetate at 20° C. and the mixture was acidified with 0.2 ml of acetic acid. The mixture was vacuum filtered and the filtrate was washed with N hydrochloric acid and then with water until the wash waters were neutral. The organic phase was then dried and reduced to a volume of 50 ml. 1.7 ml of diethylamine were added thereto and crystallization occurred. The mixture was vacuum filtered and 115 ml of isopropyl ether were added to the filtrate. The mixture was vacuum filtered to obtain 7.12 g of a diethylamine salt and 5.9 g of the salt were dissolved with stirring in a mixture of 60 ml of water, 60 ml of methylene chloride and 3.5 ml of 2 N hydrochloric acid. The decanted organic phase was washed with water, dried and evaporated to dryness under reduced pressure and the residue was taken up in 20 ml of isopropyl ether. The mixture was vacuum filtered to obtain 5.6 g of free acid which were dissolved in a mixture of 9.5 ml of methanol and 6.7 ml of a molar solution of sodium acetate in methanol. 27 ml of isopropanol containing 25% of ethanol was added thereto followed by the addition of 270 ml of isopropanol and the mixture was vacuum filtered to obtain 4.21 g of the syn isomer of sodium 3-[(1-methyl-1H-tetrazol-5-yl)thiomethyl-7-[2-(2-tritylamino-4-thiazolyl)-2-(2-azidoethoxyimino)-acetamido]-ceph-3-eme-4-carboxylate.

STEP B: syn isomer of 3-[(1-methyl-1H-tetrazol-5-yl)-thiomethyl]-7-[2-(2-tritylamino-4-thiazolyl)-2-(2-aminoethoxyimino)-acetamido]-ceph-3-eme-4-carboxylic acid 20 ml of water were slowly added to a solution of 3.91 g of the product of Step A in 39 ml of dimethylformamide followed by the addition of 9.75 ml of triethylamine and then hydrogen sulfide was bubbled through the mixture for 45 minutes. 3.9 ml of triethylamine were added thereto and hydrogen sulfide bubbling was continued for 15 minutes. The mixture was poured in diluted hydrochloric acid at 10° C. and the mixture was stirred at 30° C. for 15 minutes and was then cooled. The mixture was vacuum filtered and the recovered product was washed with water until the wash water was neutral and rinsed with ether to obtain 2 g of the syn isomer of 3-[(1-methyl-1H-tetrazol-5-yl)-thiomethyl]-7-[2-(2-tritylamino-4-thiazolyl)-2-(2-aminoethoxyimino)-acetamido]-ceph-3-eme-4-carboxylic acid.

STEP C: syn isomer of 3-[(1-methyl-1H-tetrazol-5-yl)-thiomethyl]-7-[2-(2-amino-4-thiazolyl)-2-(2-aminoethoxyimino)acetamido]-ceph-3-eme-4-carboxylic acid A mixture of 2 g of the product of Step B and 5 ml of formic acid was heated with stirring to 40°–45° C. and after the addition of 5 ml of water, the mixture was stirred at 40°–45° C. for 15 minutes and was then cooled. The mixture was vacuum filtered to remove triphenylcarbinol and the filtrate was evaporated to dryness under reduced pressure. The residue was taken up in 10 ml of ethanol with efflorescence and the mixture was vacuum filtered. The recovered product was rinsed with ethanol and then with ether to obtain 1.36 g of raw product which was taken up in 15 ml of 2 N hydrochloric acid. The mixture was vacuum filtered and the filtrate was adjusted to a pH of 4 with 3 ml of an aqueous molar solution of lithium acetate and then with aqueous lithium hydroxide. The mixture was vacuum filtered and the filtrate was evaporated to dryness under reduced pressure. The residue was taken up in 30 ml of ethanol with efflorescence and the mixture was vacuum filtered to obtain 515 mg of syn isomer of 3-[(1-methyl-1H-tetrazol-5-yl)-thiomethyl]-7-[2-(2-amino-4-thiazolyl)-2-(2-aminoethoxyimino)-acetamido]-ceph-3-eme-4-carboxylic acid. The mother liquors were evaporated to dryness to obtain another 133 mg of the said product and the combined products were treated again in the same manner to obtain a final yield of 430 mg of the product in the form of a white powder.

RMN Spectrum [$(CD_3)_2SO$]: peaks at 6.86 ppm (5-proton of thiazol).

EXAMPLE 39

Trifluoroacetate of syn isomer of 3-acetoxymethyl-7-[2-(2-amino-4-thiazolyl)-2-(2-iodoethoxyimino)-acetamido]-ceph-3-eme-4-carboxylic acid

STEP A: syn isomer of ethyl 2-(2-iodoethoxyimino)-2-(2-tritylamino-4-thiazolyl)-acetate A mixture of 6 g of the syn isomer of ethyl 2-(2-bromoethoxyimino)-2-(2-tritylamino-4-thiazolyl)-acetate, 60 ml of methyl ethyl ketone and 2.141 g of sodium iodide was refluxed for 70 minutes and was then evaporated to dryness under reduced pressure. The residue was taken up in 120 ml of methylene chloride and the solution was washed 5 times with 40 ml of water. Each of the wash waters were reextracted with 2 ml of methylene chloride and the combined organic phase were dried and evaporated to dryness. The resin residue was added to ether and the solution was evaporated to dryness under reduced pressure to obtain 6.22 g of the syn isomer of ethyl 2-(2-iodoethoxyimino)-2-(2-tritylamino-4-thiazolyl)acetate melting at 110° C.

STEP B: syn isomer of 2-(2-iodoethoxyimino)-2-(2-tritylamino-4-thiazolyl)-acetic acid 5.5 ml of a 2 N sodium hydroxide solution was added dropwise under an inert atmosphere to a mixture of 6.7 g of the product of Step A in 5.5 ml of dioxane and 44 ml of absolute ethanol and after the addition of 7 ml of absolute ethanol the mixture was stirred overnight to room temperature and was vacuum filtered. The recovered product was rinsed twice with 3 ml of a 4-1 ethanol-dioxane mixture and was then empasted with ether. The product was placed in a mixture of 100 ml of water and 100 ml of chloroform and the pH was adjusted to 2 by addition of N hydrochloric acid. The decanted organic phase was washed with an aqueous saturated sodium chloride solution, was dried and evaporated to dryness under reduced pressure. The residue was dissolved in 35 ml of dichloroethane at 40° C. and crystallization was induced. The mixture stood at room temperature for 72 hours and was vacuum filtered. The recovered product was rinsed and dried to obtain 5.4 g of the syn isomer of 2-(2-iodoethoxyimino)-2-(2-tritylamino-4-thiazolyl)-acetic acid solvated with dichloroethane melting at 161° C. (= to 4.61 g of pure product).

Analysis: $C_{26}H_{22}O_3N_3SI$: molecular weight=583.35; Calculated: %N 6.16, %S 4.70; Found: 5.9, 4.8.

U.V. Spectrum (0.1 N HCl in ethanol): max. at 278 nm; $E_1^1 = 235$

RMN Spectrum (deuterochloroform): peak at 6.58 ppm (5-proton of thiazole):

STEP C: syn isomer of benzhydryl 3-acetoxymethyl-7-[2-(2-tritylamino-4-thiazolyl)-2-(2-iodoethoxyimino)-acetamido]-ceph-3-eme-4-carboxylate 5 ml of a solution of 0.5 M (103 g/l) of dicyclohexylcarbodiimide in methylene chloride were added dropwise under an inert atmosphere to a mixture of 1.28 g of the solvate of Step B (=1.09 g of pure product), 1.45 g of benzhydryl 7-amino-cephalosporonate and 22 ml of anhydrous methylene chloride in an ice bath and the mixture was stirred at 0° to 5° C. for 90 minutes and at 25° C. for one hour. The mixture was vacuum filtered and the filter was rinsed with methylene chloride. The filtrate was evaporated to dryness under reduced pressure at less than 40° C. to obtain 2.8 g of residue which was chromatographed over silica gel. Elution with a 92-8 methylene chloride-ethyl acetate mixture yielded 1.12 g of white syn isomer of benzhydryl 3-acetoxymethyl-7-[2-(2-tritylamino-4-thiazolyl)-2-(2-iodoethoxyimino)-acetamido]-ceph-3-eme-4-carboxylate.

U.V. Spectrum (0.1 N HCl in ethanol): Max. at 269; $E_1^1 = 209$

I.R. Spectrum (chloroform): absorption at 1791 $cm^{-1}$ (β-lactam); at 1042 $cm^{-1}$ (—C=NOR); at 1638 $cm^{-1}$ (C=C).

RMN Spectrum (deuterochloroform): peak at 6.75 ppm (5-proton of thiazole).

STEP D: Trifluoroacetate of syn isomer of 3-acetoxymethyl-7-[2-(2-amino-4-thiazolyl)-2-(2-iodoethoxyimino)-acetamido]-ceph-3-eme-4-carboxylic acid A mixture of 960 mg of the product of Step C and 10 ml of pure trifluoroacetic acid was stirred for 3 minutes at room temperature, cooled for 1 minutes in an ice bath and was diluted with 100 ml of iced isopropyl ether to induce precipitation. The mixture was stirred at room temperature for 10 minutes and was vacuum filtered. The product was rinsed with isopropyl ether and then with ether and was dried under reduced pressure to obtain 460 mg of the trifluoroacetate of syn isomer of 3-acetoxymethyl-7-[2-(2-amino-4-thiazolyl)-2-(2-iodoethoxyimino)-acetamido]-ceph-3-eme-4-carboxylic acid melting at 214° C.

Analysis: $C_{17}H_{18}N_5O_7SI \cdot CF_3COOH$; Calculated: %N 9.87, %S 9.04; Found: 9.7, 9.2.

U.V. Spectrum (0.1 N HCl in ethanol): Max. at 262 nm; $E_1^1 = 290$

RMN Spectrum [(CD$_3$)$_2$SO]: peak at 6.83 ppm (5-proton of thiazole).

EXAMPLE 40

Trifluoroacetate and iodide syn isomer of
N-/2-{2-(2-carboxy-3-methyl-8-oxo-5-thia-1-azabicyclo/4,2,0/-oct-2-en-7-yl)amino}-1-(2-amino-4-thiazolyl)-2-oxoethylimino/oxyethylpyridinium

STEP A: syn isomer of benzhydryl 3-methyl-7-[2-(2-tritylamino-4-thiazolyl)-2-(2-bromoethoxyimino)-acetamido]-ceph-3-eme-4-carboxylate A mixture of 536 mg of syn isomer of 2-(2-bromoethoxyimino)-2-(2-tritylamino-4-thiazolyl)-acetic acid, 380 mg of benzhydryl 3-desacetoxy-7-amino-cephalosporanate and 6 ml of anhydrous methylene chloride was held under an inert atmosphere in an ice bath for 5 minutes and 230 mg of dicyclohexylcarbodiimide were added thereto. The mixture was rinsed with 2 ml of methylene chloride and was allowed to stand at 0° to 5° C. for 2 hours and at room temperature for one hour. The mixture was vacuum filtered and the insolubles (111 mg) were washed 3 times with methylene chloride and the filtrate was evaporated to dryness to obtain 1.02 g of resin. The product was chromatographed over 100 g of silica gel and was eluted with a 17-3 benzene-ethyl acetate mixture to obtain 548 mg of the syn isomer of benzhydryl 3-methyl-7-[2-(2-tritylamino-4-thiazolyl)-2-(2-bromoethoxyimino)-acetamido]-ceph-3-eme-4-carboxylate as a resin with an Rf=0.27-0.28 (17-3 benzene-ethyl acetate).

RMN Spectrum: peaks at 6.75 ppm (5-proton of thiazole); at 3.58 ppm (triplet center—C$\underline{H}_2$-Br) J=7 Hz.

STEP B: syn isomer of N-[2-{2-(2-diphenylmethylcarboxy-3-methyl-8-oxo-5-thia-1-azabicyclo-[4,2,0]-oct-2-en-7-yl)amino}-1-(2-tritylamino-4-thiazolyl)-2-oxoethyliminooxy]ethylpyridinium iodide A mixture of 500 mg of the product of Step A, 115 mg of pyridine hydroiodide and 5 ml of pyridine under an inert atmosphere was heated at 50° C. for 15 hours and was then evaporated to dryness under reduced pressure at less than 40° C. The residue was taken up in methanol and evaporated to dryness 4 times to remove residual pyridine and was dried under reduced pressure to obtain 620 mg of raw product. The latter was chromatographed over silica gel and was eluted with an 85-15 chloroform-methanol mixture to obtain 348 mg of the syn isomer of N-[2-{2-(2-diphenylmethylcarboxy-3-methyl-8-oxo-5-thia-1-azabicyclo-[4,2,0]-oct-2-en-7-yl)-amino}-1-(2-tritylamino-4-thiazolyl)-2-oxoethyliminooxy]-ethylpyridinium iodide in the form of a resin.

RMN. Spectrum peaks at 6.81 ppm (5-proton of thiazole)

STEP C: Trifluoroacetate and iodide of syn isomer of N-/2-{2-(2-carboxy-3-methyl-8-oxo-5-thia-1-azabicyclo-[4,2,0]oct-2-en-7-yl)-amino}-1-(2-amino-4-thiazolyl)-2-oxoethylimino]-oxyethyl-pyridinium A mixture of 300 mg of the product of Step B in 3 ml of pure trifluoroacetic acid was stirred at room temperature for 3 minutes and was cooled in an ice bath for 20 seconds. 40 ml of an iced 1-1 isopropyl ether-Essence B (b.p.=65°-75° C.) mixture were added thereto and the mixture was vacuum filtered. The recovered product was rinsed with isopropyl ether, then ether and dried to obtain 152 mg of the trifluoroacetate and iodide of syn isomer of N-/2-{2-(2-carboxy-3-methyl-8-oxo-5-thia-1-azabicyclo-/4,2,0/-oct-2-en-7-yl)amino}-1-(2-amino-4-thiazolyl)-2-oxoethylimino/-oxyethyl-pyridinium in the form of a powder melting at ≃ 222° C. with an Rf=0.05 (70-35-10 acetic, acid-ethyl, acetate-water).

U.V. Spectrum (0.1 N HCl in ethanol): max. at 260 nm; $E_1^1 = 355$

I.R. Spectrum: absorption at 1768 cm$^{-1}$ (β-lactam); at 1038 cm$^{-1}$ (O=NOR).

RMN Spectrum [(CD$_3$)$_2$SO]: peak at 6.76 ppm (5-proton of thiazole).

EXAMPLE 41

Trifluoroacetate of syn isomer of 3-acetoxymethyl-7-[2-(2-amino-4-thiazolyl)-2-(2-dimethylaminoethoxyimino)-acetamido]-ceph-3-eme-4-carboxylic acid

STEP A: syn isomer of 2-(2-tritylamino-4-thiazolyl)-2-(2-dimethylaminoethoxyimino)-acetic acid hydroiodide A mixture of 120 ml of a 9-1 chloroform-dimethylamine mixture and 10 g of the syn isomer of 2-(2-tritylamino-4-thiazolyl)-2-(2-iodoethoxyimino)-acetic acid was stirred at room temperature for 3 hours and was then evaporated to dryness under reduced pressure at less than 40° C. The residue was triturated with 100 ml of isopropyl ether and then mixture was stirred for 15 minutes and was vacuum filtered. The recovered product was rinsed and taken up in 50 ml of acetone. The mixture was refluxed for 5 minutes and was vacuum filtered at room temperature. The filtrate was dried and evaporated to dryness under reduced pressure to obtain 9.33 g of residue. The latter was taken up in 46 ml of water and the mixture was stirred and vacuum filtered. The product was rinsed and taken up in 80 ml of acetone. The mixture was stirred and vacuum filtered and the recovered product was dried under reduced pressure to obtain the syn isomer of 2-(2-tritylamino-4-thiazolyl)-2-(2-dimethylaminoethoxyimino)-acetic acid hydroiodide melting at 208°-210° C. (decomposition).

RMN Spectrum [D$_2$O+C$_5$D$_5$N]: peaks at 4.55 ppm (triplet center-=N—OC$\underline{H}_2$—) I=5 Hz; at 6.98 ppm (5-proton of thiazole-singulet); at 7.53 (—C(PH$_3$singulet).

| U.V. Spectrum (0.1N HCl in ethanol): | | |
|---|---|---|
| Inflex. at 270 nm | $E_1^1 = 271$ | |
| Max. at 275 nm | $E_1^1 = 280$ | ε = 14,000 |
| Inflex. at 284 nm | $E_1^1 = 260$ | |

STEP B: syn isomer of benzhydryl 3-acetoxymethyl-7-[2-(2-tritylamino-4-thiazolyl)-2-(2-dimethylaminoethoxyimino)acetamido]-ceph-3-eme-4-carboxylate 304 mg of triethylamine hydrochloride were added to a solution of 1 g of the product of Step A, 15 ml of chloroform and 1.5 ml of methanol and the mixture was heated at 60° C. for 5 minutes and was then evaporated to dryness. The residue was taken up in 15 ml of chloroform and 2 ml of a solution of 1.25 g of pivaloyl chloride in 10 ml of chloroform were added dropwise to the mixture while cooling to 0° to 5° C. in an ice bath. The temperature returned to room temperature over about 2 hours and 1.1 g of benzhydryl 7-amino-cephalosporanate were added to the mixture. After 90 minutes, the mixture was evaporated to dryness under reduced pressure and the residue was chromatographed over silica gel. Elution with chloroform containing 5% of methanol yielded 430 mg of the syn isomer of benzhydryl 3-acetoxymethyl-7-[2-(2-tritylamino-4-thiazolyl)-2-(2-dimethylaminoethoxyimino)-acetamido]-ceph-3-eme-4-carboxylate.

STEP C: Trifluoroacetate of syn isomer of 3-acetoxymethyl-7-[2-(2-amino-4-thiazolyl)-2-(2-dimethylaminoethoxyimino)acetamido]-ceph-3-eme-4-carboxylic acid A mixture of 100 mg of the product of Step B and 1 ml of trifluoroacetic acid was stirred for 3 minutes at room temperature and ether was added thereto to cause precipitation. The mixture was filtered and the recovered product was added to 0.2 ml of methanol. 2 ml of ether were added to the mixture and was filtered. The product was empasted with chloroform and the mixture was vacuum filtered. The product was rinsed with chloroform and with ether to obtain 40 mg of the trifluoroacetate of syn isomer of 3-acetoxymethyl-7-[2-(2-amino-4-thiazolyl)-2-(2-dimethylaminoethoxyimino)acetamido]-ceph-3-eme-4-carboxylic acid melting at 230° C.

RMN Spectrum [(CD$_3$)$_2$SO]: peak at 6.8 ppm (5-proton of thiazole-singulet).

| U.V. Spectrum (ethanol): | | |
|---|---|---|
| max. at 234 nm | $E_1^1 = 305$ | $\epsilon = 15{,}600$ |
| Inflex. at 254 nm | $E_1^1 = 247$ | $\epsilon = 12{,}650$ |
| Inflex at 296 nm | $E_1^1 = 103$ | $\epsilon = 5{,}300$ |
| U.V. Spectrum (0.1N HCl in ethanol): | | |
| max. at 260 nm | $E_1^1 = 279$ | $\epsilon = 14{,}300$ |
| Inflex. at 276 nm | $E_1^1 = 243$ | |

EXAMPLE 42

Trifluoroacetate of syn isomer of 3-acetoxymethyl-7-[2-(2-amino-4-thiazolyl)-2-(2-pyridylethoxyimino)-acetamido]-ceph-3-eme-4-carboxylic acid in form of pyridinium internal salt

STEP A: syn isomer of 2-(2-tritylamino-4-thiazolyl)-2-(2-pyridylethoxyimino)-acetic acid (pyridinium internal salt)

A mixture of 5 g of syn isomer of 2-(2-tritylamino-4-thiazolyl)-2-(2-iodoethoxyimino)-acetic acid solvated with dichloroethane (=4.27 g of pure product) and 30 ml of pyridine was heated at 60° C. for 24 hours and then stood at room temperature for 56 hours. The mixture was vacuum filtered and the recovered product was rinsed with pyridine and then ether and dried to obtain 1.66 g of the syn isomer of 2-(2-tritylamino-4-thiazolyl)-2-(2-pyridylethoxyimino)-acetic acid (pyridinium internal salt) melting at 250° C. (decomposition).

RMN Spectrum (1 D$_2$O-1 CD$_3$

peaks at 6.8 ppm (5-proton of thiazole); at 7.5 to 8 ppm (pyridyl proton); at 4.58 to 5.08 ppm (=NO—CH$_2$—CH$_2$—).

U.V. Spectrum (0.1 N HCl in ethanol): max. at 260 nm; $E_1^1 = 324$

I.R. Spectrum (Nujol): absorption of 1639 cm$^{-1}$ (COO$^-$); at 1583 cm$^{-1}$ (C=C); at 1523 cm$^{-1}$ (C=N).

STEP B: syn isomer of benzhydryl 3-acetoxymethyl-7-[2-(2-tritylamino-4-thiazolyl)-2-(2-pyridylethoxyimino)-acetamido]-ceph-3-eme-4-carboxylate iodide A mixture of 540 mg of the product of Step A, 210 mg of pyridine hydroiodide, 420 mg of dicyclohexylcarbodiimide, 350 mg of benzhydryl 3-acetoxymethyl-7-amino-ceph-3-eme-4-carboxylate and 5 ml of anhydrous dimethylformamide was stirred at room temperature for 20 minutes and was then vacuum filtered to remove dicyclohexylurea. The filter was rinsed with dimethylformamide and the filtrate was poured into 60 ml of ether after which a gum formed. The mixture was stirred at room temperature for 5 minutes and the gum was recovered by decanting. The gum was triturated with 60 ml of ether and the mixture was vacuum filtered to obtain 754 mg of raw product. The latter was stirred with 1.6 g of magnesium silicate in 7.5 ml of dichloroethane for 20 minutes and the mixture was vacuum filtered. The filter was rinsed with 0.5 ml of dichloroethane and the filtrate was evaporated to dryness to obtain 368 mg of the syn isomer of benzhydryl 3-acetoxymethyl-7-[2-(2-tritylamino-4-thiazolyl)-2-(2-pyridylethoxyimino)-acetamido]-ceph-3-eme-4-carboxylate iodide.

STEP C: Trifluoroacetate of syn isomer of 3-acetoxymethyl-7-[2-(2-amino-4-thiazolyl)-2-(2-pyridylethoxyimino)-acetamido]-ceph-3-eme-4-carboxylic acid A mixture of 368 mg of the product of Step B and 3 ml of pure trifluoroacetic acid was stirred for 3 minutes at room temperature and was then rapidly vacuum filtered. The filtrate was poured into 40 ml of ether and after stirring for 5 minutes, the mixture was vacuum filtered. The hygroscopic product was rinsed with ether and taken up in 0.35 ml of methanol. 4 ml of ether was added thereto and the mixture was vacuum filtered. The product was rinsed with ether to obtain 140 mg of the trifluoroacetate of syn isomer of 3-acetoxymethyl-7-[2-(2-amino-4-thiazolyl)-2-(2-pyridylethoxyimino)-acetamido]-ceph-3-eme-4-carboxylic acid melting at 205° C. (decomposition).

RMN Spectrum (DMSO): peaks at 2.06 ppm (OAc); at 6.86 ppm (5-proton of thiazole); 8.9–9.1 ppm (2- and 6-hydrogens of pyridyl); at 8.55 to 8.78 ppm (4-hydrogen of pyridyl); at 8.03 to 8.26 ppm (3- and 5-hydrogens of pyridyl).

U.V. Spectrum (0.1 N HCl in ethanol): max. at 260 nm; $E_1^1 = 318$

I.R. Spectrum (Nujol): absorption at 1777 cm$^{-1}$ ($\beta$-lactam); at 1740 cm$^{-1}$ (OAc); at 1633 cm$^{-1}$ (COO$^-$); at 1037 cm$^{-1}$ (—C=NOR).

EXAMPLE 43

Trifluoroacetic of syn isomer of 3-acetoxymethyl-7-[2-(2-amino-4-thiazolyl)-2-(2-imidazol-1-yl-ethoxyimino)-acetamido]-ceph-3-eme-4-carboxylic acid

STEP A: syn isomer of 2-(2-tritylamino-4-thiazolyl)-2-(2-imidazol-1-yl-ethoxyimino)-acetic acid (internal imidazolium salt)

A mixture of 3 g of the syn isomer of 2-(2-tritylamino-4-thiazolyl)-2-(2-iodoethoxyimino)-acetic acid solvated with dichloroethane (=2.56 g of pure acid), 4.2 g of imidazole and 10 ml of dimethylacetamide was stirred for 3 hours at room temperature and after addition of another 10 ml of dimethylacetamide, the mixture was stirred for 40 hours at room temperature. The mixture was poured into 200 ml of isopropyl ether and the mixture was stirred for 30 minutes and was then decanted. The gummy residue was triturated in 200 ml of isopropyl ether and then treated with 300 ml of ether. The mixture was stirred for 30 minutes and was vacuum filtered. The product was rinsed with ether and was then taken up in 30 ml of acetone. The solution was stirred for one hour and was vacuum filtered and the recovered product was rinsed with acetone, with ether and dried to obtain 1.243 g of the syn isomer of 2-(2-tritylamino-4-thiazolyl)-2-(2-imidazol-1-yl-ethoxyimino)-acetic acid (internal imidazolium salt) melting at 280° C. (decomposition).

RMN Spectrum (DMSO): peaks at 4.35 ppm (—N—O—$CH_2$—$CH_2$—N<); at 6.8 ppm (5-proton of thiazole); at 7.82 ppm (imidazolyl).

U.V. Spectrum (0.1 N HCl in ethanol): max. at 277 nm; $E_1^1 = 259$

I.R. Spectrum (Nujol): absorption at 1614 cm$^{-1}$ (COO$^-$); at 1492 cm$^{-1}$ (aromatic); at 1527 cm$^{-1}$ (heterocycle).

STEP B: syn isomer of benzhydryl 3-acetoxymethyl-7-[2-(2-tritylamino-4-thiazolyl)-2-(2-imidazol-1-yl-ethoxyimino)-acetamido]-ceph-3-eme-4-carboxylate A mixture of 780 mg of the product of Step A, 315 mg of pyridine hydroiodide, 630 mg of dicyclohexylcarbodiimide, 600 mg of benzhydryl 3-acetoxymethyl-7-aminoceph-3-eme-4-carboxylate and 6 ml of anhydrous dimethylformamide in an ice water bath was vigorously stirred and the temperature was raised to room temperature. The mixture was stirred for 20 minutes and was then vacuum filtered. The filter was rinsed with dimethylformamide and 120 ml of ether were added to the filtrate. The mixture was stirred for 20 minutes and was then decanted. The gummy residue was triturated with 100 ml of ether and the mixture was stirred for 10 minutes at room temperature and was vacuum filtered. The product was rinsed with ether and was dried to obtain 1.3 g of raw product which was chromatographed over silica gel. Elution with an 8-1-0.5 ethyl acetate-ethanol-water mixture yielded 332 mg of the syn isomer of benzhydryl 3-acetoxymethyl-7-[2-(2-tritylamino-4-thiazolyl)-2-(2-imidazol-1-yl-ethoxyimino)-acetamido]-ceph-3-eme-4-carboxylate.

RMN Spectrum (deuterochloroform): peaks at 2 ppm (OAc); at 6.75 ppm (5-proton of thiazole).

I.R. Spectrum (chloroform): absorption at 1788 cm$^{-1}$ (β-lactam); at 1759 cm$^{-1}$ (ester+OAc); at 1525 cm$^{-1}$ (heterocycle).

STEP C: Trifluoroacetate of syn isomer of 3-acetoxymethyl-7-[2-(2-amino-4-thiazolyl)-2-(2-imidazol-1-yl-ethoxyimino)-acetamido]-ceph-3-eme-4-carboxylic acid A mixture of 230 mg of the product of Step B and 2 ml of pure trifluoroacetic acid was stirred at room temperature for 3 minutes and was the poured into a 1-1 isopropyl ether-ether mixture. The mixture was stirred at room temperature for 20 minutes and was vacuum filtered. The product was rinsed with ether and was taken up in 0.4 ml of methanol. 4 ml of ether were added thereto and the mixture was stirred at room temperature for 10 minutes and was vacuum filtered. The product was rinsed with ether and dried to obtain 140 mg of the trifluoroacetate of syn isomer of 3-acetoxymethyl-7-[2-(2-amino-4-thiazolyl)-2-(2-imidazol-1-yl-ethoxyimino)-acetamido]-ceph-3-eme-4-carboxylic acid melting at 205° C. (decomposition).

RMN Spectrum (DMSO): peaks at 2.03 ppm (OAc); at 6.8 ppm (5-proton of thiazole); at 7.66 and 7.71 ppm (4- and 5-hydrogens of imidazole); at 8.95 ppm (2-hydrogen of imidazole).

U.V. Spectrum (0.1 N HCl in ethanol): max. at 260 nm; $E_1^1 = 271$

EXAMPLE 44

Trifluoroacetate of syn isomer of 3-acetoxymethyl-7-[2-(2-amino-4-thiazolyl)-2-(ethoxycarbonyloxyimino)-acetamido]-ceph-3-eme-4-carboxylic acid

STEP A: syn isomer of diethylamine 3-acetoxymethyl-7-[2-(2-tritylamino-4-thiazolyl)-2-(ethoxycarbonyloxyimino)-acetamido]-ceph-3-eme-4-carboxylate A mixture of 1.67 g of the syn isomer of 3-acetoxymethyl-7-[2-(2-tritylamino-4-thiazolyl)-2-hydroxyimino-acetamido]-ceph-3-eme-4-carboxylic acid, 25 ml of methylene chloride and 0.37 ml of pyridine was stirred under an inert atmosphere until dissolution occured and then 2.7 ml of a molar solution of ethyl chloroformate in methylene chloride was added thereto over 5 minutes while cooling in an ice bath. After 10 minutes at 0° to 5° C., 20 ml of water and 2.7 ml of N hydrochloric acid were added thereto and the decanted organic phase was washed with water until the wash water was neutral, dried and distilled to dryness under reduced pressure. The residue was taken up in 10 ml of ethyl acetate and 0.23 ml of diethylamine were added thereto. 10 ml of isopropyl ether were added thereto and the mixture was vacuum filtered. The recovered product was rinsed with a 1-1 isopropyl ether-ethyl acetate mixture and the isopropyl ether to obtain 1.60 g of product. The latter was dissolved in 5 ml of methylene chloride and 10 ml of ethyl acetate and the solution was evaporated under reduced pressure to a volume of ≃6 ml. The mixture was diluted with 5 ml of isopropyl ether and was vacuum filtered. The product was rinsed as before to obtain 1.47 g of the syn isomer of diethylamine 3-acetoxymethyl-7-[2-(2-tritylamino-4-thiazolyl)-2-(ethoxycarbonyloxyimino)-acetamido]-ceph-3-eme-4-carboxylate.

RMN Spectrum (deuterochloroform): peaks at 2.03 ppm (OAc); at 6.95 ppm (5-proton of thiazole); at 7.66 ppm (trityl); at 4.13–4.25–4.36–4.48 ppm ($CH_2$ of —COO$CH_2$—$CH_3$)

I.R. Spectrum (chloroform): absorption of 1781 cm$^{-1}$ (δ-lactam); at 1740 cm$^{-1}$ (OAc); at 1694 cm$^{-1}$ (amide); at 1634 cm$^{-1}$ (COO$^-$).

STEP B: Trifluoroacetate of syn isomer of 3-acetoxymethyl-7-[2-(2-amino-4-thiazolyl)-2-(ethoxycarbonyloxyimino)-acetamido]-ceph-3-eme-4-carboxylic acid A mixture of 1.43 g of the product of Step A and 5.7 ml of trifluoroacetic acid was stirred at room temperature for 20 minutes and then 57 ml of isopropyl ether were rapidly added thereto. The mixture was stirred for 15 minutes and was then vacuum filtered and the recovered product was rinsed with isopropyl ether to obtain 1.04 g of a raw product. The latter was dissolved in 4 ml of acetone containing 1% of water and 12 ml of isopropyl ether were added thereto. The mixture was filtered to obtain 0.69 g of the trifluoroacetate of syn isomer of 3-acetoxymethyl-7-[2-(2-amino-4-thiazolyl)-2-(ethoxycarbonyloxyimino)-acetamido]-ceph-3-eme-4-carboxylic acid and evaporation of the filtrate yielded another 0.11 g of the said product.

EXAMPLE 45 syn isomer of sodium 3-acetoxymethyl-7-[2-(2-amino-4-thiazolyl)-2-(ethoxycarbonyloxyimino)-acetamido]-ceph-3-eme-4-carboxylic acid A solution of 0.8 g of the product of Example 44 in 4 ml of a molar solution of sodium acetate in methanol and 2 ml of methanol was treated with activated carbon and was diluted with 20 ml of anhydrous ethanol. The mixture was evaporated under reduced pressure to a volume of 10 ml at not more than 30° C. and the mixture was vacuum filtered. The recovered product was rinsed with ethanol and then with ether and the 420 mg of product and 580 mg of previously prepared product were taken up in 5.8 ml of methanol. Then, 1.2 ml of ethanol were slowly added thereto and the mixture was vacuum filtered. The filtrate was diluted with 10 ml of ethanol and was evaporated under reduced pressure at 30° C. maximum to a volume of 5 ml. The mixture was vacuum filtered and the product was rinsed with ether to obtain 460 mg of product. The treatment was repeated to obtain 420 mg of the syn isomer of sodium 3-acetoxymethyl-7-[2-(2-amino-4-thiazolyl)-2-(ethoxycarbonyloxyimino)-acetamido]-ceph-3-eme-4-carboxylic acid.

RMN Spectrum (DMSO): peaks at 1.13–1.25–1.36 ppm and at 4.03–4.16–4.28–4.4 ppm (COOCH$_2$CH$_3$); at 1.98 ppm (OAc); at 7.03 ppm (5-proton of thiazole).

| U.V. Spectrum (0.1N HCl in ethanol): | | |
|---|---|---|
| max. at 259 nm | $E_1^1 = 324$ | $\epsilon = 17{,}350$ |
| Inflex. at 278 nm | $E_1^1 = 252$ | |

I.R. Spectrum (Nujol): absorption at 1763 cm$^{-1}$ (β-lactam); at 1726 cm$^{-1}$ (OAc); at 1609 cm$^{-1}$ (COO$^-$); at 1038 cm$^{-1}$ (—C=N—O—).

EXAMPLE 46

Internal salt of syn isomer of 3-acetoxymethyl-7-[2-(2-amino-4-thiazolyl)-2-(2-morpholinoethoxyimino)-acetamido]-ceph-3-eme-4-carboxylic acid STEP A: Internal salt of syn isomer of 2-(2-tritylamino-4-thiazolyl)-2-(2-morpholinoethoxyimino)-acetic acid A solution of 2 g of the syn isomer of 2-(2-tritylamino-4-thiazolyl)-2-(2-iodoethoxyimino)-acetic acid solvated with dichloroethane (1.71 g of pure acid) and 7 ml of morpholine was stirred for one hour at room temperature and was then evaporated to dryness under a nitrogen current. The residue was taken up in 30 ml of ethyl acetate and the mixture was stirred for 20 minutes at room temperature. The mixture was vacuum filtered and the recovered product was rinsed with ethyl acetate and then stirred in 15 ml of dimethoxypropane for 15 minutes. The mixture was vacuum filtered and the product was rinsed with dimethoxypropane and was taken up in 15 ml of ether. The mixture was stirred for 15 minutes and was vacuum filtered and the product was rinsed with ether to obtain 2.3 g of the internal salt of syn isomer of 2-(2-tritylamino-4-thiazolyl)-2-(2-morpholinoethoxyimino)-acetic acid melting at 180° C. (decomposition) which was used as is for the next step. For analysis, 100 mg of the product was crystallized from 0.5 ml of ethanol to obtain 46 g of the said product melting at 182°–184° C. (decomposition).

RMN Spectrum (deuterochloroform): peaks at 7.33 ppm (trityl); at 6.75 ppm (5-proton of thiazole syn).

U.V. Spectrum (0.1 N HCl in ethanol): max. at 276 nm; at $E_1^1 = 172$

I.R. Spectrum (chloroform): absorption at 1606-1529 and 1495 cm$^{-1}$ (COO$^-$ and aromatics); at 3399 cm$^{-1}$ (—NH).

STEP B: syn isomer of benzhydryl 3-acetoxymethyl-7-[2-(2-tritylamino-4-thiazolyl)-2-(2-morpholinoethoxyimino)-acetamido]-ceph-3-eme-4-carboxylic hydroiodide A solution of 1 g of the product of Step A, 0.38 g of pyridine hydroiodide, 0.63 g of dicyclohexylcarbodiimide, 0.60 g of benzhydryl 3-acetoxymethyl-7-aminoceph-3-eme-4-carboxylate and 5 ml of anhydrous dimethylformamide was stirred at room temperature for 30 minutes and was vacuum filtered to remove dicyclohexylurea. 100 ml of ether were added to the filtrate and the mixture was stirred for 10 minutes and was vacuum filtered. The product was rinsed with ether and was chromatographed over silica gel. Elution with a 7-1 ethyl acetate-ethanol mixture yielded 0.524 g of the syn isomer of benzhydryl 3-acetoxymethyl-7-[2-2tritylamino-4-thiazolyl)-2-(2-morpholinoethoxyimino)-acetamido]-ceph-3-eme-4-carboxylate hydroiodide melting at 167° C. (decomposition).

RMN Spectrum (deuterochloroform): peaks at 2.03 ppm (OAc); at 3.72 ppm ((C$\underline{H}_2$O); at 6.75 ppm (5-proton of thiazole).

U.V. Spectrum (0.1 N HCl in ethanol): max. at 268 nm; $E_1^1 = 165$; $\epsilon = 15{,}900$ I.R. Spectrum (chloroform): absorption at 1791 cm$^{-1}$ (β-lactam); at 1740 cm$^{-1}$ (ester+OAc); at 1678 cm$^{-1}$ (amide).

STEP C: Internal salt of syn isomer of 3-acetoxymethyl-7-[2-(2-amino-4-thiazolyl)-2-(2-morpholinoethoxyimino)-acetamido]-ceph-3-eme-4-carboxylic acid A mixture of 0.42 g of the product of Step B and 3 ml of trifluoroacetic acid was stirred at room temperature for 10 minutes and was then vacuum filtered. The filter was rinsed with trifluoroacetic acid and 30 ml of ether were added to the filtrate. The mixture was stirred for 15 minutes at room temperature and was vacuum filtered. The recovered product was rinsed with ether and was dissolved in 0.5 ml of methanol. 5 ml of ether were added to the solution and the mixture was stirred for 5 minutes and was vacuum filtered to obtain 208 mg of the internal salt of syn isomer of 3-acetoxymethyl-7-/2-(2-amino-4-thiazolyl)-2(2-morpholinoethoxyimino)-acetamido/ceph-3-eme-4-carboxylic acid melting at 212°–214° C. (decomposition) salified essentially with trifluoroacetic acid.

RMN Spectrum (DMSO): peaks at 2.05 ppm (OAc); at 3.17 to 4.66 ppm (C$\underline{H}_2$N— and C$\underline{H}_2$O); at 6.85 ppm (5-proton of thiazole).

U.V. Spectrum (0.1 N HCl in ethanol): max. at 260 nm; $E_1^1=253$

I.R. Spectrum (chloroform): absorption at 1797 cm$^{-1}$ (β-lactam); at 1634 cm$^{-1}$ (COO$^-$); at 1667 cm$^{-1}$ (amide).

EXAMPLE 47

Internal salt of trifluoroacetate of syn isomer of 3-acetoxymethyl-7-[2-(2-amino-4-thiazolyl)-2-(2-(4-methyl-piperazin-1-yl-ethoxyimino)-acetamido/-ceph-3-eme-4-carboxylic acid.

STEP A: Internal salt of syn isomer of 2-(2-tritylamino-4-thiazolyl)-2-(2-(4-methyl-piperazin-1-yl-ethoxyimino)-acetic acid.

A mixture of 2.22 g of N-methyl-piperazine, 15 ml of dioxane and 3.325 g of syn isomer of 2-(2-tritylamino-4-thiazolyl)-2-(2-iodoethoxyimino)-acetic acid solvated with dichloroethane (=2.84 g of pure product) was vigorously stirred at room temperature for 16 hours and was vacuum filtered to remove N-methyl-piperazine hydroiodide. The filtrate was evaporated under reduced pressure to a volume of 5 ml and 200 ml of isopropyl ether were added thereto. The mixture was stirred for 30 minutes and was vacuum filtered and the product was added to 10 ml of dimethyloxypropane. The mixture was stirred for 20 minutes and was vacuum filtered and the product was added to 24 ml of water. The mixture was stirred for 10 minutes and was vacuum filtered and the product was added to 100 ml of a 1-1 ether-isopropyl ether mixture. The mixture was stirred for 2 hours and was vacuum filtered and the product was crystallized from anhydrous ethanol to obtain 1.47 g of the internal salt of syn isomer of 2-(2-tritylamino-4-thiazolyl)-2-(2-(4-methyl-piperazin-1-yl-ethoxyimino)-acetic acid melting at 220° C. (decomposition).

RMN Spectrum (deuterochloroform): peaks at 2.52 ppm (—NCH$_3$); at 3.0 ppm (C$\underline{H}_2$N—); at 6.7 ppm (5-proton of thiazole).

U.V. Spectrum (0.1 N HCl in ethanol): max. at 277 nm; $E_1^1=257$; $\epsilon=14,300$ I.R. Spectrum (Nujol): absorption at 1602 cm$^{-1}$ (COO$^-$); at 1529 cm$^{-1}$ (heterocycle) and absence of COOH

STEP B: syn isomer of benzhydryl 3-acetoxymethyl-7-[2-(2-trityl amino-4-thiazolyl)-2-(2-(4-methyl-piperazin-1-yl)ethoxy-imino)-acetamido]-ceph-3-eme-4-carboxylate.

A mixture of 560 mg of the product of Step A, 140 mg of triethylamine hydrochloride, 5 ml of chloroform and 5 ml of methanol was heated at 60° C. for 10 minutes and was then evaporated to dryness under reduced pressure. The residue was added to 20 ml of metthylene chloride and after cooling the mixture to $-20°$ C., 1 ml of a 12.5% of pivaloyl chloride in methylene chloride was added thereto over 10 minutes. The mixture was stirred at room temperature for one hour and was cooled to $-10°$ C. after which 350 mg of benzhydryl 3-acetoxymethyl-7-amino-ceph-3-eme-4-carboxylate were added thereto all at once. The mixture was stirred for 3 hours and was then evaporated to dryness under reduced pressure at not more than 30° C. The residue was added to 50 ml of an 8-2 benzene-ethyl acetate mixture and the mixture was vacuum filtered. The filtrate was evaporated to dryness under reduced pressure and the residue was added to 25 ml of dichloroethane. 1.5 g of active magnesium silicate were added thereto and the mixture was stirred for 30 minutes and was vacuum filtered. The filter was rinsed with dichloroethane and the filtrate was evaporated to dryness under reduced pressure at a maximum of 30° C. to obtain 870 mg of the syn isomer of benzhydryl 3-acetoxymethyl-7-[2-(2-tritylamino-4-thiazolyl)-2-(2-{4-methyl-piperazin-1-yl}-ethoxyimino)-acetamido/-ceph-3-eme-4-carboxylate in the form of a white resin.

RMN Spectrum (deuterochloroform): peaks at 2.02–2.03 ppm (OAc); at 6.87 ppm (5-proton of thiazole); at 2.45 ppm (N—CH$_3$).

U.V. Spectrum (0.1 N HCl in ethanol): max. at 267–268 nm; $\epsilon=14,700$

STEP C: Internal salt of trifluoroacetate of syn isomer of 3-acetoxymethyl-7-[2-(2-amino-4-thiazolyl)-2-(2-{4-methylpiperazin-1-yl}-ethoxyimino)-acetamido]-ceph-3-eme-4-carboxylic acid A solution of 524 mg of the product of Step B and 3 ml of pure trifluoroacetic acid was stirred at room temperature for one minute and was poured into 30 ml of isopropyl ether. The mixture was stirred for 5 minutes and was vacuum filtered to obtain 320 mg of a hygroscopic product. The latter was dissolved in 1 ml of methanol and 10 ml of ether were added thereto. The mixture was stirred for 5 minutes and was vacuum filtered and the product was rinsed with ether and empasted with first chloroform and then with ether to obtain 220 mg of the internal salt of trifluoroacetate of syn isomer of 3-acetoxymethyl-7-[2-(2-amino-4-thiazolyl)-2-(2-{4-methyl-piperazin-1-yl}-ethoxyimino)-acetamido]-ceph-3-eme-4-carboxylic acid melting at 245° C.

RMN Spectrum (DMSO): peaks at 2.03 ppm (OAc); at 2.75 to 3.67 ppm (C$\underline{H}_2$N); at 6.78 ppm (5-proton of thiazole).

U.V. Spectrum (0.1 N HCl in ethanol): max. at 262 nm; $\epsilon=14,200$

I.R. Spectrum (Nujol): absorption at 1773 cm$^{-1}$ (β-lactam); at 1726 cm$^{-1}$ (OAc); at 1627 cm$^{-1}$ (COO$^-$); at 1035 cm$^{-1}$ (C=NO—).

EXAMPLE 48

Bis trifluoroacetate of syn isomer of 3-acetoxymethyl-7-[2-(2-amino-4-thiazolyl)-2-(2-aminoethoxyimino)-acetamido]-ceph-3-eme-4-carboxylic acid

STEP A: syn isomer of 2-(2-tritylamino-4-thiazolyl)-2-(2-tritylaminoethoxyimino)-acetic acid A mixture of 75 g of tritylamine, 50 g of syn isomer of ethyl 2-(2-tritylamino-4-thiazolyl)-2-(2-bromoethoxyimino)-acetate and 100 ml of dimethylsulfoxide was stirred under argon at 60° C. for 82 hours and after the temperature returned to room temperature, 10 volumes of water were added thereto. The mixture was vacuum filtered and the recovered product was washed with water and dissolved in a liter of chloroform. The solution was washed with water, with an aqueous saturated sodium chloride solution, dried and evaporated to dryness under reduced pressure at less than 40° C. The residue was added to a mixture of 320 ml of dioxane, 2 liters of absolute ethanol and 200 ml of sodium hydroxide solution and the mixture was stirred at room temperature for 24 hours and was evaporated to dryness under reduced pressure at not more than 40° C. The residue was empasted 5 times with 60 ml of a 1–7 dioxane-ethanol mixture and was then added to a liter of water and a liter of chloroform. The pH of the mixture was adjusted to 2 by stirring with sufficient N hydrochloric acid and the decanted organic phase was washed with water and with aqueous saturated sodium chloride solution, was dried and evaporated to dryness under reduced pressure at less than 40° C. The residue was suspended in 300 ml of dichloroethane and the mixture was heated at 50° C. for 15 minutes and was then vacuum filtered at room temperature. The product was successively rinsed with dichloroethane, isopropyl ether and ether and dried to a constant weight to obtain 40 g of the syn isomer of 2-(2-tritylamino-4-thiazolyl)-2-(2-tritylaminoethoxyimino)acetic acid in the form of a powder melting at 176° C.

RMN Spectrum (deuterochloroform): peaks at 6.68 ppm (5-proton of thiazole); at 2.95 ppm ($C\underline{H}_2$—N).

STEP B: syn isomer of hydroxy-benzotriazole 2-(2-tritylamino-4-thiazolyl)-2-(2-tritylaminoethoxyimino)-acetate A solution of 2.44 g of dicyclohexylcarbodiimide in 35 ml of methylene chloride was added dropwise with stirring to a mixture of 6.97 g of the product of Step A, 1.54 g of hydroxy-benzotriazole and 35 ml of methylene chloride cooled in an ice bath and after the temperature returned to room temperature, the mixture was stirred for 3½ hours and was vacuum filtered. The filter was rinsed with methylene chloride and the filtrate was washed with sodium bicarbonate solution, with water and then with aqueous saturated sodium chloride solution, dried and evaporated to dryness under reduced pressure. The residue was added to 50 ml of isopropyl ether and the mixture was vigorously stirred for one hour at room temperature and was vacuum filtered. The recovered product was rinsed with isopropyl ether and was dried to constant weight to obtain 8.046 g of the syn isomer of hydroxy-benzotriazole 2-(2-tritylamino-4-thiazolyl)-2-(2-tritylaminoethoxyimino)-acetate melting at 150°-152° C. (decomposition).

RMN Spectrum (deuterochloroform): peaks at 6.68 ppm (5-proton of thiazole); at 2.36 ppm (—$C\underline{H}_2$—N).

STEP C: syn isomer of diphenylmethyl 3-acetoxymethyl-7-[2-(2-tritylamino-4-thiazolyl)-2-(2-tritylaminoethoxyimino)acetamido]-ceph-3-eme-4-carboxylate A mixture of 11.55 g of the product of Step B, 7.65 g of diphenylmethyl 7-amino-cephalosporanate and 75 ml of methylene chloride was stirred for 18 hours at room temperature and was evaporated to dryness under reduced pressure. The residue was chromatographed over silica gel and was eluted with an 85-15 benzene-ethyl acetate mixture to obtain 9.1 g of the syn isomer of diphenylmethyl 3-acetoxymethyl-7-[2-(2-tritylamino-4-thiazolyl)-2-(2-tritylaminoethoxyimino)-acetamido]-ceph-3-eme-4-carboxylate.

STEP D: Bistrifluoroacetate of syn isomer of 3-acetoxymethyl-7-[2-(2-amino-4-thiazolyl)-2-(2-aminoethoxyimino)-acetamido]-ceph-3-eme-4-carboxylic acid A mixture of 186 mg of the product of Step C and 1.8 ml of pure trifluoroacetic acid was stirred for 3 minutes at room temperature and was then placed in an ice bath under an inert atmosphere. 18 ml of isopropyl ether were rapidly added thereto and the mixture was stirred for 10 minutes and was vacuum filtered. The recovered product was rinsed with isopropyl ether and then with ether and dried to obtain 100 mg of the bistrifluoroacetate of syn isomer of 3-acetoxymethyl-7-[2-(2-amino-4-thiazolyl)-2-(2-aminoethoxyimino)-acetamido]-ceph-3-eme-4-carboxylic acid in the form of a white powder melting at about 210° C. (decomposition).

EXAMPLE 49

Injectable solutions were prepared with 500 mg of either the syn isomer of 3-acetoxymethyl-7-[2-(2-amino-4-thiazolyl)-2-(2-aminoethoxyimino)-acetamido]-ceph-3-eme-4-carboxylic acid or the syn isomer of 3-acetoxymethyl-7-[2-(2-amino-4-thiazolyl)-2-acetoxyimino-acetamido]-ceph-3-eme-4-carboxylic acid or the syn isomer of 3-acetoxymethyl-7-[2-(2-amino-4-thiazolyl)-2-(2-imidazol-1-yl-ethoxyimino)-acetamido]-ceph-3-eme-4-carboxylic acid or the syn isomer of sodium 3-acetoxymethyl-7-[2-(2-amino-4-thiazolyl)-2-ethoxycarbonyloxyimino-acetamido]-ceph-3-eme-4-carboxylate or the syn isomer of sodium 3-acetoxymethyl-7-[2-(2-amino-4-thiazolyl)-2-(2-bromoethoxyimino)-acetamido]-ceph-3-eme-4-carboxylate or the syn isomer of 3-[(1-methyl-1,2,3,4-tetrazol-5-yl)-thiomethyl]-7-[2-(2-amino-4-thiazolyl)-2-(2-aminoethoxyimino)-acetamido]-ceph-3-eme-4-carboxylic acid or the trifluoroacetate of the syn isomer of 3-acetoxymethyl-7-[2-(2-amino-4-thiazolyl)-2-(2-iodoethoxyimino)-acetamido]-ceph-3-eme-4-carboxylic acid and sufficient sterile aqueous excipient for a final volume of 5 ml.

Gelules were prepared with 250 mg of either the syn isomer of 3-acetoxymethyl-7-[2-(2-amino-4-thiazolyl)-2-(2-aminoethoxyimino)-acetamido]-ceph-3-eme-4-carboxylic acid or the syn isomer of 3-[(1-methyl-1,2,3,4-tetrazol-5-yl)thiomethyl)-7-[2-(2-amino-4-thiazolyl)-2-(2-aminoethoxyimino)-acetamido]-ceph-3-eme-4-carboxylic acid or the syn isomer of sodium 3-acetoxymethyl-7-[2-(2-amino-4-thiazolyl)-2-(2-ethoxycarbonyloxyimino-acetamido]-ceph-3-eme-4-carboxylic acid and sufficient excipient for a final gelule weight of 400 mg.

PHARMACOLOGICAL DATA

A. In Vitro Activity

The method used was a dilution of a liquid medium where a series of tubes received the same quantity of a sterile nutrititve media and increasing doses of the test compounds were placed therein. Then each tube was seeded with a bacterial strain and was incubated for 24 or 48 hours at 37° C. in an oven. The increasing inhibition was determined by transillumination to determine the minimum inhibiting concentration (MIC in μg/ml) and the results are reported in the following Tables.

PRODUCT OF EXAMPLE 1

| STRAINS | M.I.C. in μg/ml 24 H | 48 H |
|---|---|---|
| Staphylococcus aureus ATCC 6 538 Penicillin Sensitive | 0,5 | 1 |
| Staphylococcus aureus UC 1 128 Pen-Resistant | 1 | 1 |
| Staphylococcus aureus exp. n°54 146 | 1 | 1 |
| Streptococcus pyogenes A 561 | 0,1 | 0,1 |
| Streptococcus faecalis 5 432 | 5 | 10 |
| Streptococcus faecalis 99 F 74 | 10 | 20 |
| Bacillus subtilis ATCC 6 633 | 1 | 2 |
| Escherichia Coli Sensitive Tetracycline ATCC 9 637 | 0,1 | 0,1 |
| Escherichia Coli Resistant Tetracyclin ATCC 11 303 | 0,1 | 0,1 |
| Escherichia Coli Exp. $TO_{26}B_6$ | 0,1 | 0,1 |
| Escherichia Coli Resistant Gentamycine, Tobramycine R 55 123 D | 0,5 | 0,5 |
| Klebsiella pneumoniae Exp. 52 145 | 0,05 | 0,1 |
| Klebsiella pneumoniae 2 536 Resistant Gentamycine | 0,5 | 2 |
| Proteus mirabilis (indol−) A 235 | 0,1 | 0,1 |
| Salmonella typhimurium 420 | 0,2 | 0,2 |
| Enterobacter cloacae 681 | 20 | 20 |
| Providencia Du 48 | 5 | 10 |
| Serratia Resistant Gentamycine 2 532 | 10 | 20 |

PRODUCT OF EXAMPLE 2

| STRAINS | M.I.C. in μg/ml 24 H | 48 H |
|---|---|---|
| Staphylococcus aureus ATCC 6 538 Penicillin Sensitive | 0,5 | 0,5 |
| Staphylococcus aureus UC 1 128 Pen-Resistant | 1 | 1 |
| Staphylococcus aureus exp. n°54 146 | 0,5 | 1 |
| Streptococcus pyogenes A 561 | 0,05 | 0,05 |
| Streptococcus faecalis 5 432 | 5 | 5 |
| Streptococcus faecalis 99 F 74 | 10 | 20 |
| Bacillus subtilis ATCC 6 633 | 1 | 1 |
| Escherichia Coli Sensitive Tetracycline ATCC 9 637 | 0,2 | 0,2 |
| Escherichia Coli Resistant Tetracycline ATCC 11 303 | 0,1 | 0,1 |
| Escherichia Coli Exp. $TO_{26}B_6$ | 0,05 | 0,05 |
| Escherichia Coli Resistant Gentamycine, Tobramycine R 55 123 D | 0,5 | 0,5 |
| Klebsiella pneumoniae Exp. 52 145 | 0,05 | 0,05 |
| Klebsiella pneumoniae 2 536 Resistant Gentamycine | 0,5 | 0,5 |
| Proteus mirabilis (indol−) A 235 | 0,1 | 0,1 |
| Salmonella typhimurium 420 | 0,1 | 0,2 |
| Enterobacter cloacae 681 | 20 | 20 |
| Providencia Du 48 | 2 | 5 |

PRODUCT OF EXAMPLE 3

| STRAINS | M.I.C. in μg/ml 24 H | 48 H |
|---|---|---|
| Staphylococcus aureus ATCC 6 538 Penicillin Sensitive | 1 | 2 |
| Staphylococcus aureus UC 1 128 Pen-Resistant | 2 | 2 |
| Staphylococcus aureus exp. N°54 146 | 2 | 2 |
| Streptococcus pyogenes A 561 | 0,2 | 0,2 |
| Bacillus subtilis ATCC 6 633 | 2 | 3 |
| Escherichia Coli Sensitive Tetracyclin ATCC 9 637 | 0,5 | 0,5 |
| Escherichia Coli Resistant Tetracyclin ATCC 11 303 | 0,2 | 0,2 |
| Escherichia Coli Exp. $TO_{26}B_6$ | 0,1 | 0,1 |
| Escherichia Coli Resistant Gentamycine, Tobramycine R 55 123 D | 0,5 | 1 |
| Klebsiella pneumoniae Exp. 52 145 | 0,1 | 0,2 |
| Klebsiella pneumoniae 2 536 Resistant Gentamycine | 1 | 1 |
| Proteus mirabilis (indol−) A 235 | 0,2 | 0,2 |
| Salmonella typhimurium 420 | 0,5 | 0,5 |
| Enterobacter cloacae 681 | 20 | 40 |
| Providencia Du 48 | 3 | 5 |
| Serratia Resistant Gentamycine 2 532 | 3 | 5 |

PRODUCT OF EXAMPLE 5

| STRAINS | M.I.C. in μg/ml 24 H | 48 H |
|---|---|---|
| Staphylococcus aureus ATCC 6 538 Penicillin Sensitive | 2 | 3 |
| Staphylococcus aureus UC 1 128 Pen-Resistant | 5 | 5 |
| Staphylococcus aureus exp. N°54 146 | 2 | 3 |
| Streptococcus pyogenes A 561 | 0,5 | 0,5 |
| Bacillus subtilis ATCC 6 633 | 10 | 10 |
| Escherichia Coli Sens. Tetracycline ATCC 9 637 | 0,5 | 0,5 |
| Escherichia Coli Resistant Tetracycline ATCC 11 303 | 0,1 | 0,1 |
| Escherichia Coli Exp. $TO_{26}B_6$ | 0,5 | 0,5 |
| Escherichia Coli Resistant Gentamycine, Tobramycine R 55 123 D | 2 | 2 |
| Klebsiella pneumoniae Exp. 52 145 | 0,2 | 0,2 |
| Klebsiella pneumoniae 2 536 Resistant Gentamycine | 2 | 2 |
| Proteus mirabilis (indol−) A 235 | 0,2 | 0,2 |
| Salmonella typhimurium 420 | 0,5 | 0,5 |

PRODUCT OF EXAMPLE 7

| STRAINS | M.I.C. in μg/ml 24 H | 48 H |
|---|---|---|
| Staphylococcus aureus ATCC 6 538 Penicillin Sensitive | 5 | 20 |
| Staphylococcus aureus UC 1 128 Pen-Resistant | 10 | 10 |
| Staphylococcus aureus exp. n°54 146 | 10 | 10 |
| Streptococcus pyogenes A 561 | 0,5 | 1 |
| Bacillus subtilis ATCC 6 633 | 5 | 20 |
| Escherichia Coli Sensitive Tetracycline ATCC 9 637 | 1 | 1 |
| Escherichia Coli Resistant Tetracycline ATCC 11 303 | 0,5 | 1 |
| Escherichia Coli Exp. $TO_{26}B_6$ | 1 | 1 |
| Escherichia Coli Resistant Gentamycine, Tobramycine R 55 123 D | 1 | 1 |
| Klebsiella pneumoniae Exp. 52 145 | 0,5 | 1 |
| Klebsiella pneumoniae 2 536 Resistant Gentamycine | 2 | 2 |
| Proteus mirabilis (indol−) A 235 | 0,1 | 0,1 |
| Proteus vulgaris (indol+) A 232 | 1 | 2 |
| Salmonella typhimurium 420 | 1 | 1 |
| Providencia Du 48 | 20 | 20 |
| Serratia Resistant Gentamycine 2 532 | 10 | 10 |

PRODUCT OF EXAMPLE 9

| STRAINS | M.I.C. in μg/ml | |
|---|---|---|
| | 24 H | 48 H |
| *Staphylococcus aureus* ATCC 6 538 Penicillin Sensitive | 2 | 2 |
| *Staphylococcus aureus* UC 1 128 Pen-Resistant | 3 | 3 |
| *Staphylococcus aureus* exp. n°54 146 | 3 | 3 |
| *Streptococcus pyogenes* A 561 | 0,2 | 0,2 |
| *Bacillus subtilis* ATCC 6 633 | 1 | 2 |
| *Escherichia Coli* Sensitive Tetracycline ATCC 9 637 | 0,5 | 0,5 |
| *Escherichia Coli* Resistant Tetracycline ATCC 11 303 | 0,1 | 0,1 |
| *Escherichia Coli* Exp. TO$_{26}$B$_6$ | 1 | 1 |
| *Escherichia Coli* Resistant Gentamycine, Tobramycine R 55 123 D | 0,5 | 0,5 |
| *Klebsiella pneumoniae* Exp. 52 145 | 0,1 | 0,1 |
| *Klebsiella pneumoniae* 2 536 Resistant Gentamycine | 1 | 1 |
| *Proteus mirabilis* (indol−) A 235 | 0,1 | 0,1 |
| *Proteus vulgaris* (indol+) A 232 | 1 | 1 |
| *Salmonella typhimurium* 420 | 0,5 | 1 |
| *Enterobacter cloacae* 681 | 20 | >40 |
| *Providencia* Du 48 | 3 | 3 |
| *Serratia* Resistant Gentamycine 2 532 | 3 | 5 |

PRODUCT OF EXAMPLE 10

| STRAINS | M.I.C. in μg/ml | |
|---|---|---|
| | 24 H | 48 H |
| *Staphylococcus aureus* ATCC 6 538 Penicillin Sensitive | 10 | 20 |
| *Staphylococcus aureus* UC 1 128 Pen-resistant | 20 | 20 |
| *Staphylococcus aureus* exp. n°54 146 | 10 | 20 |
| *Streptococcus pyogenes* A 561 | 1 | 3 |
| *Bacillus subtilis* ATCC 6 633 | 10 | 20 |
| *Escherichia Coli* Sensitive Tetracycline ATCC 9 637 | 0,5 | 0,5 |
| *Escherichia Coli* Resistant Tetracycline ATCC 11 303 | 0,5 | 0,5 |
| *Escherichia Coli* Exp. TO$_{26}$B$_6$ | 0,5 | 0,5 |
| *Escherichia Coli* Resistant Gentamycine, Tobramycine R 55 123 D | 1 | 1 |
| *Klebsiella pneumoniae* Exp. 52 145 | 0,05 | 0,5 |
| *Klebsiella pneumoniae* 2 536 Resistant Gentamycine | 1 | 1 |
| *Proteus mirabilis* (indol−) A 235 | 0,1 | 0,1 |
| *Proteus vulgaris* (indol+) A 232 | 0,2 | 0,2 |
| *Salmonella typhimurium* 420 | 0,5 | 1 |
| *Enterobacter cloacae* 681 | 20 | 40 |
| *Providencia* Du 48 | 2 | 3 |
| *Serratia* Resistant Gentamycine 2 532 | 10 | 10 |

PRODUCT OF EXAMPLE 12

| STRAINS | M.I.C. in μg/ml | |
|---|---|---|
| | 24 H | 48 H |
| *Staphylococcus aureus* ATCC 6 538 Penicillin Sensitive | 10 | 20 |
| *Staphylococcus aureus* UC 1 128 Pen-Resistant | 10 | 10 |
| *Staphylococcus aureus* exp. n°54 146 | 10 | 10 |
| *Streptococcus pyogenes* A 561 | 0,1 | 0,1 |
| *Streptococcus faecalis* 5 432 | 20 | >40 |
| *Bacillus subtilis* ATCC 6 633 | 10 | 10 |
| *Escherichia Coli* Sensitive Tetracycline ATCC 9 637 | 0,2 | 0,2 |
| *Escherichia Coli* Resistant Tetracycline ATCC 11 303 | 0,05 | 0,05 |
| *Escherichia Coli* Exp. TO$_{26}$B$_6$ | 0,2 | 0,2 |
| *Escherichia Coli* Resistant Gentamycine, Tobramycine R 55 123 D | 0,5 | 0,5 |
| *Klebsiella pneumoniae* Exp. 52 145 | 0,1 | 0,1 |
| *Klebsiella pneumoniae* 2 536 Resistant Gentamycine | 0,2 | 0,2 |
| *Proteus mirabilis* (indol−) A 235 | 0,02 | 0,02 |
| *Proteus vulgaris* (indol+) A 232 | 1 | 1 |
| *Salmonella typhimurium* 420 | 0,5 | 0,5 |
| *Enterobacter cloacae* 681 | 40 | 40 |
| *Providencia* Du 48 | 10 | — |
| *Serratia* Resistant Gentamycine 2 532 | 2 | — |

PRODUCT OF EXAMPLE 13

| STRAINS | M.I.C. in μg/ml | |
|---|---|---|
| | 24 H | 48 H |
| *Staphylococcus aureus* ATCC 6 538 Penicillin Sensitive | 1 | 1 |
| *Staphylococcus aureus* UC 1 128 Pen-Resistant | 1 | 1 |
| *Staphylococcus aureus* exp. n° 54 146 | 1 | 2 |
| *Streptococcus pyogenes* A 561 | 0,05 | 0,05 |
| *Streptococcus faecalis* 5 432 | 5 | 5 |
| *Streptococcus faecalis* 99 F 74 | 10 | >40 |
| *Bacillus subtilis* ATCC 6 633 | 1 | 1 |
| *Escherichia Coli* Sensitive Tetracycline ATCC 9 637 | 0,5 | 0,5 |
| *Escherichia Coli* Resistant Tetracycline ATCC 11 303 | 0,15 | 0,2 |
| *Escherichia Coli* Exp. TO$_{26}$B$_6$ | 0,5 | 0,5 |
| *Escherichia Coli* Resistant Gentamycine, Tobramycine R 55 123 D | 0,5 | 0,5 |
| *Klebsiella pneumoniae* Exp. 52 145 | 0,2 | 0,2 |
| *Klebsiella pneumoniae* 2 536 Resistant Gentamycine | 1 | 1 |
| *Proteus mirabilis* (indol−) A 235 | 0,5 | 0,5 |
| *Salmonella typhimurium* 420 | 0,5 | 0,5 |
| *Enterobacter cloacae* 681 | 20 | 20 |
| *Providencia* Du 48 | 2 | 2 |
| *Serratia* Resistant Gentamycine 2 532 | 5 | 5 |

PRODUCT OF EXAMPLE 14

| STRAINS | M.I.C. in μg/ml | |
|---|---|---|
| | 24 H | 48 H |
| *Staphylococcus aureus* ATCC 6 538 Penicillin Sensitive | 10 | 10 |
| *Staphylococcus aureus* UC 1 128 Pen-Resistant | 10 | 10 |
| *Staphylococcus aureus* exp. n° 54 146 | 10 | 10 |
| *Streptococcus pyogenes* A 561 | ≦ 0,02 | ≦ 0,02 |
| *Streptococcus faecalis* 5 432 | 10 | >40 |
| *Streptococcus faecalis* 99 F 74 | 1 | 2 |
| *Bacillus subtilis* ATCC 6 633 | 0,2 | 0,2 |
| *Escherichia Coli* Sensitive Tetracycline ATCC 9 637 | 0,2 | 0,2 |
| *Escherichia Coli* Resistant Tetracycline ATCC 11 303 | 0,05 | 0,05 |
| *Escherichia Coli* Exp. TO$_{26}$B$_6$ | 0,1 | 0,1 |
| *Escherichia Coli* Resistant Gentamycine, Tobramycine R 55 123 D | 0,1 | 0,1 |
| *Klebsiella pneumoniae* Exp. 52 145 | 0,1 | 0,1 |
| *Klebsiella pneumoniae* 2 536 Resistant Gentamycine | 0,5 | 0,5 |
| *Proteus mirabilis* (indol−) A 235 | 0,1 | 0,2 |
| *Proteus vulgaris* (indol+) A 232 | 1 | 3 |
| *Salmonella typhimurium* 420 | 0,1 | 0,1 |
| *Enterobacter cloacae* 681 | 3 | 3 |
| *Providencia* Du 48 | 1 | 1 |
| *Serratia* Resistant Gentamycine 2 532 | 1 | 1 |

PRODUCT OF EXAMPLE 15

| STRAINS | M.I.C. in μg/ml | |
|---|---|---|
| | 24 H | 48 H |
| *Staphylococcus aureus* ATCC 6 538 Penicillin | 5 | 5 |

PRODUCT OF EXAMPLE 15 -continued

| STRAINS | M.I.C. in μg/ml | |
|---|---|---|
| | 24 H | 48 H |
| Sensitive | | |
| *Staphylococcus aureus* UC 1 128 Pen-Resistant | 10 | 10 |
| *Staphylococcus aureus* exp. n° 54 146 | 5 | 10 |
| *Streptococcus pyogenes* A 561 | ≦ 0,02 | ≦ 0,02 |
| *Streptococcus faecalis* 5 432 | 10 | >40 |
| *Bacillus subtilis* ATCC 6 633 | 1 | 2 |
| *Escherichia Coli* Sensitive Tetracycline ATCC 9 637 | 0,1 | 0,3 |
| *Escherichia Coli* Resistant Tetracycline ATCC 11 303 | 0,05 | 0,05 |
| *Escherichia Coli* Exp. TO$_{26}$B$_6$ | 0,1 | 0,1 |
| *Escherichia Coli* Resistant Gentamycine, Tobramycine R 55 123 D | 0,1 | 0,1 |
| *Klebsiella pneumoniae* Exp. 52 145 | 0,05 | 0,05 |
| *Klebsiella pneumoniae* 2 536 Resistant Gentamycine | 0,2 | 0,2 |
| *Proteus mirabilis* (indol−) A 235 | 0,1 | 0,2 |
| *Proteus vulgaris* (indol+) A 232 | 1 | 2 |
| *Salmonella typhimurium* 420 | 0,1 | 0,1 |
| *Enterobacter cloacae* 681 | 2 | 2 |
| *Providencia* Du 48 | 1 | 1 |
| *Serratia* Resistant Gentamycine 2 532 | 0,5 | 1 |

PRODUCT OF EXAMPLE 16

| STRAINS | M.I.C. in μg/ml | |
|---|---|---|
| | 24 H | 48 H |
| *Staphylococcus aureus* ATCC 6 538 Penicillin Sensitive | 1 | 1 |
| *Staphylococcus aureus* UC 1 128 Pen-Resistant | 1 | 2 |
| *Staphylococcus aureus* exp. n° 54 146 | 2 | 2 |
| *Streptococcus pyogenes* A 561 | 0,05 | 0,05 |
| *Streptococcus faecalis* 5 432 | 5 | 40 |
| *Streptococcus faecalis* 99 F 74 | 20 | >40 |
| *Bacillus subtilis* ATCC 6 633 | 2 | 3 |
| *Escherichia Coli* Sensitive Tetracycline ATCC 9 637 | 0,5 | 1 |
| *Escherichia Coli* Resistant Tetracycline ATCC 11 303 | 0,05 | 0,05 |
| *Escherichia Coli* Exp. TO$_{26}$B$_6$ | 0,5 | 0,5 |
| *Escherichia Coli* Resistant Gentamycine, Tobramycine R 55 123 D | 0,2 | 0,2 |
| *Klebsiella pneumoniae* Exp. 52 145 | 0,2 | 0,2 |
| *Klebsiella pneumoniae* 2 536 Resistant Gentamycine | 1 | 1 |
| *Proteus mirabilis* (indol−) A 235 | 0,1 | 0,1 |
| *Salmonella typhimurium* 420 | 0,5 | 0,5 |
| *Providencia* Du 48 | 10 | 10 |
| *Serratia* Resistant Gentamycine 2 532 | 2 | 2 |

PRODUCT OF EXAMPLE 19

| STRAINS | M.I.C. in μg/ml | |
|---|---|---|
| | 24 H | 48 H |
| *Staphylococcus aureus* ATCC 6 538 Penicillin Sensitive | 1 | 1 |
| *Staphylococcus aureus* UC 1 128 Pen-Resistant | 2 | 2 |
| *Staphylococcus aureus* exp. n° 54 146 | 2 | 2 |
| *Streptococcus pyogenes* A 561 | 0,1 | 0,1 |
| *Streptococcus faecalis* 5 432 | 10 | 40 |
| *Bacillus subtilis* ATCC 6 633 | 3 | 10 |
| *Escherichia Coli* Sensitive Tetracycline ATCC 9 637 | 0,5 | 0,5 |
| *Escherichia Coli* Resistant Tetracycline ATCC 11 303 | 0,05 | 0,05 |
| *Escherichia Coli* Exp. TO$_{26}$B$_6$ | 0,2 | 0,2 |
| *Escherichia Coli* Resistant Gentamycine, Tobramycine R 55 123 D | 0,5 | 0,5 |
| *Klebsiella pneumoniae* Exp. 52 145 | 0,05 | 0,05 |
| *Klebsiella pneumoniae* 2 536 Resistant Gentamycine | 0,5 | 1 |
| *Proteus mirabilis* (indol−) A 235 | 0,1 | 0,1 |

PRODUCT OF EXAMPLE 19 -continued

| STRAINS | M.I.C. in μg/ml | |
|---|---|---|
| | 24 H | 48 H |
| *Salmonella typhimurium* 420 | 0,1 | 0,1 |
| *Enterobacter cloacae* 681 | 10 | 20 |
| *Providencia* Du 48 | 3 | 5 |
| *Serratia* Resistant Gentamycine 2 532 | 5 | 10 |

PRODUCT OF EXAMPLE 22

| STRAINS | M.I.C. in μg/ml | |
|---|---|---|
| | 24 H | 48 H |
| *Staphylococcus aureus* ATCC 6 538 Penicillin Sensitive | 0,5 | 1 |
| *Staphylococcus aureus* UC 1 128 Pen-Resist. | 1 | 1 |
| *Staphylococcus aureus* exp. N° 54 146 | 1 | 1 |
| *Streptococcus pyogenes* A 561 | ≦ 0,02 | ≦ 0,02 |
| *Streptococcus faecalis* 5 432 | 2 | 10 |
| *Streptococcus faecalis* 99 F 74 | 10 | >40 |
| *Bacillus subtilis* ATCC 6 633 | 0,2 | 1 |
| *Escherichia Coli* Sensitive Tetracycline ATCC 9 637 | 1 | 1 |
| *Escherichia Coli* Resistant Tetracycline ATCC 11 303 | 0,2 | 0,2 |
| *Escherichia Coli* Exp. TO$_{26}$B$_6$ | 0,5 | 0,5 |
| *Escherichia Coli* Resistant Gentamycine, Tobramycine R 55 123 D | 0,5 | 0,5 |
| *Klebsiella pneumoniae* Exp. 52 145 | 0,2 | 0,5 |
| *Klebsiella pneumoniae* 2 536 Resistant Gentamycine | 2 | 2 |
| *Proteus mirabilis* (indol−) A 235 | 0,2 | 0,2 |
| *Salmonella typhimurium* 420 | 1 | 2 |
| *Enterobacter cloacae* 681 | 5 | 10 |
| *Providencia* Du 48 | 5 | 5 |
| *Serratia* Resistant Gentamycine 2 532 | 5 | 5 |

PRODUCT OF EXAMPLE 24

| STRAINS | M.I.C. in μg/ml | |
|---|---|---|
| | 24 H | 48 H |
| *Staphylococcus aureus* ATCC 6 538 Penicillin Sensitive | 1 | 1 |
| *Staphylococcus aureus* UC 1 128 Pen-Resist. | 1 | 1 |
| *Staphylococcus aureus* exp. N° 54 146 | 1 | 1 |
| *Streptococcus pyogenes* A 561 | ≦ 0,02 | ≦ 0,02 |
| *Streptococcus faecalis* 5 432 | 2 | 20 |
| *Streptococcus faecalis* 99 F 74 | 10 | 10 |
| *Bacillus subtilis* ATCC 6 633 | 0,5 | 0,5 |
| *Escherichia Coli* Sensitive Tetracycline ATCC 9 637 | 2 | 2 |
| *Escherichia Coli* Resistant Tetracycline ATCC 11 303 | 1 | 1 |
| *Escherichia Coli* Exp. TO$_{26}$B$_6$ | 2 | 3 |
| *Escherichia Coli* Resistant Gentamycine, Tobramycine R 55 123 D | 1 | 2 |
| *Klebsiella pneumoniae* Exp. 52 145 | 1 | 1 |
| *Klebsiella pneumoniae* 2 536 Resistant Gentamycine | 10 | 10 |
| *Proteus mirabilis* (indol−) A 235 | 1 | 1 |
| *Salmonella typhimurium* 420 | 2 | 3 |
| *Providencia* Du 48 | 20 | 20 |
| *Serratia* Resistant Gentamycine 2 532 | 10 | 10 |

PRODUCT OF EXAMPLE 26

| STRAINS | M.I.C. in μg/ml | |
|---|---|---|
| | 24 H | 48 H |
| *Staphylococcus aureus* ATCC 6 538 Penicillin Sensitive | 2 | 2 |
| *Staphylococcus aureux* UC 1 128 Pen-Resist. | 2 | 2 |
| *Staphylococcus aureus* exp. n° 54 146 | 2 | 2 |

-continued

PRODUCT OF EXAMPLE 26

| STRAINS | M.I.C. in µg/ml | |
|---|---|---|
| | 24 H | 48 H |
| Streptococcus pyogenes A 561 | ≦0,02 | ≦0,02 |
| Streptococcus faecalis 5 432 | 3 | >40 |
| Streptococcus faecalis 99 F 74 | 10 | >40 |
| Bacillus subtilis ATCC 6 633 | 1 | 1 |
| Escherichia Coli Sensitive Tetracycline ATCC 9 637 | 2 | 2 |
| Escherichia Coli Resistant Tetracycline ATCC 11 303 | 1 | 2 |
| Escherichia Coli Exp. TO$_{26}$B$_6$ | 2 | 2 |
| Escherichia Coli Resistant Gentamycine, Tobramycine R 55 123 D | 1 | 2 |
| Klebsiella pneumoniae Exp. 52 145 | 1 | 1 |
| Klebsiella pneumoniae 2 536 Resistant Gentamycine | 5 | 5 |
| Proteus mirabilis (indol−) A 235 | 0,5 | 0,5 |
| Salmonella typhimurium 420 | 2 | 2 |
| Providencia Du 48 | 40 | 40 |
| Serratia Resistant Gentamycine 2 532 | 10 | 10 |

PRODUCT OF EXAMPLE 28

| STRAINS | M.I.C. in µg/ml | |
|---|---|---|
| | 24 H | 48 H |
| Staphylococcus aureus ATCC 6 538 Penicillin Sensitive | 0,5 | 1 |
| Staphylococcus aureus UC 1 128 Pen-Resist. | 1 | 1 |
| Staphylococcus aureus exp. n° 54 146 | 1 | 1 |
| Streptococcus pyogenes A 561 | ≦0,02 | ≦0,02 |
| Bacillus subtilis ATCC 6 633 | 1 | 2 |
| Escherichia Coli Sensitive Tetracycline ATCC 9 637 | 3 | 3 |
| Escherichia Coli Resistant Tetracycline ATCC 11 303 | 1 | 1 |
| Escherichia Coli Exp. TO$_{26}$B$_6$ | 2 | 2 |
| Escherichia Coli Resistant Gentamycine, Tobramycine R 55 123 D | 2 | 2 |
| Klebsiella pneumoniae Exp. 52 145 | 1 | 1 |
| Klebsiella pneumoniae 2 536 Resistant Gentamycine | 10 | 10 |
| Proteus mirabilis (indol−) A 235 | 1 | 1 |
| Salmonella typhimurium 420 | 2 | 2 |
| Enterobacter cloacae 681 | 20 | 40 |
| Providencia Du 48 | 10 | 20 |
| Serratia Resistant Gentamycine 2 532 | 5 | 5 |

PRODUCT OF EXAMPLE 30

| STRAINS | M.I.C. in µg/ml | |
|---|---|---|
| | 24 H | 48 H |
| Staphylococcus aureus ATCC 6 538 Penicillin-Sensitive | 2 | 2 |
| Staphylococcus aureus UC 1 128 Pen-Resist. | 2 | 2 |
| Staphylococcus aureus exp.n° 54 146 | 2 | 2 |
| Streptococcus pyogenes A 561 | 0,05 | 0,05 |
| Bacillus subtilis ATCC 6 633 | 1 | 1 |
| Escherichia Coli Sensitive Tetracycline ATCC 9 637 | 5 | 5 |
| Escherichia Coli Resistant Tetracycline ATCC 11 303 | 2 | 2 |
| Escherichia Coli Exp. TO$_{26}$B$_6$ | 3 | 3 |
| Escherichia Coli Resistant Gentamycine, Tobramycine R 55 123 D | 3 | 3 |
| Klebsiella pneumoniae Exp. 52 145 | 1 | 1 |
| Klebsiella pneumoniae 2 536 Resistant Gentamycine | 20 | 20 |
| Proteus mirabilis (indol−) A 235 | 2 | 2 |
| Salmonella typhimurium 420 | 3 | 5 |
| Providencia DU 48 | 20 | 20 |
| Serratia Resistant Gentamycine 2 532 | 5 | 10 |

PRODUCT OF EXAMPLE 31

| STRAINS | M.I.C. in µg/ml | |
|---|---|---|
| | 24 H | 48 H |
| Staphylococcus aureus ATCC 6 538 Penicillin-Sensitive | 2 | 2 |
| Staphylococcus aureus UC 1 128 Pen-Resist. | 2 | 2 |
| Staphylococcus aureus exp. n° 54 146 | 2 | 2 |
| Streptococcus pyogenes A 561 | ≦0,02 | ≦0,02 |
| Streptococcus faecalis 5 432 | 3 | 40 |
| Bacillus subtilis ATCC 6 633 | 2 | 3 |
| Escherichia Coli Sensitive Tetracycline ATCC 9 637 | 3 | 3 |
| Escherichia Coli Resistant Tetracycline ATCC 11 303 | 3 | 3 |
| Escherichia Coli Exp. TO$_{26}$B$_6$ | 2 | 2 |
| Escherichia Coli Resistant Gentamycine, Tobramycine R 55 123 D | 2 | 2 |
| Klebsiella pneumoniae Exp. 52 145 | 0,5 | 0,5 |
| Klebsiella pneumoniae 2 536 Resistant Gentamycine | 10 | 10 |
| Proteus mirabilis (indol−) A 235 | 1 | 1 |
| Salmonella typhimurium 420 | 2 | 2 |
| Providencia DU 48 | 20 | 20 |
| Serratia Resistant Gentamycine 2.532 | 3 | 5 |

PRODUCT OF EXAMPLE 33

| STRAINS | M.I.C. in µg/ml | |
|---|---|---|
| | 24 H | 48 H |
| Staphylococcus aureus ATCC 6 538 Penicillin-Sensitive | 2 | 2 |
| Staphylococcus aureus UC 1 128 Pen-Resist. | 2 | 2 |
| Staphylococcus aureus exp.n° 54 146 | 2 | 2 |
| Streptococcus pyogenes A 561 | 0,05 | 0,05 |
| Streptococcus faecalis 5 432 | 3 | 40 |
| Bacillus subtilis ATCC 6 633 | 2 | 2 |
| Escherichia Coli Sensitive Tetracycline ATCC 9 637 | 1 | 2 |
| Escherichia Coli Resistant Tetracycline ATCC 11 303 | 0,5 | 0,5 |
| Escherichia Coli Exp. TO$_{26}$B$_6$ | 1 | 1 |
| Escherichia Coli Resistant Gentamycine, Tobramycine R 55 123 D | 1 | 1 |
| Klebsiella pneumoniae Exp. 52 145 | 0,1 | 0,5 |
| Klebsiella pneumoniae 2 536 Resistant Gentamycine | 2 | 3 |
| Proteus mirabilis (indol−) A 235 | 0,2 | 0,2 |
| Salmonella typhimurium 420 | 1 | 1 |
| Providencia DU 48 | 5 | 5 |
| Serratia Resistant Gentamycine 2 532 | 2 | 3 |

PRODUCT OF EXAMPLE 37

| STRAINS | M.I.C. in µg/ml | |
|---|---|---|
| | 24 H | 48 H |
| Staphylococcus aureus ATCC 6 538 Penicillin-Sensitive | 1 | 1 |
| Staphylococcus aureus UC 1 128 Pen-Resist. | 1 | 1 |
| Staphylococcus aureus exp. n° 54 146 | 1 | 1 |
| Streptococcus pyogenes A 561 | 0,05 | 0,05 |
| Bacillus subtilis ATCC 6 633 | 1 | 2 |
| Escherichia Coli Sensitive Tetracycline ATCC 9 637 | 2 | 2 |
| Escherichia Coli Resistant Tetracycline ATCC 11 303 | 0,5 | 0,5 |
| Escherichia Coli Exp. TO$_{26}$B$_6$ | 1 | 1 |
| Escherichia Coli Resistant Gentamycine, Tobramycine R 55 123 D | 2 | 2 |
| Klebsiella pneumoniae Exp. 52 145 | 0,05 | 0,05 |
| Klebsiella pneumoniae 2 536 Resistant Gentamycine | 3 | 3 |
| Proteus mirabilis (indol−) A 235 | 0,5 | 0,5 |
| Salmonella typhimurium 420 | 3 | 3 |
| Enterobacter cloacae 681 | 10 | 20 |
| Providencia DU 48 | 10 | 10 |

-continued

PRODUCT OF EXAMPLE 37

| STRAINS | M.I.C. in μg/ml | |
|---|---|---|
| | 24 H | 48 H |
| Serratia Resistant Gentamycine 2 532 | 2 | 3 |

PRODUCT OF EXAMPLE 38

| STRAINS | M.I.C. in μg/ml | |
|---|---|---|
| | 24 H | 48 H |
| Staphylococcus aureus ATCC 6 538 Penicillin-Sensitive | 2 | 3 |
| Staphylococcus aureus UC 1 128 Pen-Resist. | 3 | 5 |
| Staphylococcus aureus exp. n° 54 146 | 3 | 5 |
| Streptococcus pyogenes A 561 | ≦0,02 | ≦0,02 |
| Streptococcus faecalis 5 432 | 2 | 40 |
| Streptococcus faecalis 99 F 74 | 40 | >40 |
| Bacillus subtilis ATCC 6 633 | 1 | 2 |
| Escherichia Coli Sensitive Tetracycline ATCC 9 637 | 0,5 | 0,5 |
| Escherichia Coli Resistant Tetracycline ATCC 11 303 | 0,1 | 0,1 |
| Escherichia Coli Exp. TO$_{26}$B$_6$ | 0,2 | 0,5 |
| Escherichia Coli Resistant Gentamycine, Tobramycine R 55 123 D | 0,2 | 0,2 |
| Klebsiella pneumoniae Exp. 52 145 | 0,05 | 0,05 |
| Klebsiella pneumoniae 2 536 Resistant Gentamycine | 2 | 2 |
| Proteus numbilis (indol+) A 232 | 1 | 2 |
| Proteus mirabilis (indol−) A 235 | 0,2 | 1 |
| Salmonella typhimurium 420 | 0,2 | 0,5 |
| Enterobacter cloacae 681 | 2 | 3 |
| Providencia DU 48 | 2 | 3 |
| Serratia Resistant Gentamycine 2 532 | 1 | 1 |

PRODUCT OF EXAMPLE 39

| STRAINS | M.I.C. in μg/ml | |
|---|---|---|
| | 24 H | 48 H |
| Staphylococcus aureus ATCC 6 538 Penicillin-Sensitive | 1 | 1 |
| Staphylococcus aureus UC 1 128 Pen-Resist. | 1 | 2 |
| Staphylococcus aureus exp. n° 54 146 | 1 | 1 |
| Streptococcus pyogenes A 561 | ≦0,02 | ≦0,02 |
| Streptococcus faecalis 5 432 | 2 | 10 |
| Bacillus subtilis ATCC 6 633 | 1 | 5 |
| Escherichia Coli Sensitive Tetracycline ATCC 9 637 | 3 | 5 |
| Escherichia Coli Resistant Tetracycline ATCC 11 303 | 0,5 | 0,5 |
| Escherichia Coli Exp. TO$_{26}$B$_6$ | 2 | 2 |
| Escherichia Coli Resistant Gentamycine, Tobramycine R 55 123 D | 2 | 2 |
| Klebsiella pneumoniae Exp. 52 145 | 0,2 | 0,2 |
| Klebsiella pneumoniae 2 536 Resistant Gentamycine | 5 | 5 |
| Proteus mirabilis (indol−) A 235 | 0,5 | 0,5 |
| Salmonella typhimurium 420 | 1 | 1 |
| Providencia DU 48 | 10 | 10 |
| Serratia Resistant Gentamycine 2 532 | 10 | 10 |

PRODUCT OF EXAMPLE 40

| STRAINS | M.I.C. in μg/ml | |
|---|---|---|
| | 24 H | 48 H |
| Streptococcus pyogenes A 561 | 0,05 | 0,1 |
| Escherichia Coli Sensitive Tetracycline ATCC 9 637 | 2 | 3 |
| Escherichia Coli Resistant Tetracycline ATCC 11 303 | 1 | 1 |
| Escherichia Coli Exp. TO$_{26}$B$_6$ | 2 | 2 |
| Escherichia Coli Resistant Gentamycine, Tobramycine R 55 123 D | 3 | 3 |
| Klebsiella pneumoniae Exp. 52 145 | 1 | 1 |
| Klebsiella pneumoniae 2 536 Resistant Gentamycine | 5 | 10 |
| Proteus mirabilis (indol−) A 235 | 1 | 1 |
| Salmonella typhimurium 420 | 3 | 5 |
| Providencia Du 48 | 5 | 5 |
| Serratia Resistant Gentamycine 2 532 | 20 | 20 |

PRODUCT OF EXAMPLE 41

| STRAINS | M.I.C. in μg/ml | |
|---|---|---|
| | 24 H | 48 H |
| Staphylococcus aureus ATCC 6 538 Penicillin-Sensitive | 10 | 10 |
| Staphylococcus aureus UC 1 128 Pen-Resist. | 5 | 10 |
| Staphylococcus aureus exp. n° 54 146 | 10 | 10 |
| Streptococcus pyogenes A 561 | 0,02 | 0,02 |
| Bacillus subtilis ATCC 6 633 | 2 | 2 |
| Escherichia Coli Sensitive Tetracycline ATCC 9 637 | 1 | 1 |
| Escherichia Coli Resistant Tetracycline ATCC 11 303 | 0,05 | 0,1 |
| Escherichia Coli Exp. TO$_{26}$B$_6$ | 0,5 | 0,5 |
| Escherichia Coli Resistant Gentamycine, Tobramycine R 55 123 D | 0,5 | 0,5 |
| Klebsiella pneumoniae Exp. 52 145 | 0,2 | 0,2 |
| Klebsiella pneumoniae 2 536 Resistant Gentamycine | 2 | 2 |
| Proteus mirabilis (indol−) A 235 | 0,2 | 0,2 |
| Proteus mirabilis (indol+) A 232 | 5 | 5 |
| Salmonella typhimurium 420 | 0,5 | 1 |
| Enterobacter cloacae 681 | 20 | 20 |
| Providencia DU 48 | 3 | 3 |
| Serratia Resistant Gentamycine 2 532 | 1 | 2 |

PRODUCT OF EXAMPLE 42

| STRAINS | M.I.C. in μg/ml | |
|---|---|---|
| | 24 H | 48 H |
| Staphylococcus aureus ATCC 6 538 Penicillin Sensitive | 5 | 5 |
| Staphylococcus aureus UC 1 128 Pen-Resistant | 10 | 10 |
| Staphylococcus aureus exp.n° 54 146 | 5 | 5 |
| Streptococcus pyogenes A 561 | ≦0,02 | ≦0,02 |
| Streptococcus faecalis 5 432 | 20 | >40 |
| Bacillus subtilis ATCC 6 633 | 1 | 2 |
| Escherichia Coli Sensitive Tetracycline ATCC 9 637 | 1 | 1 |
| Escherichia Coli Resistant Tetracycline ATCC 11 303 | 0,2 | 0,2 |
| Escherichia Coli Exp.TO$_{26}$B$_6$ | 0,2 | 0,5 |
| Escherichia Coli Resistant Gentamicine, Tobramycine R 55 123 D | 0,5 | 0,5 |
| Klebsiella pneumoniae Exp. 52 145 | 1 | 1 |
| Klebsiella pneumoniae 2 536 Resistant Gentamycine | 1 | 1 |
| Proteus mirabilis (indol−) A 235 | 1 | 1 |
| Salmonella typhimurium 420 | 0,5 | 1 |
| Enterobacter cloacae 681 | 10 | 10 |
| Providencia DU 48 | 5 | 10 |
| Serratia Resistant Gentamycine 2532 | 1 | 1 |

PRODUCT OF EXAMPLE 43

| STRAINS | M.I.C. in μg/ml | |
|---|---|---|
| | 24 H | 48 H |
| Staphylococcus aureus ATCC 6 538 Penicillin Sensitive | 2 | 3 |

-continued
PRODUCT OF EXAMPLE 43

| STRAINS | M.I.C. in μg/ml | |
|---|---|---|
| | 24 H | 48 H |
| Staphylococcus aureus UC 1 128 Pen-Resistant | 3 | 3 |
| Staphylococcus aureus exp. n° 54 146 | 2 | 3 |
| Streptococcus pyogenes A 561 | 0,05 | 0,05 |
| Streptococcus faecalis 5 432 | 10 | >40 |
| Bacillus subtilis ATCC 6 633 | 1 | 2 |
| Escherichia Coli Sensitive Tetracycline ATCC 9 637 | 1 | 1 |
| Escherichia Coli Resistant Tetracycline ATCC 11 303 | 0,05 | 0,05 |
| Escherichia Coli Exp.TO$_{26}$B$_6$ | 0,2 | 0,2 |
| Escherichia Coli Resistant Gentamycine, Tobramycine R 55 123D | 0,2 | 0,2 |
| Klebsiella pneumoniae Exp. 52 145 | 0,2 | 0,2 |
| Klebsiella pneumoniae 2 536 Resistant Gentamycine | 1 | 1 |
| Proteus mirabilis (indol—) A 235 | 0,1 | 0,1 |
| Salmonella typhimurium 420 | 1 | 1 |
| Enterobacter cloacae 681 | 20 | 20 |
| Providencia Du 48 | 10 | 10 |
| Serratia Resistant Gentamycine 2 532 | 1 | 1 |

PRODUCT OF EXAMPLE 45

| STRAINS | M.I.C. in μg/ml | |
|---|---|---|
| | 24 H | 48 H |
| Staphylococcus aureus ATCC 6 538 Penicillin Sensitive | 1 | 1 |
| Staphylococcus aureus UC 1 128 Pen-Resistant | 1 | 1 |
| Staphylococcus aureus exp.n° 54146 | 1 | 1 |
| Streptococcus pyogenes A 561 | 0,05 | 0,05 |
| Streptococcus faecalis 5 432 | 5 | 5 |
| Bacillus subtilis ATCC 6 633 | 2 | 2 |
| Escherichia Coli Sensitive Tetracycline ATCC 9 637 | 0,5 | 1 |
| Escherichia Coli Resistant Tetracycline ATCC 11 303 | 0,05 | 0,05 |
| Escherichia Coli Exp.TO$_{26}$B$_6$ | 0,2 | 0,2 |
| Escherichia Coli Resistant Gentamycine, Tobramycine R 55 123 D | 0,2 | 0,2 |
| Klebsiella pneumoniae Exp. 52 145 | 0,05 | 0,05 |
| Klebsiella pneumoniae 2 536 Resistant Gentamycine | 0,5 | 0,5 |
| Proteus mirabilis (indol—) A 235 | 0,05 | 0,05 |
| Salmonella typhimurium 420 | 0,2 | 0,2 |
| Enterobacter cloacae 681 | 15 | 20 |
| Providencia Du 48 | 5 | 5 |
| Serratia Resistant Gentamycine 2 532 | 2 | 2 |

PRODUCT OF EXAMPLE 46

| STRAINS | M.I.C. in μg/ml | |
|---|---|---|
| | 24 H | 48 H |
| Staphylococcus aureus ATCC 6 538 Penicillin Sensitive | 5 | 5 |
| Staphylococcus aureus UC 1 128 Pen-Resistant | 5 | 10 |
| Staphylococcus aureus exp.n° 54 146. | 5 | 5 |
| Streptococcus pyogenes A 561 | 0,05 | 0,05 |
| Bacillus subtilis ATCC 6 633 | 1 | 2 |
| Escherichia Coli Sensitive Tetracycline ATCC 9 637 | 3 | 3 |
| Escherichia Coli Resistant Tetracycline ATCC 11 303 | 0,2 | 0,5 |
| Escherichia Coli Exp. TO$_{26}$B$_6$ | 1 | 2 |
| Escherichia Coli Resistant Gentamycine, Tobramycine R 55 123 D | 2 | 3 |
| Klebsiella pneumoniae Exp. 52 145 | 0,5 | 1 |
| Klebsiella pneumoniae 2 536 | 10 | 10 |

PRODUCT OF EXAMPLE 46

| STRAINS | M.I.C. in μg/ml | |
|---|---|---|
| | 24 H | 48 H |
| Resistant Gentamycine Proteus mirabilis (indol—) A 235 | 1 | 1 |
| Salmonella typhimurium 420 | 1 | 2 |
| Providencia Du 48 | 40 | 40 |
| Serratia Resistant Gentamycine 2 532 | 2 | 2 |

Various modifications of the products and processes of the invention may be made without departing from the spirit or scope thereof and it is to be understood that the invention is intended to be limited only as defined in the appended claims.

We claim:

1. A compound selected from the group consisting of oximes of the syn isomers of 7-[2-(2-amino-4-thiazolyl)-acetamido]-ceph-3-eme-4-carboxylic acid compounds of the formula

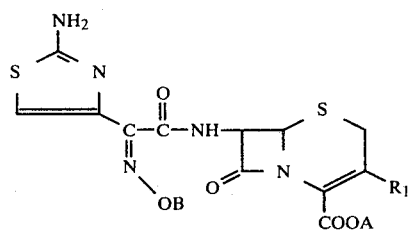

wherein B is —(CH$_2$)$_{n'}$—R$_5$, n' is an integer from 1 to 4, R$_5$ is

R$_6$ and R$_7$ are individually selected from the group consisting of hydrogen and alkyl of 1 to 4 carbon atoms and when taken together with the nitrogen to which they are attached are selected from the group consisting of phthalimido and 1-pyridinyl, R$_1$ is selected from the group consisting of CH$_3$O—, alkyl and alkylthio of 1 to 5 carbon atoms, cycloalkyl of 3 to 5 carbon atoms, —CH$_2$—S—R$_{12}$, acetoxymethyl, carbamoyloxymethyl and

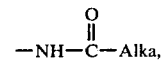

R$_{12}$ is selected from the group consisting of 2-oxo-(3H)-thiazolin-4-yl-carbonyl, 3-methyl-1,2-oxazol-5-yl-carbonyl, acyl of an alkanoic acid of 2 to 4 carbon atoms and a nitrogen heterocycle selected from the group consisting of 1,2,3-thiadiazolyl, 1,2,5-thiadiazolyl, 1,3,4-thiadiazolyl, 1,2,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl, the said heterocycles being optionally substituted with at least one substituent selected from the group consisting of methyl, ethyl, propyl, isopropyl, methoxy, ethoxy, propoxy, isopropoxy, amino, hydroxycarbonylmethyl, dimethylaminoethyl and diethylaminoethyl, Alk$_a$ is alkyl of 1 to 4 carbon atoms and A is selected from the group consisting of hydrogen, —NH₄, alkali metal, alkaline earth metal, magnesium, a non-toxic, pharmaceutically acceptable organic amine and easily cleaved ester and their non-toxic, pharmaceutically acceptable acid addition salts.

2. A compound of claim 1 wherein $R_{12}$ is acyl selected from the group consisting of acetyl, butyryl and propionyl or a heterocyclic selected from the group consisting of 1,2,3-thiadiazolyl, 1,2,5-thiadiazolyl, 1,3,4-thiadiazolyl, 1,2,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl, the said heterocycles being optionally substituted with at least one substituent selected from the group consisting of methyl, ethyl, propyl, isopropyl, methoxy, ethoxy, propoxy, isopropoxy, amino, hydroxycarbonylmethyl, diamethylaminoethyl and diethylaminoethyl.

3. A compound of claim 1 wherein $R_{12}$ is selected from the group consisting of acetyl, 1-methyl-tetrazolyl, 2-methyl-1,3,4-thiadiazolyl, 3-methyl-1,2,4-thiadiazolyl-5-yl, 3-methoxy-1,2,4-thiadiazolyl, 1,3,4-thiadiazol-5-yl, 2-amino-1,3,4-thiadiazol-5-yl, 3-hydroxycarbonylmethyl-1,2,4-thiadiazol-5-yl, 5-methoxy-1,2,4-thiadiazol-3-yl, 4-methyl-5-hydroxycarbonylmethyl-1,3-thiazol-2-yl and 1-dimethylaminoethyl-1,2,3,4-tetrazol-5-yl.

4. A compound of claim 1 wherein B is selected from the group consisting of phthalimidomethyl and aminoethyl, $R_1$ is selected from the group consisting of methyl, acetoxymethyl, 2-methyl-1,3,4-thiadizol-5-yl thiomethyl and 1-methyltetrazolyl-thio-methyl and A is hydrogen or sodium.

5. A compound of claim 1 wherein B is aminoethyl and $R_1$ is selected from the group consisting of acetoxymethyl, 2-methyl-1,3,4-thiazolyl-5-yl-thiomethyl and 1-methyltetrazol-5-yl-thiomethyl.

6. A compound of claim 1 selected from the group consisting of the syn isomer of 3-acetoxymethyl-7-[2-(2-amino-4-thiazolyl)-2-(2-aminoethoxyimino)-acetamido]-ceph-3-eme-4-carboxylic acid and its alkali metal, alkaline earth metal, magnesium, ammonium and organic amine salts and their easily cleaved esters.

7. An antibacterial composition comprising an antibacterically effective amount of at least one compound of claim 1 and an inert pharmaceutical carrier.

8. A composition of claim 7 wherein $R_{12}$ is acyl selected from the group consisting of acetyl, butyryl and propionyl or a heterocyclic selected from the group consisting of 1,2,3-thiadiazolyl, 1,2,5-thiadiazolyl, 1,3,4-thiadiazolyl, 1,2,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl, the said heterocycles being optionally substituted with at least one substituent selected from the group consisting of methyl, ethyl, propyl, isopropyl, methoxy, ethoxy, propoxy, isopropoxy, amino-hydroxycarbonylmethyl, dimethylaminoethyl and diethylaminoethyl.

9. A composition of claim 7 wherein $R_{12}$ is selected from the group consisting of acetyl, 1-methyl-tetrazolyl, 2-methyl-1,3,4-thiadiazolyl, 3-methyl-1,2,4-thiadiazolyl-5-yl, 3-methoxy-1,2,4-thiadiazolyl, 1,3,4-thiadiazolyl-5-yl, 2-amino-1,3,4-thiadiazol-5-yl, 3-hydroxycarbonylmethyl-1,2,4-thiadiazol-5-yl, 5-methoxy-1,2,4-thiadiazol-3-yl, 4-methyl-5-hydroxycarbonylmethyl-1,3-thiazol-2-yl and 1-dimethylaminoethyl-1,2,3,4-tetrazol-5-yl.

10. A composition of claim 7 wherein B is selected from the group consisting of phthalimidomethyl and aminoethyl, $R_1$ is selected from the group consisting of methyl, acetoxymethyl, 2-methyl-1,3,4-thiadizol-5-yl-thiomethyl and 1-methyltetrazolyl-thiomethyl and A is hydrogen or sodium.

11. A composition of claim 7 wherein B is aminoethyl and $R_1$ is selected from the group consisting of acetoxymethyl, 2-methyl-1,3,4-thiadiazol-5-yl-thiomethyl and 1-methyltetrazol-5-yl-thiomethyl.

12. A composition of claim 7, wherein in $R_1$ is acetoxymethyl, alkyl of 1 to 5 carbon atoms or —CH$_2$—S—R$_{12}$ and $R_{12}$ is 2-methyl-1,3,4-thiadiazolyl or 1-methyl-tetrazolyl and A is hydrogen, alkali metal, alkaline earth metal, magnesium, —NH₄ or a nontoxic, pharmaceutically acceptable organic amine.

13. A composition of claim 7 selected from the group consisting of syn isomer of 3-acetoxymethyl-7-[2-(2-amino-4-thiazolyl)-2-(2-aminoethoxyimino)-acetamido]-ceph-3-eme-4-carboxylic acid and its alkali metal, alkaline earth metal, magnesium, ammonium and organic amine salts and their easily cleaved esters.

14. A method of combatting bacterial infections in warm-blooded animals comprising administering to warm-blooded animals an antibacterially effective amount of at least one compound of claim 1.

15. A method of claim 14 wherein $R_{12}$ is acyl selected from the group consisting of acetyl, butyryl and propionyl or a heterocyclic selected from the group consisting of 1,2,3-thiadiazolyl, 1,2,5-thiadiazolyl, 1,3,4-thiadiazolyl, 1,2,4-thiadiazolyl, 1H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl, the said heterocycles being optionally substituted with at least one substituents from the group consisting of methyl, ethyl, propyl, isopropyl, methoxy, ethoxy, propoxy, isopropoxy, amino-hydroxycarbonylmethyl, dimethylaminoethyl and diethylaminoethyl.

16. A method of claim 14 wherein $R_{12}$ is selected from the group consisting of acetyl, 1-methyl-tetrazolyl, 2-methyl-1,3,4-thiadiazolyl, 3-methyl-1,2,4-thiadiazolyl,5-yl, 3-methoxy-1,2,4-thiadiazolyl, 1,3,4-thiadiazol-5-y, 2-amino-1,3,4-thiadiazol-5-yl, 3-hydroxycarbonylmethyl-1,2,4-thiadiazol-5-yl, 5-methoxy-1,2,4-thiadiazol-3-yl, 4-methyl-5-hydroxy carbonylmethyl-1,3-thiazol-2-yl and 1-dimethylaminoethyl-1,2,3,4-tetrazol-5-yl.

17. A method of claim 14 wherein B is selected from the group consisting of phthalimidomethyl and aminoethyl, $R_1$ is selected from the group consisting of methyl, acetoxymethyl, 2-methyl-1,3,4-thiadiazolyl-5-yl-thiomethyl and 1-methyltetrazolyl-thiomethyl and A is hydrogen or sodium.

18. A method of claim 14 wherein B is aminoethyl and $R_1$ is selected from the group consisting of acetoxymethyl, 2-methyl-1,3,4-thiadiazol-5-yl-thiomethyl and 1-methyltetrazol-5-yl-thiomethyl.

19. A method of claim 14 wherein n' is 1 or 2, $R_5$ is

wherein $R_6$ and $R_7$, are individually selected from the group consisting of hydrogen and alkyl of 1 to 4 carbon atoms and taken together with the nitrogen atom to which they are attached are selected from the group consisting of phthalimido and 1-pyridinyl, $R_1$ is acetoxy-methyl, alkyl of 1 to 5 carbon atoms or $-CH_2-S-R_{12}$ and $R_{12}$ is 2-methyl-1,3,4-thiadiazol or 1-methyl-tetrazolyl and A is hydrogen, alkali metal, alkaline earth metal, magnesium, $-NH_4$ or a non-toxic, pharmaceutically acceptable organic amine.

20. A method of claim 14 wherein said compounds is selected from the group consisting of syn isomer of 3-acetoxymethyl-7-[2-(2-amino-4-thiazolyl)-2-(2-aminoethoxyimino)-acetamido]ceph-3-eme-4-carboxylic acid and its alkali metal, alkaline earth metal, magnesium, ammonium and organic amine salts and their easily cleaved esters.

* * * * *